(12) United States Patent
Webb et al.

(10) Patent No.: US 8,969,405 B2
(45) Date of Patent: Mar. 3, 2015

(54) ANTICANCER COMPOUNDS AND METHODS OF MAKING AND USING SAME

(75) Inventors: Thomas R. Webb, Millington, TN (US); Chandraiah Lagisetti, Memphis, TN (US)

(73) Assignee: St. Jude Children's Research Hospital, Memphis, TN (US)

(*) Notice: Subject to any disclaimer, the term of this patent is extended or adjusted under 35 U.S.C. 154(b) by 876 days.

(21) Appl. No.: 12/999,218

(22) PCT Filed: Jun. 22, 2009

(86) PCT No.: PCT/US2009/048167
§ 371 (c)(1),
(2), (4) Date: Mar. 28, 2011

(87) PCT Pub. No.: WO2009/155606
PCT Pub. Date: Dec. 23, 2009

(65) Prior Publication Data
US 2011/0178098 A1 Jul. 21, 2011

Related U.S. Application Data

(60) Provisional application No. 61/074,627, filed on Jun. 21, 2008.

(51) Int. Cl.
*C07D 493/10* (2006.01)
*C07D 319/06* (2006.01)
*A61K 31/351* (2006.01)
*A61K 31/357* (2006.01)

(52) U.S. Cl.
CPC ............ *C07D 493/10* (2013.01); *A61K 31/357* (2013.01); *C07D 319/06* (2013.01); *A61K 31/351* (2013.01)
USPC ............................ 514/452; 549/369; 549/370

(58) Field of Classification Search
CPC ... C07D 493/10; C07D 319/06; A61K 31/357
USPC .......................................... 514/452; 549/369
See application file for complete search history.

(56) References Cited

U.S. PATENT DOCUMENTS

2008/0096879 A1* 4/2008 Koide et al. ................. 514/231.5

FOREIGN PATENT DOCUMENTS

WO WO-2009/155606 A1 12/2009

OTHER PUBLICATIONS

Albert Brian J, et al. (2007) Total syntheses, fragmentation studies, and antitumor/; antiproliferative activities of FR901464 and its low picomolar analogue. J. Am. Chem. Soc., 129: 2648-2659.
Beal SL. (2001) Way to fit a PK model with some data below the quantification limit. J. Pharmacokinet Pharmacodyn, 28(5): 481-504.
Chou TC, et al. (1984) Quantitative analysis of dose-effect relationships: the combined effects of multiple drugs or enzyme inhibitors. Adv. Enzyme Regul., 22: 27-553.
Corey EJ, et al. (1965) Dimethyloxosulfonium methylide and dimethylsulfonium methylide. Formation and application to organic synthesis. J. Am. Chem. Soc., 87: 1353-1364.
Decker M, et al. (2009) Mammalian epoxide hydrolases in xenobiotic metabolism and signalling. Arch Toxicol, 8(4): 297-318.
Fan L, et al. (2011) Sudemycins, novel small molecule analogues of FR901464, induce alternative gene splicing. ACS Chem Biol, 6(6): 582-589.
Golas, et al. (2003) Molecular Architecture of the Multiprotein Splicing Factor SF3b. Science, 300(5621): 980-984.
Gundluru MK, et al. (2011) Design, synthesis and initial biological evaluation of a novel pladienolide analog scaffold. Med Chem Comm, 2(9): 904-908.
Hann B, et al. (2001) Building 'validated' mouse models of human cancer. Curr Opin Cell Biol, 13(6): 778-784.
Kaida, et al. (2007) Spliceostatin A targets SF3b and inhibits both splicing and nuclear ; retention of pre-mRNA. Nature Chemical Biology, 3: 576-583.
Kotake Y, et al. (2007) Splicing factor SF3b as a target or the antitumor natural product pladienolide. Nat Chem Biol, 3: 570-575.
Lagisetti C, et al. (2008) Antitumor Compounds Based on a Natural Product Consensus Pharmacophore. J. Med. Chem., 51: 6220-6224.
Lagisetti C, et al. Optimization of Antitumor Modulators of Pre-mRNA Splicing. Abstract. Department of Chemical Biology and Therapeutics, Preclinical PK Shared Resource, St. Jude Children's Research Hospital, Memphis, TN.
Lagisetti C, et al. (2009) Synthetic mRNA Splicing Modulator Compounds with in Vivo Antitumor Activity. J. Med. Chem., 52: 6979-6990.
Liu JY, et al. (2009) Sorafenib has soluble epoxide hydrolase inhibitory activity, which contributes to its effect profile in vivo. Mol. Cancer Ther., 8: 2193-2203.
LoPiccolo J, et al. (2008) Targeting the P13K/Akt/m TOR pathway: effective combinations and clinical considerations. Drug Res. Updat., 11(1-2): 32-50.
Maione TE, et al. (1990) Inhibition of tumor growth in mice by an analogue of platelet factor 4 that lacks affinity for heparin and retains potent angiostatic activty. Cancer Res., 51(8): 2077-2083.
Maira SM, et al. (2008) Identification and characterization of NVP-BEZ235, a new orally available dual phosphatidylinositol 3-kinase/mammalian target of rapamycin inhibitor with potent in vivo antitumor activity. Mol. Cancer Ther., 7(7): 1851-1863.
Malcovati L, et al. (2011) Clinical significance of *SF3B1* mutations in myelodysplastic syndromes and myelodysplastic/myeloproliferative neoplasm. Blood, 118(24): 6229-6246.

(Continued)

*Primary Examiner* — Kristin Vajda
*Assistant Examiner* — Valerie Rodriguez-Garcia
(74) *Attorney, Agent, or Firm* — Ballard Spahr LLP

(57) ABSTRACT

In one aspect, the invention relates to compounds having anticancer activity; synthetic methods for making the compounds; pharmaceutical compositions comprising the compounds; and methods of treating disorders associated with uncontrolled cellular proliferation using the compounds and compositions. This abstract is intended to be used as a scanning tool for purposes of searching in the particular art and is not intended to be limiting of the present invention.

12 Claims, 3 Drawing Sheets

(56) References Cited

OTHER PUBLICATIONS

Massad SK, et al. (1983) A series of (2S)-2-O-protected-2-hydroxypropanals (L-lactaldehydes) suitable for use as optically active intermediates. The Journal of Organic Chemistry 48: 5180-8182.

Mitsunobu O. (1981) The use of diethyl azodicarboxylate and triphenylphosphine in synthesis and transformation of natural products. Synthesis, 1981(1): 1-28.

Mizui Y, et al. (2004) Pladienolides, new substances from culture of *Streptomyces platensis* Mer-11107. III. In vitro and in vivo antitumor activities. J. Antibiot., 57: 188-196.

Motoyoshi H, et al. (2004) Structure-activity relationship for FR901464: a versatile method for the conversion and preparation of biologically active biotinylated proves. Biosci. Biotechnol. Biochem., 68: 2178-2182.

Motoyoshi H, et al. (2006) Total synthesis of FR901464: second generation. Tetrahedron, 62: 1378-1389.

Nagarajan S, et al. (1987) Chemistry of naturally occurring polyamines. 11. Unsaturated spermidine and spermine derivatives. J Org. Chem., 52: 5044-5046.

Nakajima H, et al. (1996) New antitumor substances, FR901463, FR901464 and FR901465. II. Activities against experimental tumors in mice and mechanism of action. J. Antibiot (Tokyo), 49(12): 1204-1211.

Nakajima H, et al. (1996) New antitumor substances, FR901463, FR901464 and FR901465. I. Taxonomy, fermentation, isolation, physicochemical properties and biological activities. J. Antibiot., 49: 1196-1203.

Nakajima H, et al. (1997) New antitumor substances, FR901463, FR901464 and FR901465. III. Structures of FR 901463, FR901464 and FR901465. J. Antibiot., 50: 96-99.

NCI R01 Grant No. CA14074-03.

Ohta T, et al. (1995) Asymmetric Hydrogenation of Olefins with Aprotic Oxygen Functionalities Catalyzed by BINAP-RU(II) Complexes. J. Org. Chem., 60: 357-363.

Ouellet SG, et al. (2007) Enantioselective organocatalytic transfer hydrogenation reactions using Hantzsch esters. Acc. Chem. Res., 40: 1327-1339.

Pessah N, et al. (2004) Bioactivation of carbamate-based 20(S)-camptothecin prodrugs. Bioorg. Med. Chem., 12: 1859-1866.

Rymond B, et al. (2007) Targeting the spliceosome. Nature Chemical Biology, 3: 533-535.

Sage, et al. (1995) Inhibition of endothelial cell proliferation by SPARC is mediated through a Ca(2+)-binding EF-hand sequence. J: Cell. Biochem., 57: 127-140.

Thompson CF, et al. (2001) FR901464: total synthesis, proof of structure, and evaluation of synthetic analogues. J. Am. Chem. Soc., 123: 9974-9983.

Tolsma SS, et al. (1993) Peptides Derived from Two Separate Domains of the Matrix Protein Thrombospondin-1 have Anti-angiogenic Activity. J. Cell Bio., 122: 497-511.

Tripathi M, et al. (2012) Sudemycin Selectively Inhibits Growth of Primary Murine Hematopoietic Cells Expressing Mutant U2AF1. Oral and Poster Abstracts. Myelodysplastic Syndromes: Functonal/Pathophysiologic studies of MDS. Monday, Dec. 10, 2012 Goergia World Congress Center.

Tuttle JB, et al. (2006) Organocatalytic Transfer Hydrogenation of Cyclic Enones. Journal of the American Chemical Society, 128: 12662-12663.

Valverde S, et al. (1987) the reaction of carbohydrate-derived alkoxyaldehydes with methoxycarbonylmethylenetriphenylphosphorane: stereoselective synthesis of β-unsaturated esters. Tetrahedron, 43: 1895-1901.

Yamanaka N, et al. (2001) Engraftment of tonsillar mononuclear cells in human skin/SCID mouse chimera—validation of a novel xenogeneic transplantation model for autoimmune diseases. Microbiol Immunol, 45(7): 507-514.

Yoon NM, et al. (1973) Selective reductions. XIX. Rapid reaction of carboxylic acides with ; borane-tetrahydrofuran. Remarkably convenient procedure for the selective conversion of carboxylic acids to the corresponding alcohols in the presence of other functional groups. J. Org. Chem., 38: 2786-2792.

International Preliminary Report on Patentability issued by the International Bureau on Dec. 21, 2010 for ; PCT/US2009/048167 filed Jun. 22, 2009 and published as WO 2009/155606 on Dec. 23, 2009 (Applicants 0 St. Jude Children's Research Hospital, et al.; Inventors—Webb, et al.) (10 pages).

International Search Report mailed by the International Bureau on Oct. 5, 2009 for PCT/US2009/048167 filed Jun. 22, 2009 and published as WO 2009/155606 on Dec. 23, 2009 (Applicants—St. Jude Children's Research Hospital, et al.; Inventors—Webb, et al.) (4 pages).

Written Opinion issued by the International Bureau on Oct. 5, 2009 for PCT/US2009/048167 file Jun. 22, 2009 and published as WO 2009/155606 on Dec. 23, 2009 (Applicants—St. Jude Children's Research Hospital, et al.; Inventors—Webb, et al.) (9 pages).

\* cited by examiner pladienolide A (1): R = H, R' = H
B (2): R = H, R' = Ac
D (3): R = OH, R' = Ac
E7107 (4): R = OH, R' = CO—N

FR901464

ANTICANCER COMPOUNDS AND METHODS OF MAKING AND USING SAME

CROSS-REFERENCE TO RELATED APPLICATIONS

This application claims the benefit of U.S. Application No. 61/074,627, filed Jun. 21, 2008, which is hereby incorporated herein by reference in its entirety.

BACKGROUND

Diseases of uncontrolled cellular proliferation, including cancer, can affect people of all ages, including fetuses. Cancer alone is thought to be responsible for approximately 13% of all deaths worldwide. During 2007, about 7.8 million people died of cancer. The production of cancer cells can be caused by various genetic abnormalities, with risk factors including errors in cell replication, exposure to carcinogens, such as radiation, chemicals, or infectious agents. Cancer cells are typically characterized by hyperactive growth and division, protection against programmed cell death, loss of respect for normal tissue boundaries, and the ability to thrive in a diverse range of tissues. Although cancer research remains a bourgeoning area of basic and clinical research, there still to date no cure for cancer.

Chemotherapeutic agents and radiation, which cause mutations in actively dividing cells, are intended to selectively kill the cancer cells while not effecting normal cells. Unfortunately, these cytotoxic agents, while effective in managing several types of cancer, are limited in their utility due to adverse side effects and lack of specificity for cancer cells. Advancement in the understanding of cell biology and cancer has lead to the advent of new more selective treatments providing hope for cancer patients.

With the development of chemotherapy, survival and recovery rates of cancer patients have improved. However, anticancer agents are problematic in terms of being highly toxic and thus severely damaging to normal cells. To overcome such a side effect of anticancer agents, many recent studies have focused on developing alternative anticancer substances capable of specifically suppressing proliferation of tumor cells.

Unfortunately, however, due to the prevalence of many different types of cancers and due to the complexity of cancers, there still remains a need to develop new anti-cancer therapeutics, including the development of compounds displaying anticancer activity.

SUMMARY

In accordance with the purpose(s) of the invention, as embodied and broadly described herein, the invention, in one aspect, relates to compounds useful as anticancer agents, methods of making same, pharmaceutical compositions comprising same, and methods of treating disorders using the compounds and compositions.

Disclosed are compounds having a structure represented by a formula:

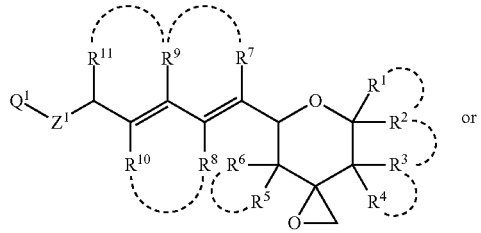

or

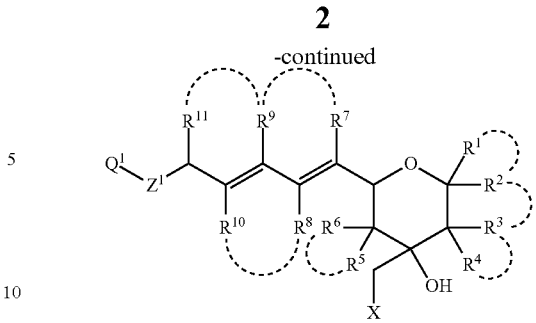

wherein each of $R^1$, $R^2$, $R^3$, $R^4$, $R^5$, and $R^6$ independently comprises halide, hydrogen, hydroxyl, amino, thiol, or optionally substituted organic residue comprising from 1 to 6 carbons; wherein each of $R^7$, $R^8$, $R^9$, $R^{10}$, and $R^{11}$ independently comprises halide, hydrogen, hydroxyl, amino, thiol, or optionally substituted organic residue comprising from 1 to 6 carbons; and wherein each ----- is an optional covalent bond; and wherein X is a leaving group; wherein $Z^1$ comprises an optionally substituted 3, 4, 5, 6, or 7 membered ring; wherein if $R^5$ or $R^6$ is hydroxyl or alkoxyl, then $Z^1$ comprises a ring with no more than three chiral centers; and wherein $Q^1$ comprises an optionally substituted organic residue comprising from 1 to 26 carbons; or a pharmaceutically acceptable derivative thereof.

Also disclosed are methods for inhibiting cell replication comprising the step of contacting at least one cell with an effective amount of a compound having the structure represented by the formula:

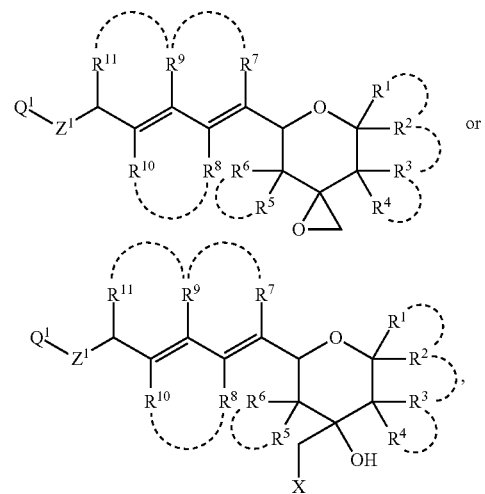

wherein each of $R^1$, $R^2$, $R^3$, $R^4$, $R^5$, and $R^6$ independently comprises halide, hydrogen, hydroxyl, amino, thiol, or optionally substituted organic residue comprising from 1 to 6 carbons; wherein each of $R^7$, $R^8$, $R^9$, $R^{10}$, and $R^{11}$ independently comprises halide, hydrogen, hydroxyl, amino, thiol, or optionally substituted organic residue comprising from 1 to 6 carbons; and wherein each ----- is an optional covalent bond; and wherein X is a leaving group; wherein $Z^1$ comprises an optionally substituted 3, 4, 5, 6, or 7 membered ring; wherein if $R^5$ or $R^6$ is hydroxyl or alkoxyl, then $Z^1$ comprises a ring with no more than three chiral centers; and wherein $Q^1$ comprises an optionally substituted organic residue comprising from 1 to 26 carbons, or a pharmaceutically acceptable derivative thereof; thereby inhibiting replication of the at least one cell.

Also disclosed are methods of treating a disorder of uncontrolled cellular proliferation in a subject comprising the step of administering to the subject a therapeutically effective amount of one or more disclosed compounds, thereby treating the disorder in the subject.

Also disclosed are methods of a treating a genetic disorder in a subject comprising the step of administering to the subject a therapeutically effective amount of one or more disclosed compounds, thereby treating the genetic disorder in the subject.

Also disclosed are methods of making an spiro epoxide derivative, comprising the steps of: (a) providing a compound having a structure represented by the formula:

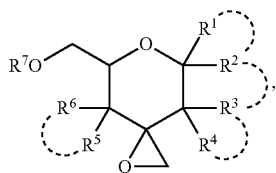

wherein each of $R^1$, $R^2$, $R^3$, $R^4$, $R^5$, $R^6$, and $R^7$ independently comprises halide, hydrogen, hydroxyl, amino, thiol, or optionally substituted organic residue comprising from 1 to 6 carbons; wherein each ----- is an optional covalent bond; and (b) performing an oxidation reaction to provide the Spiro epoxide derivative.

Also disclosed are dosage forms comprising a therapeutically effective amount of at least one product of a disclosed synthetic method and a pharmaceutically acceptable carrier.

Also disclosed are dosage forms for administration to a subject comprising a therapeutically effective amount of one or more disclosed compounds and a pharmaceutically acceptable carrier.

Also disclosed is a method of treating a disorder of uncontrolled cellular proliferation in a subject comprising the step of administering to the subject a disclosed dosage form, thereby treating the disorder of uncontrolled cellular proliferation.

Additional advantages will be set forth in part in the description which follows, and in part will be obvious from the description, or can be learned by practice. Other advantages will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several embodiments and together with the description serve to explain the principles of the invention.

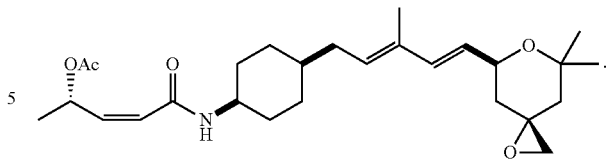

Figure 4:
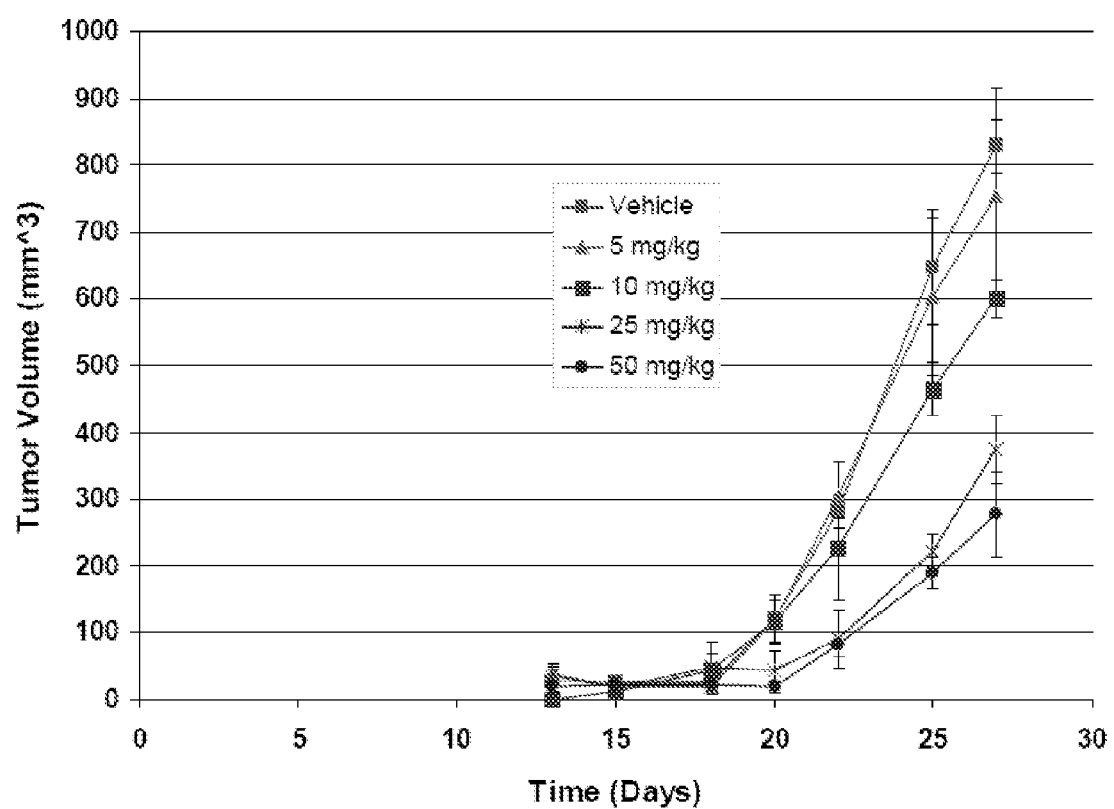

FIG. 4 is a plot showing compound 15 inhibition of tumor growth in JeKo-1 tumor-bearing mice. JeKo-1 tumors were transplanted to NOD/SCID mice on day 0 and, beginning on day 4, the mice (4 per group) received IV injections of vehicle, 5, 10, 25 or 50 mg/kg of compound 15 daily for five consecutive days. Vehicle alone did not inhibit tumor growth as compared to saline-treated mice (data not shown). Arrows indicate the dosing schedule. The data are represented as mean±SEM.

Additional advantages will be set forth in part in the description which follows, and in part will be obvious from the description, or may be learned by practice. Other advantages will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Before the present compounds, compositions, articles, devices, and/or methods are disclosed and described, it is to be understood that they are not limited to specific synthetic methods unless otherwise specified, or to particular reagents unless otherwise specified, as such can, of course, vary. It is also to be understood that the terminology used herein is for the purpose of describing particular aspects only and is not intended to be limiting.

Although any methods and materials similar or equivalent to those described herein can be used in the practice or testing of the present invention, example methods and materials are now described.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein can be different from the actual publication dates, which can require independent confirmation.

A. Definitions

As used in the specification and the appended claims, the singular forms "a," "an" and "the" include plural referents unless the context clearly dictates otherwise. Thus, for example, reference to "a component," "a compound," or "a dosage form" includes mixtures of two or more such components, compounds, or dosage forms, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the application, data is provided in a number of different formats and that this data represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not. For example, the term "optionally substituted," as used herein, means that the groups in question are either unsubstituted or substituted with one or more of the substituents specified. When the groups in question are substituted with more than one substituent the substituents can be the same or different.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinbelow. The permissible substituents can be one or more and the same or different for appropriate organic compounds. For purposes of this disclosure, the heteroatoms such as nitrogen can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited to alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic residues, wherein the terms are defined elsewhere herein. Organic residues can preferably comprise 1 to 36 carbons, 1 to 26 carbons, 1 to 18 carbon atoms, 1 to 15 carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

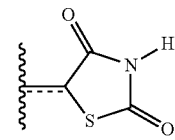

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, for example, 1 to 12 carbon atoms, 1 to 9 carbon atoms, 1 to 6 carbon atoms, 1 to 4 carbon atoms. Examples of alkyl include, but are not limited to methyl, ethyl, n propyl, isopropyl, n butyl, isobutyl, t butyl, pentyl, hexyl, heptyl, octyl, decyl, tetradecyl, hexadecyl, eicosyl, tetracosyl and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol, as described below. The term "halogenated alkyl" specifically refers to an alkyl group that is substituted with one or more halide, e.g., fluorine, chlorine, bromine, or iodine. A "lower alkyl" group is an alkyl group containing from one to six (e.g., from one to four, one to three, or one to two) carbon atoms.

The term "alkoxy" as used herein is an alkyl group bound through a single, terminal ether linkage; that is, an "alkoxy" group can be defined as —OA where A is alkyl as defined above.

The term "alkenyl" as used herein is a hydrocarbon group of from 2 to 24 carbon atoms with a structural formula containing at least one carbon-carbon double bond. Asymmetric structures such as (AB)C=C(CD) are intended to include both the E and Z isomers. This can be presumed in structural formulae herein wherein an asymmetric alkene is present, or it can be explicitly indicated by the bond symbol C=C.

The term "alkynyl" as used herein is a hydrocarbon group of 2 to 24 carbon atoms with a structural formula containing at least one carbon-carbon triple bond, i.e., C≡C.

The term "aryl" as used herein is any carbon-based aromatic group including, but not limited to, benzene, naphthalene, phenyl, biphenyl, etc. The term "aromatic" also includes "heteroaryl," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and contains at least one carbon-carbon double bound, C=C. Examples of cycloalkenyl groups include, but are not limited to, cyclopropenyl, cyclobutenyl, cyclopentenyl, cyclopentadienyl, cyclohexenyl, etc. The term "heterocycloalkenyl" is a cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein.

The term "heterocycle" as used herein is intended to include the following groups, which can be optionally substituted: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "heterocycle" as used herein is also intended to include, but is not limited to, the following groups which can be optionally substituted: methylenedioxyphenyl, imidazopyridyl, imidazopyrimidinyl, imidazopyridazinyl, imidazopyrazinyl, imidazotriazinyl, imidazothiopheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups which can be optionally substituted: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "aldehyde" as used herein is represented by the formula —C(O)H.

The terms "amine" or "amino" as used herein are represented by the formula —NAA$^1$A$^2$, where A, A$^1$, and A$^2$ can be, independently, any suitable substituent, including hydrogen, alkyl, halogenated alkyl, alkenyl, alkynyl, aryl, heteroaryl, cycloalkyl, cycloalkenyl, heterocycloalkyl, or heteroalkenyl group described above. An amino group can be present as an N-oxide. An "N-oxide," as used herein is represented by a formula N(O)AA$^1$A$^2$, where A, A$^1$, and A$^2$ are as defined above. An "N-oxide" can comprise a dative bond, i.e., N→O, which is sometimes represented by the formula, N=O.

The term "carboxylic acid" as used herein is represented by the formula —C(O)OH.

The term "ester" as used herein is represented by the formula —C(O)OA, where A can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula AOA1, where A and A1 can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula —C(O)—.

The term "halide" as used herein refers to the halogens fluorine, chlorine, bromine, and iodine.

The term "hydroxamate" as used herein is represented by the formula —C(O)NHOH.

The term "hydroxyl" as used herein is represented by the formula —OH.

The term "nitro" as used herein is represented by the formula —NO$_2$.

The term "thiol" as used herein is represented by the formula —SH.

The term "cyano" as used herein is represented by the formula —CN.

The term "azide" as used herein is represented by the formula —N$_3$.

The term "carboxamido" as used herein is represented by the formula —C(O)NH—.

The term "trifluoromethyl" as used herein is represented by the formula —CF$_3$.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

The term "substantially" as used herein can be applied to modify any quantitative representation which could permissibly vary without resulting in a change in the basic function to which it is related. For example, the term "substantially pure" is intended to refer to a mixture wherein the desired compound is present in from about 70% to about 100% parts by weight, e.g., 75%, 80%, 90%, 95%, 99%. The term "substantially enantiopure" is intended to refer to a mixture of chiral isomers (e.g., enantiomers, diastereomers, meso compounds, and the like) wherein one compound in the mixture is present in about 70%, or about 80%, or about 85%, or about 90%, or about 95% parts by weight.

The term "enantiomeric excess" is intended to refer to the absolute difference between the mole fraction of each enantiomer in an enantiomeric mixture. Thus, enantiomeric excess exists when one enantiomer in a mixture of enantiomers is present in a greater amount than the other(s). As an example, a sample with 70% of an R isomer and 30% of an S will have an enantiomeric excess of 40%. This can also be thought of as a mixture of 40% pure R with 60% of a racemic mixture (which contributes 30% R and 30% S to the overall composition).

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as Chemdraw (CAMBRIDGESOFT® Corporation, U.S.A.).

The term "hydrolysable residue" is meant to refer to a functional group capable of undergoing hydrolysis, e.g., under basic or acidic conditions. Examples of hydrolysable residues include, without limitatation, acid halides, activated carboxylic acids, and various protecting groups known in the art (see, for example, "Protective Groups in Organic Synthesis", T. W. Greene, P. G. M. Wuts, Wiley-Interscience, 1999).

The term "leaving group" is meant to refer to an atom (or a group of atoms) with electron withdrawing ability that can be displaced as a stable species, taking with it the bonding electrons. Examples of suitable leaving groups include sulfonate esters, including, but not limited to, triflate, mesylate, tosylate, brosylate, and halides.

Certain instances of the above defined terms can occur more than once in the structural formulae, and upon such occurrence each term shall be defined independently of the other. For example, if more than one compound is represented by a formula comprising an R$^1$ substituent, each R$^1$ of each formula shall be treated independently. Thus, if R$^1$ is defined as alkyl in one instance, R$^1$ is not necessarily alkyl in another instance.

As used herein, and without limitation, the term "derivative" is used to refer to any compound which has a structure derived from the structure of the compounds disclosed herein and whose structure is sufficiently similar to those disclosed herein and based upon that similarity, would be expected, by one skilled in the art, to exhibit the same or similar activities and utilities as the claimed compounds, or to induce, as a precursor, the same or similar activities and utilities as the claimed compounds. For example, a derivative can be a prodrug, a metabolite, or a pharmaceutically acceptable derivative.

The term "pharmaceutically acceptable" means a material that is not biologically or otherwise undesirable, i.e., without causing any undesirable biological effects or interacting in a deleterious manner.

The term "pharmaceutically acceptable derivative" refers to any homolog, analog, or fragment corresponding to the disclosed compounds which can modulate spliceosome activity. A "pharmaceutically acceptable derivative," for example, includes any pharmaceutically acceptable salt, ester, amide, salt of an ester or amide, or other derivative of a disclosed compound.

The term "modulate" or "modulating" refers to the ability of an agent to regulate a desired response, e.g., inhibiting cellular proliferation including cell killing. Modulate, as used herein, can refer to a process by which an agent elevates or reduces, or increases or decreases, a desired response. Modulate refers to the ability of an agent to regulate a response either directly or indirectly. Modulate can refer to a process by which an agent substantially inhibits, stabilizes, or prevents a response when a response would otherwise increase. Modulate can also refer to a process by which an agent substantially stabilizes, enhances, or maintains a response when a response would otherwise decrease. Thus, compounds disclosed herein as spliceosome modulators, can function as inhibitory agents, for example. Included within "inhibitory agents" is a preventative agent, i.e. a compound capable of eliminating uncontrolled cellular proliferation.

As used herein, a "spliceosome" is intended to refer to a ribonucleoprotein complex that removes introns from one or more pre-mRNA segments.

A "cytotoxic" substance is intended to refer to a substance that imparts a toxic effect on a cell. In one aspect, a toxic effect can be a splicing defect. In a further aspect, a splicing defect can result in a toxic effect, and vice versa. In a further aspect, a cytotoxic substance is toxic against a certain cell (e.g., a tumor cell) and non-toxic, or not as toxic, against other cells (e.g., non-tumor cells).

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein.

The term "contacting" as used herein refers to bringing a disclosed compound and a cell or other biological entity together in such a manner that the compound can affect the activity of the target (e.g., the cell, etc.), either directly; i.e., by interacting with the target itself, or indirectly; i.e., by interacting with another molecule, co-factor, factor, or protein on which the activity of the target is dependent.

As used herein, the term "cancer" means any condition characterized by cells displaying uncontrolled growth, invasion of normal tissue, and/or metastasis.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, "diagnosed" means having been subjected to a physical examination by a person of skill, for example, a physician, and found to have a condition that can be diagnosed or treated by the compounds, compositions, or methods disclosed herein. For example, "diagnosed with a disorder associated with uncontrolled cellular proliferation" means having been subjected to a physical examination by a person of skill, for example, a physician, and found to have a condition that can be diagnosed or treated by a compound or composition that can favorably affect uncontrolled cellular proliferation (e.g., a spliceosome modulator).

Disclosed are the components to be used to prepare the compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions. Thus, if there are a variety of additional steps that can be performed it is understood that each of these additional steps can be performed with any specific embodiment or combination of embodiments of the methods.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

B. Pharmacophore Model

Figure 1:
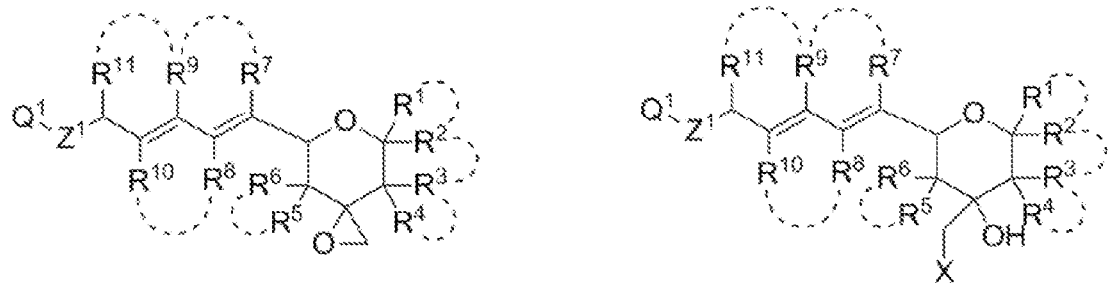
FIG. 1 shows formulae used to represent various disclosed compounds.
Figure 2:
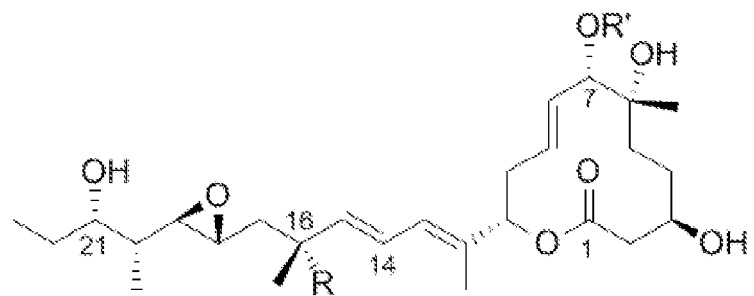
FIG. 2 shows the structures of pladienolide B (top) and FR901464 (bottom).
Figure 2:
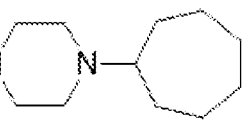
Figure 2:
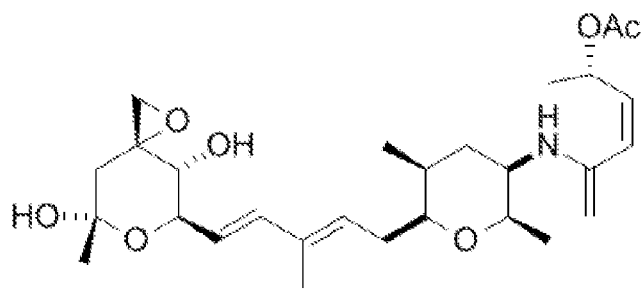
Figure 3:
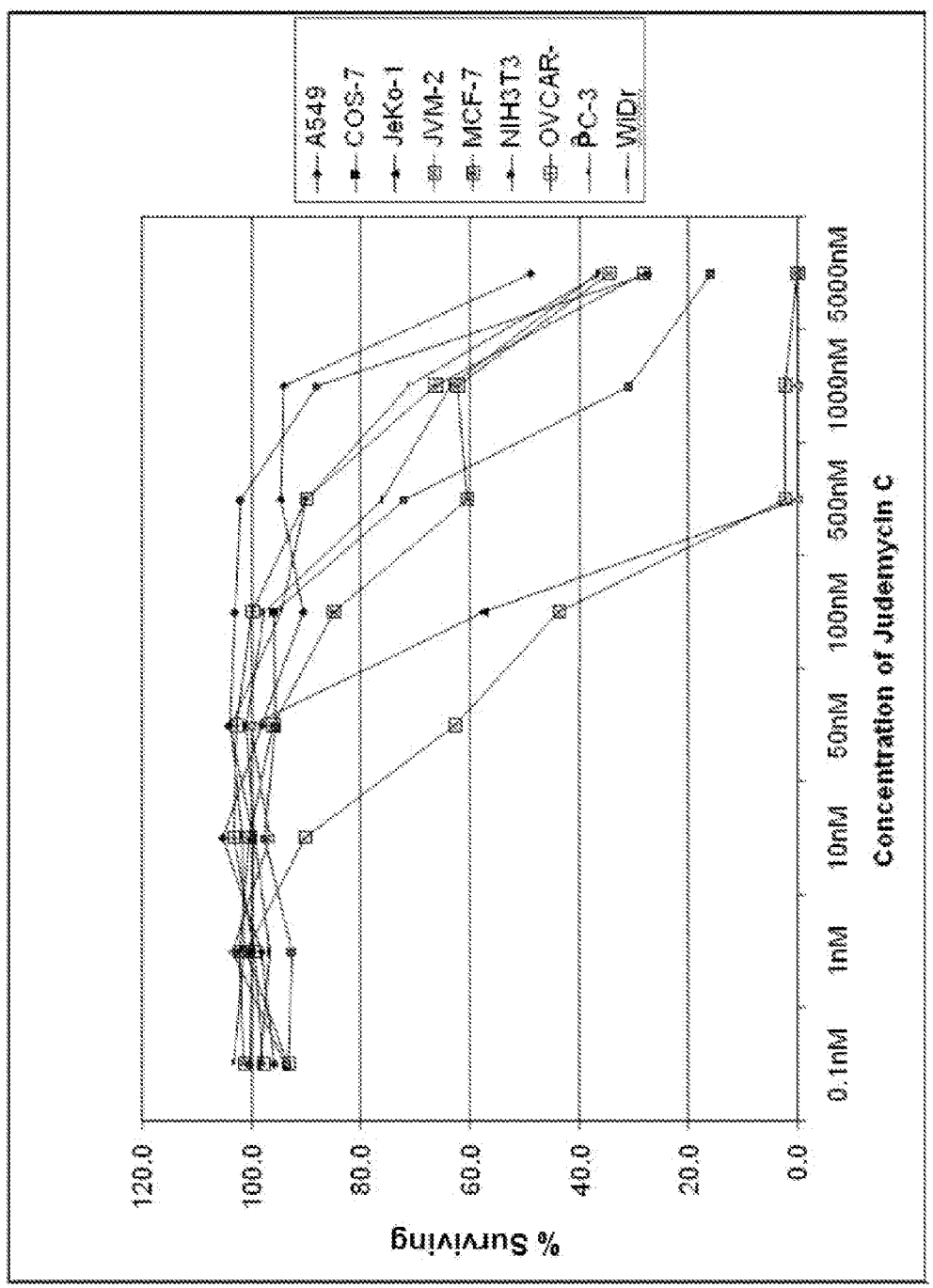
FIG. 3 shows a graph plotting the efficacy of an exemplary disclosed compound against various malignant cell lines. The exemplary compound used to obtain the data shown in FIG. 3 is represented by the formula.

In one aspect, the present disclosure relates to a pharmacophore related to two unrelated natural products, FR901464 (FR) and pladienolide (PD) (FIG. 2) (Rymond, B., "Targeting the spliceosome," Nature Chemical Biology, 2007, 3, 533-535). Both of these compounds were reported to have a similar effect on the cell cycle, specifically cell cycle arrest at the G1 and G2/M phases. Without wishing to be bound by theory, in some aspects, these drugs can inhibit mRNA splicing. In some aspects, these drugs can inhibit spliceosome function. In some aspects, these drugs can have this effect via an interaction with the SF3b subunit of the spliceosome.

The first of these natural products to be discovered, FR, showed activity in in vivo cancer animal models (Nakajima, H.; Hori, Y.; Terano, H.; Okuhara, M.; Manda, T.; Matsumoto, S.; Shimomura, K. New antitumor substances, FR901463, FR901464 and FR901465. II. Activities against experimental tumors in mice and mechanism of action. J Antibiot (Tokyo) 1996, 49, 1204-11). On the other hand, PD based compounds (first reported in 2004) have shown a very broad therapeutic window (Kotake, Y.; Sagane, K.; Owa, T.; Mimori-Kiyosue, Y.; Shimizu, H.; Uesugi, M.; Ishihama, Y.; Iwata, M.; Mizui, Y. Splicing factor SF3b as a target of the antitumor natural product pladienolide. Nat Chem Biol 2007, 3, 570-5). It has recently been reported that a derivative of pladienolide B has entered human clinical trials for cancer.

It was discovered that despite structural dissimilarities between FR and PD, they share certain common features that can overlap in low energy conformations in three dimensions. Using this information, a hypothetical 3D pharmacophore model was developed that allowed the proposal of various disclosed compounds with potential for the treatment of cancers and related disorders.

Thus, in various aspects, the disclosed compounds can have similar activities to those reported for the FR series compounds and PD series compounds.

It will be appreciated that the structural changes of the compounds disclosed herein, in various aspects, can eliminate a total of 6 chiral centers when compared to FR, which can allow for the synthesis of a diverse library of target compounds.

C. Compounds

1. Structure

In one aspect, disclosed is a compound having a structure represented by a formula:

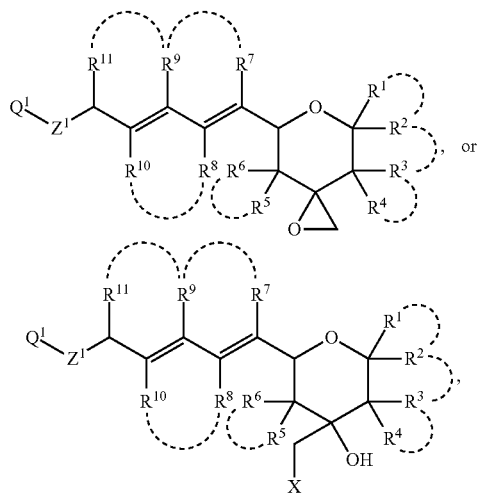

wherein each of $R^1$, $R^2$, $R^3$, $R^4$, $R^5$, and $R^6$ independently comprises halide, hydrogen, hydroxyl, amino, thiol, or optionally substituted organic residue comprising from 1 to 6 carbons; wherein each of $R^7$, $R^8$, $R^9$, $R^{10}$, and $R^{11}$ independently comprises halide, hydrogen, hydroxyl, amino, thiol, or optionally substituted organic residue comprising from 1 to 6 carbons; and wherein each ----- is an optional covalent bond; and wherein X is a leaving group; wherein $Z^1$ comprises an optionally substituted 3, 4, 5, 6, or 7 membered ring; wherein if $R^5$ or $R^6$ is hydroxyl or alkoxyl, then $Z^1$ comprises a ring with no more than three chiral centers; and wherein $Q^1$ comprises an optionally substituted organic residue comprising from 1 to 26 carbons; or a pharmaceutically acceptable derivative thereof.

In a further aspect, $Z^1$ comprises a ring with no more than two chiral centers in the 3, 4, 5, 6, or 7 membered ring. For example, $Z^1$ can have two chiral centers in the 3, 4, 5, 6, or 7 membered ring. In a specific aspect, $Z^1$ can have two chiral centers in the 6 membered ring.

In a further aspect, neither $R^5$ nor $R^6$ comprises hydroxyl. In a still further aspect, at least one of $R^5$ and $R^6$ comprises hydroxyl.

In one aspect, $Z^1$ comprises a ring with no more than three stereocenters. In a further aspect, $Z^1$ comprises a ring that can include but is not limited to:

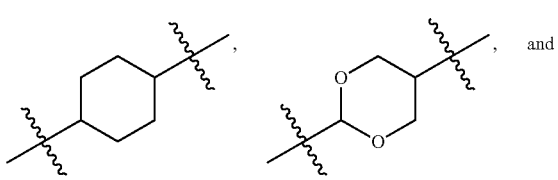 and

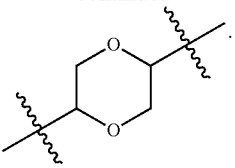

A "stereocenter," as used herein can mean a geometrical center with restricted rotation, e.g., a ring, such as a constrained ring, or a double bond. In a further aspect, a "stereocenter" can mean a chiral center. Thus, as an non-limiting example, $Z^1$ would not comprise a ring with a structure represented by a formula:

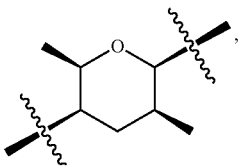

which, assuming the structural features beyond the connecting points are asymmetrical, would comprise a total of four stereocenters, which in this case are chiral centers.

In a further aspect, $R^1$ and $R^2$ independently comprise hydroxyl, methyl, ethyl, propyl, or butyl, and $R^3$, $R^4$, $R^5$, and $R^6$ independently comprises hydrogen. In a still further aspect, both $R^1$ and $R^2$ independently comprise methyl. In one aspect, at least one of $R^1$ and $R^2$ comprises hydroxyl.

In one aspect, each of $R^7$, $R^8$, $R^9$, $R^{10}$, and $R^{11}$ independently comprises hydrogen or optionally substituted organic residue comprising from 1 to 4 carbons. In a specific aspect, $R^9$ comprises methyl. In a further aspect, each of $R^7$, $R^8$, $R^9$, $R^{10}$, and $R^{11}$ is hydrogen.

In one aspect, $Q^1$ comprises optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, or optionally substituted heteroaryl.

In a further aspect, the compound has a structure represented by a formula:

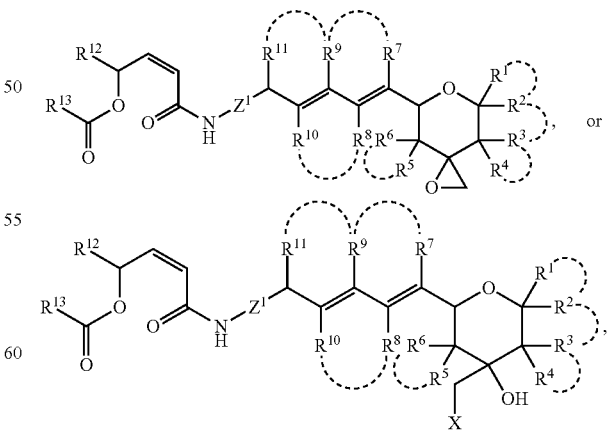

wherein $R^{12}$ and $R^{13}$ independently comprises hydrogen or optionally substituted organic residue comprising from 1 to 16 carbons;

In one aspect, $R^{13}$ comprises hydrogen, methyl, ethyl, propyl, butyl, amino, optionally substituted organic alkoxy, amino alkyl, heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, or optionally substituted heteroaryl. In a further aspect, $R^{13}$ comprises alkylamino, dialkylamino, or cycloalkylamino comprising from 1 to 12 carbons. In a specific aspect, $R^{13}$ comprises optionally substituted piperazinyl.

In a further aspect, $R^{13}$ comprises a substituent having a structure represented by the formula:

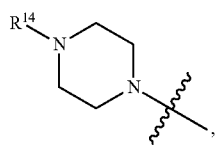

wherein $R^{14}$ comprises alkyl, heteroalkyl, cycloalkyl, or heterocycloalkyl.

In a still further aspect, $R^{14}$ can be optionally substituted methyl, ethyl, propyl, butyl, cyclobutyl, cyclopentyl, and cyclohexyl.

In one aspect, $R^{12}$ comprises hydrogen, optionally substituted methyl, ethyl, propyl, butyl, pentyl, or hexyl.

In a further aspect, the compound comprises a structure represented by a formula:

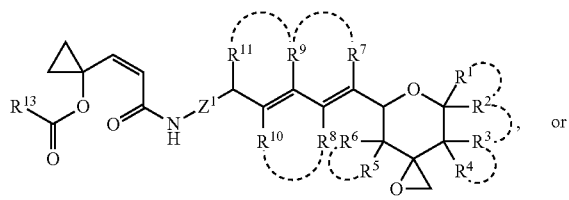

or

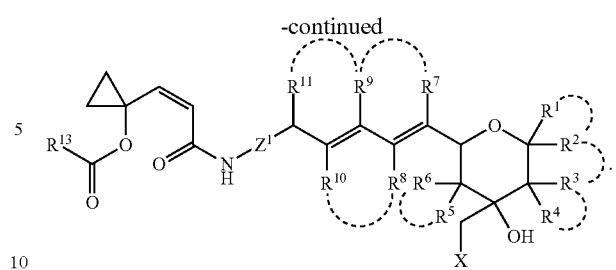

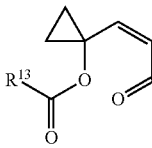

In a still further aspect, both $R^{12}$ and $R^{13}$ independently comprise methyl.

In one aspect, $Z^1$ comprises optionally substituted cycloalkyl or cycloalkenyl or cycloalkynyl, an optionally substituted heterocycloalkyl or heterocycloalkenyl or heterocycloalkynyl, or optionally substituted aryl, or optionally substituted heteroaryl. In a further aspect, $Z^1$ comprises an optionally substituted cyclopropyl, cyclobutyl, cyclopentyl, cyclohexyl, cycloheptyl, heterocyclopropyl, heterocyclobutyl, heterocyclopentyl, heterocyclohexyl, heterocycloheptyl, furan, pyran, oxole, oxazine, thiophene, thioazole, oxathiolane, pyrrolidine, pyrazolidine, imidazolidine, triazolidine, perhydropyridine, azole, morpholine, pyridine, pyrimidine, or benzene.

In a further aspect, $Z^1$ has a structure represented by a formula:

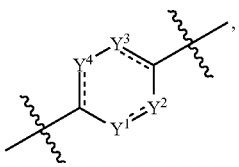

wherein $Y^1, Y^2, Y^3$, and $Y^4$ independently comprises oxygen, optionally substituted carbon, or optionally substituted nitrogen with a structure represented by the formula, $NR^{14}R^{15}$, wherein $R^{14}$ and $R^{15}$ independently comprises hydrogen or optionally substituted alkyl comprising from 1 to 4 carbons; and wherein ----- is an optional bond.

In one aspect, the compound can be present as:

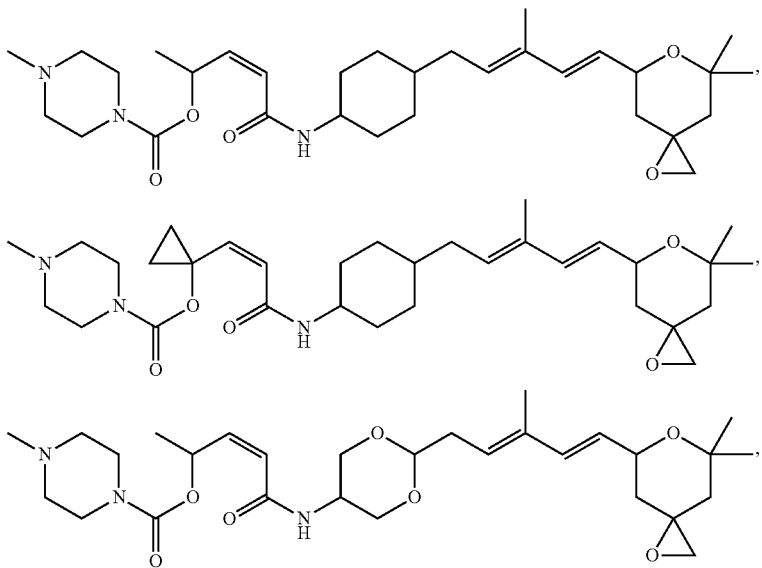

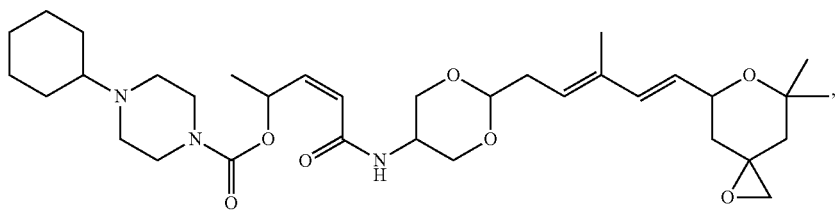
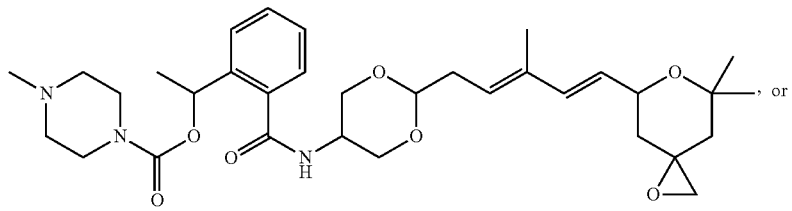
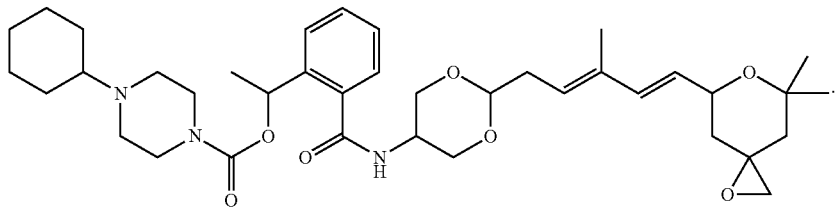
In a specific aspect, the compound can be present as:
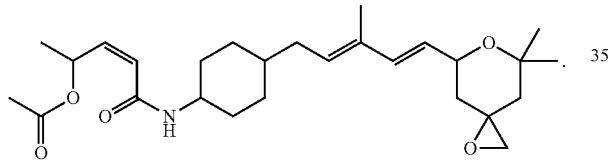
In one aspect, the compound comprises a single diastereomer. For example, the compound can be substantially enantiopure.
In a further aspect, the compound can have a structure represented by a formula selected from:
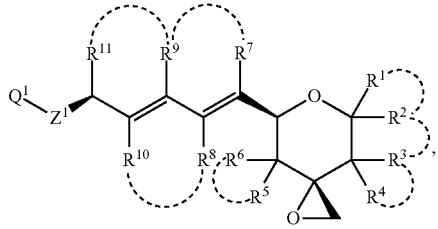
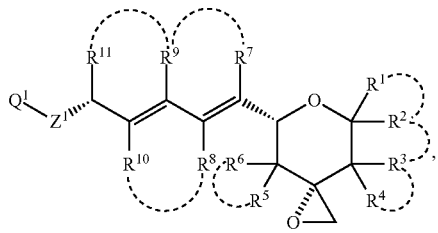
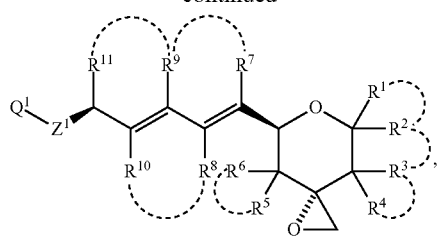
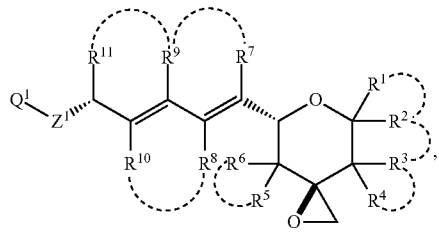
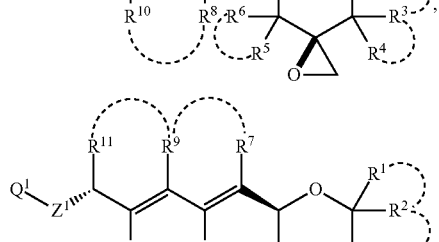
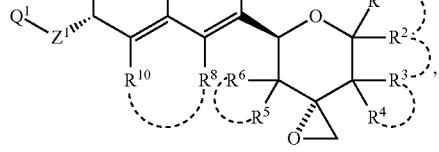

-continued

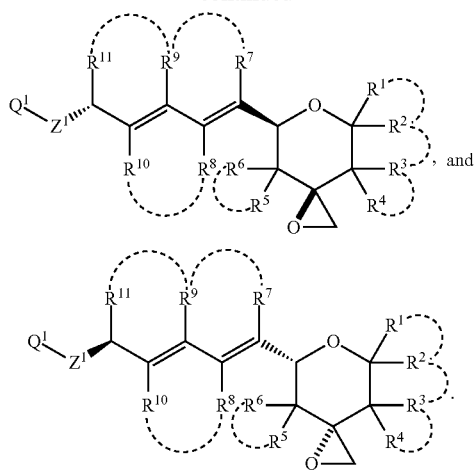

In a specific aspect, the compound can have a structure represented by the formula:

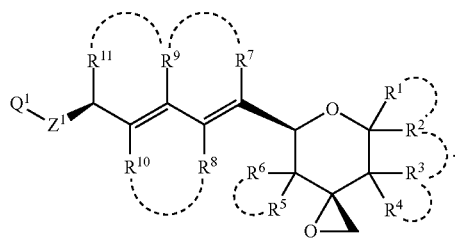

In one aspect, $Q^1$ has a structure represented by a formula selected from:

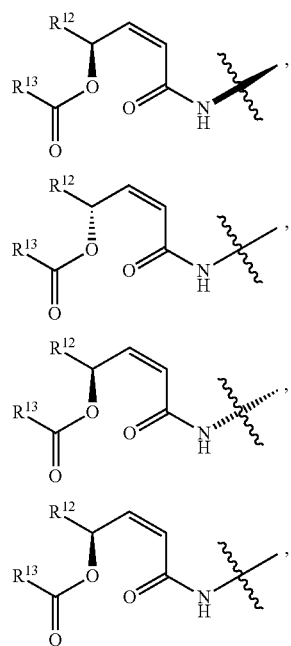

-continued

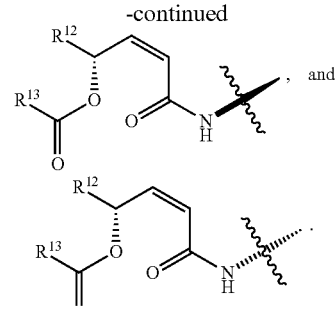

In a further aspect, $Q^1$ has a structure represented by a formula selected from:

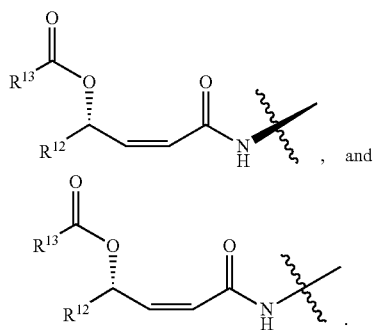

In one aspect, the compound can have a structure represented by the formula:

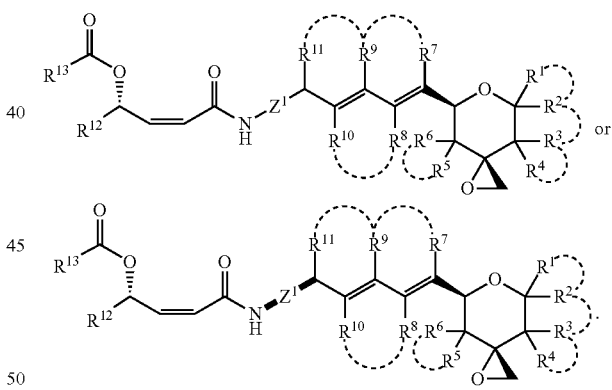

In this aspect, $R^1$ and $R^2$ can be methyl, and each of $R^3$, $R^4$, $R^5$, and $R^6$ can be hydrogen. In a further example of this aspect, $R^9$ can be methyl.

In a further aspect, the compound has a structure represented by the formula:

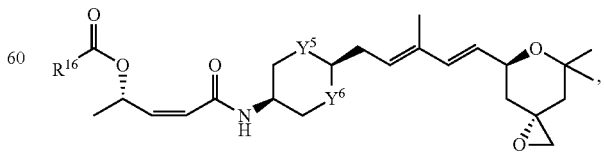

wherein $Y^5$ and $Y^6$ independently represent O or $CH_2$; and wherein $R^{16}$ represents optionally substituted $C_1$-$C_4$ alkyl, optionally substituted aryl, optionally substituted heteroaryl, optionally substituted cycloalkyl, or optionally substituted heterocycloalkyl.
Exemplary compounds within this formula include without limitation the following compounds:
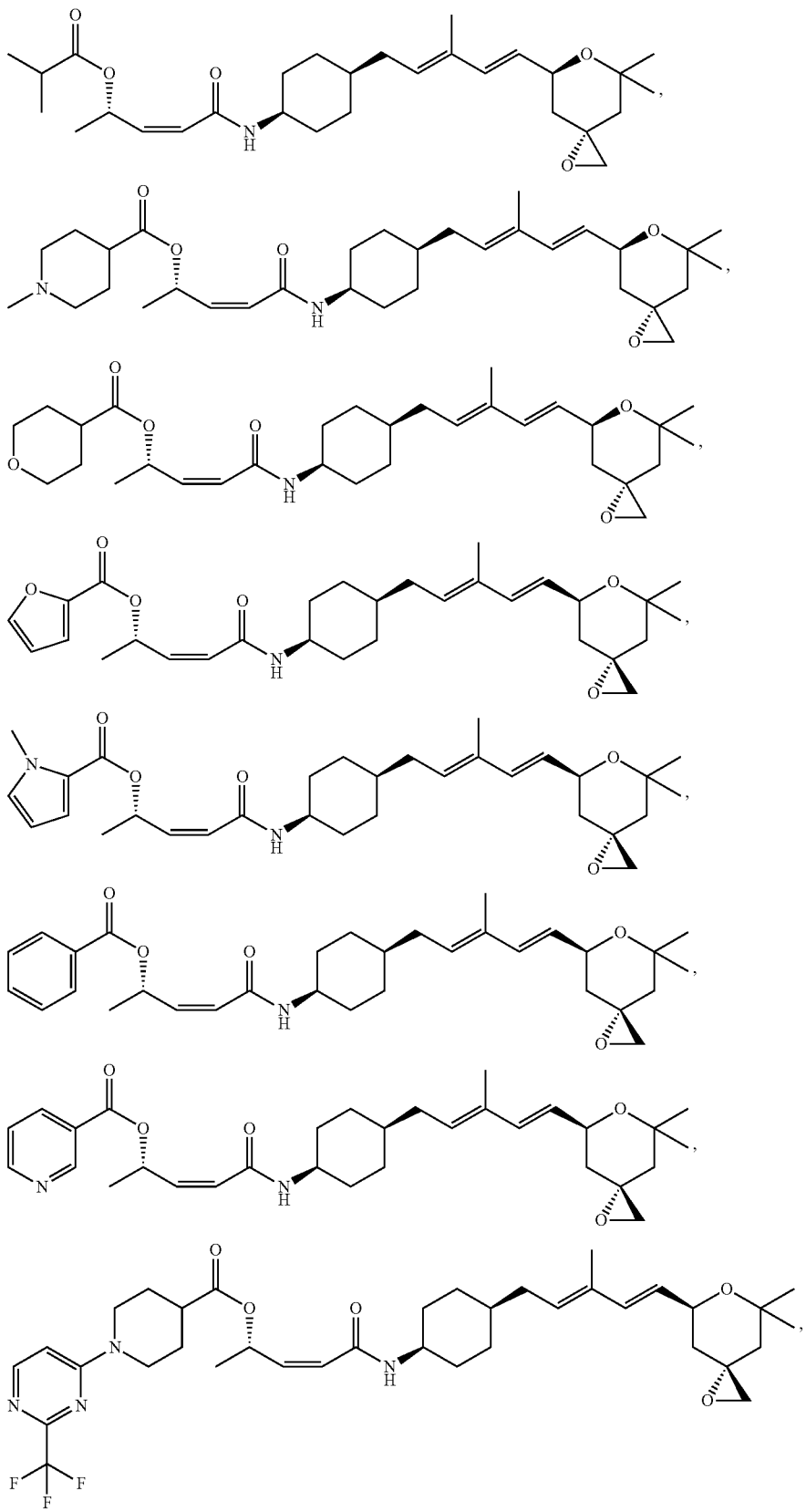

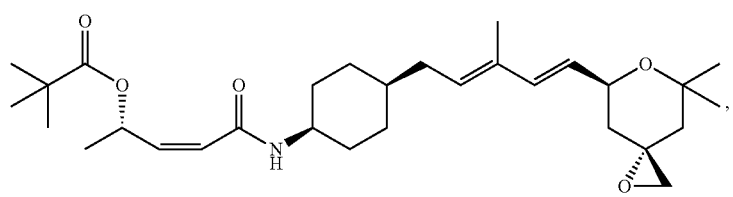
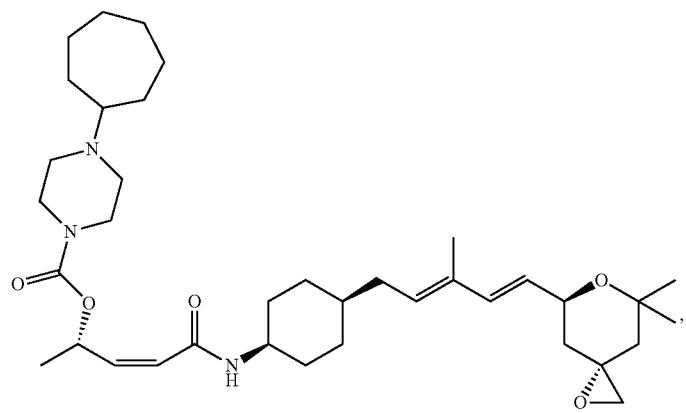
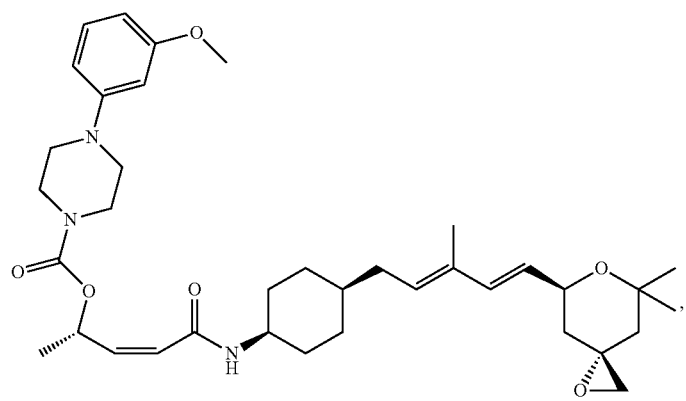
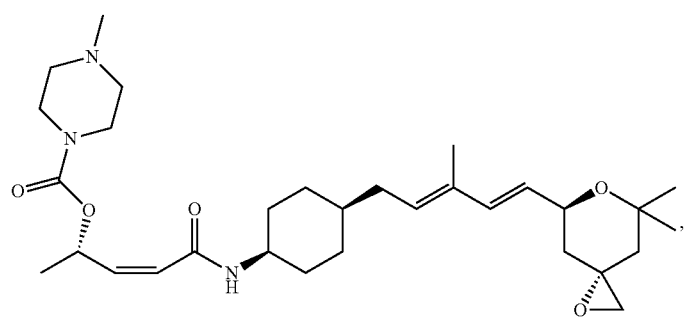
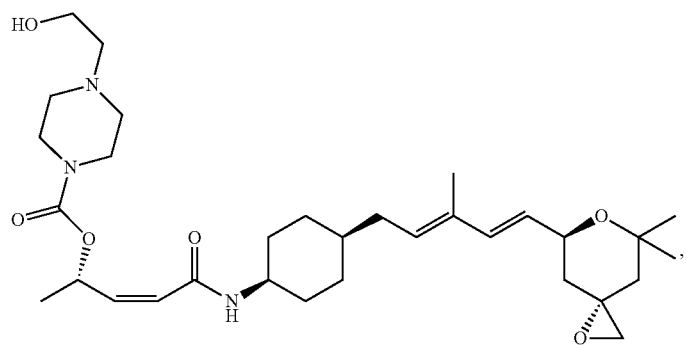

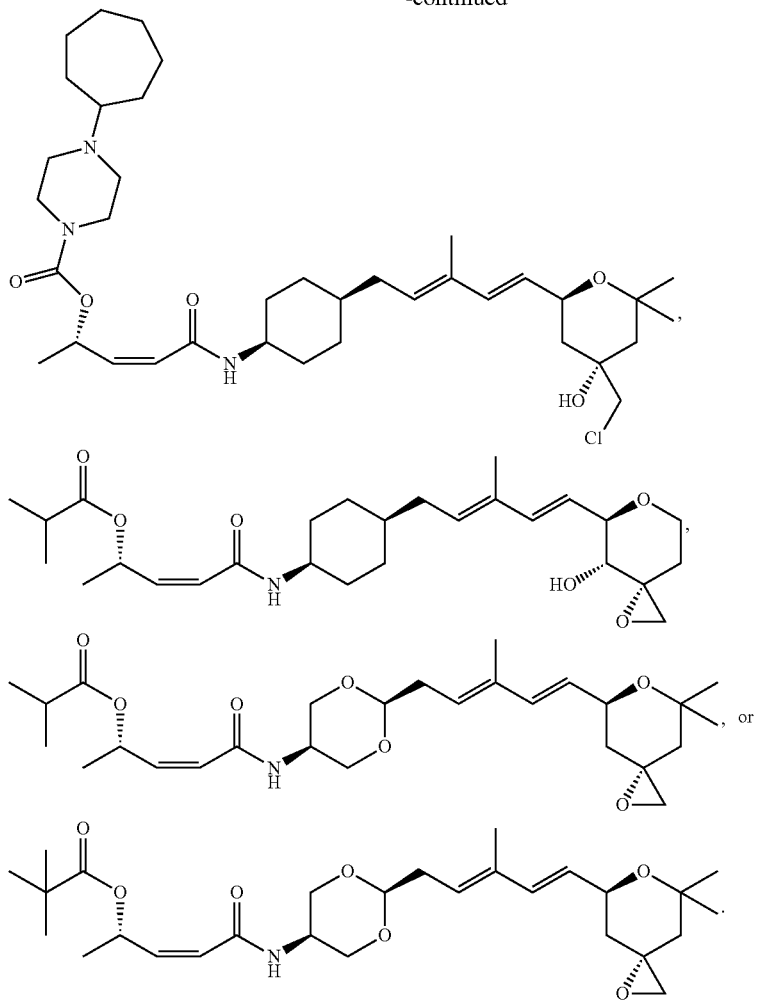

In a further aspect, the compound has a structure represented by the formula:

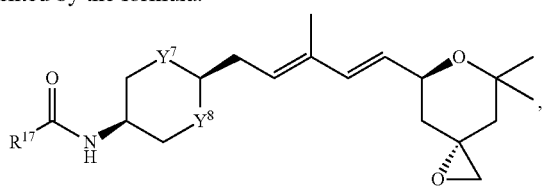

wherein $Y^7$ and $Y^8$ independently represent O or $CH_2$; and wherein $R^{17}$ represents optionally substituted $C_1$-$C_4$ alkyl.

Exemplary compounds within this formula include without limitation:

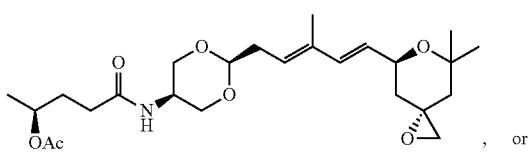

-continued

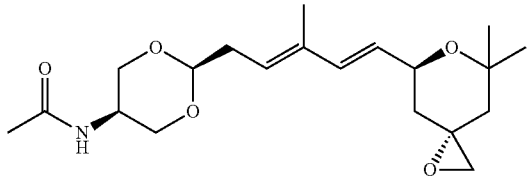

For any compound comprising a single diastereomer or enantiomer, as disclosed herein, $Z^1$ can comprise a 1,4-cyclohexane residue. For example, a compound can have a structure represented by the formula:

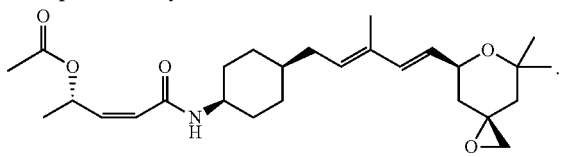

In a further aspect, the compound can be present as:

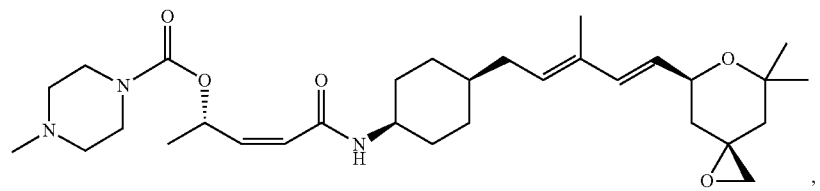

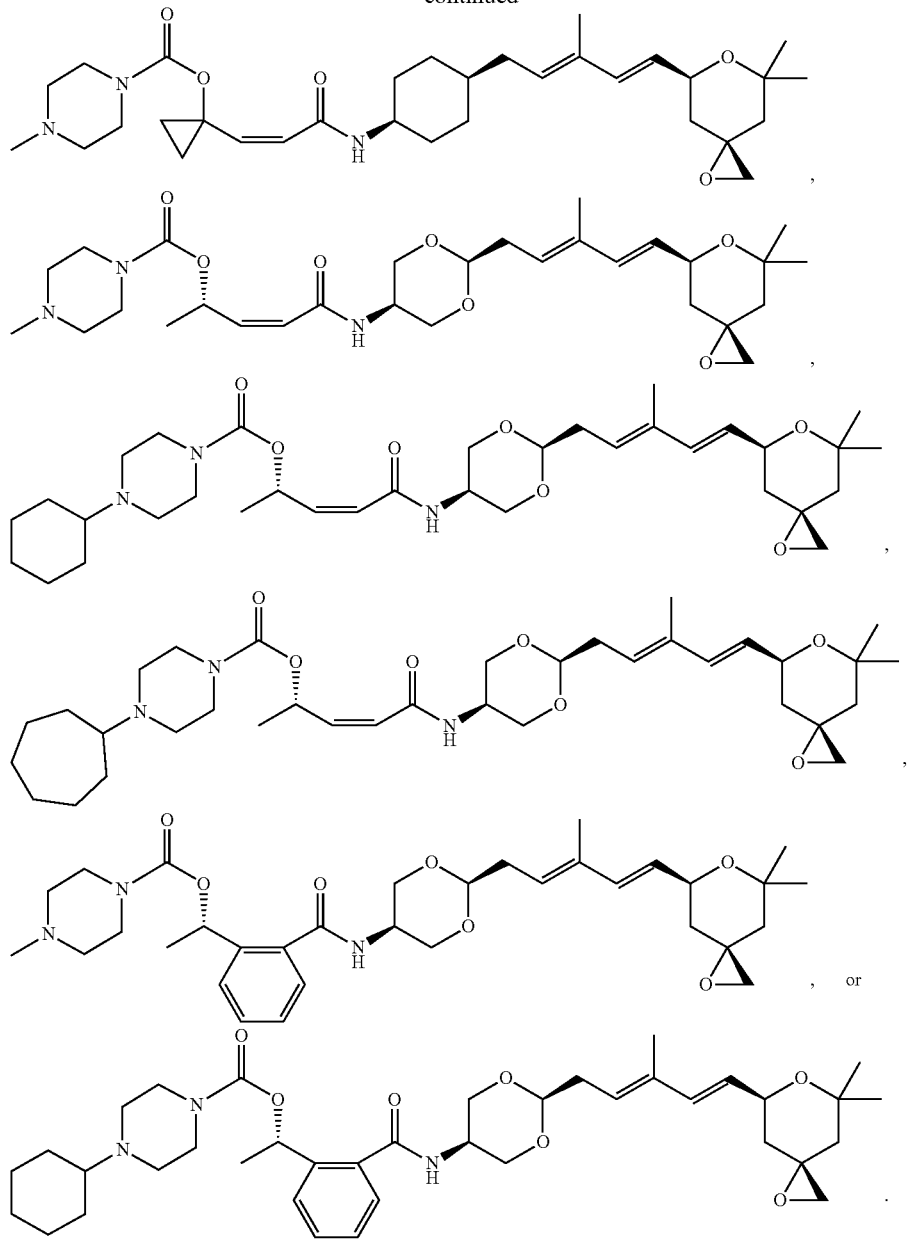

In a still further aspect, the compound can be present as: (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl acetate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl acetate; (S,Z)-5-((2R,5R)-5-((2E,4E)-5-((3R,5S)-7,7-dimethyl-1,6-dioxaspiro[2.5]octan-5-yl)-3-methylpenta-2,4-dienyl)-1,3-dioxan-2-ylamino)-5-oxopent-3-en-2-yl acetate; (S)-1-(2-((1R,4R)-4-((2E,4E)-5-((3R,5S)-7,7-dimethyl-1,6-dioxaspiro[2.5]octan-5-yl)-3-methylpenta-2,4-dienyl)cyclohexylcarbamoyl)phenyl)ethyl acetate; (S)-1-(2-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylcarbamoyl)phenyl)ethyl acetate; (S)-1-(2-((2R,5R)-5-((2E,4E)-5-((3R,5S)-7,7-dimethyl-1,6-dioxaspiro[2.5]octan-5-yl)-3-methylpenta-2,4-dienyl)-1,3-dioxan-2-ylcarbamoyl)phenyl)ethyl acetate; (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl 4-methylpiperazine-1-carboxylate; 1-((Z)-3-((1R,4S)-4-((2E,4E)-5-((3R,5S)-7,7-dimethyl-1,6-dioxaspiro[2.5]octan-5-yl)-3-methylpenta-2,4-dienyl)cyclohexylamino)-3-oxoprop-1-enyl)cyclopropyl 4-methylpiperazine-1-carboxylate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl 4-methylpiperazine-1-carboxylate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl 4-cyclohexylpiperazine-1-carboxylate; and (S)-1-(2-((2R,5R)-2-((2E,4E)-5-((3R,5S)-7,7-dimethyl-1,6-dioxaspiro[2.5]octan-5-yl)-3- methylpenta-2,4-dienyl)-1,3-dioxan-5-ylcarbamoyl)phenyl) ethyl 4-cyclohexylpiperazine-1-carboxylate.

In one aspect, a pyran derivative, as disclosed herein, can convert into a dioxaspiro derivative, as disclosed herein, which can be represented by the following reaction scheme:

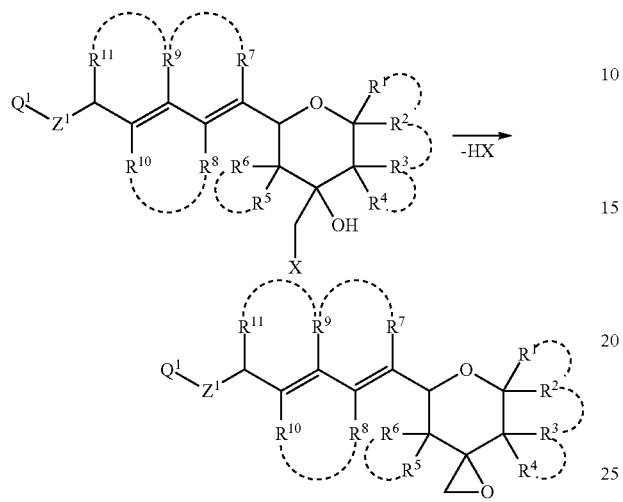

In a further aspect, a non-active pyran derivative can convert into an active dioxaspiro derivative. Thus, in this example, a pyran derivative, while not necessarily active, can function as a precursor, or prodrug, from which an active therapeutic agent can be generated.

It is understood that the compounds disclosed herein can be used in connection with the methods and compositions disclosed herein.

2. Anticancer Activity

The disclosed compounds can have anticancer activity, and thus can be effective at treating one or more cancers and/or related disorders. In one aspect, the compound is capable of inhibiting the proliferation of at least one cell (e.g., a cancer cell). A disclosed compound can also be cytotoxic against at least one cancer cell line (e.g, a lymphoma cell line). For example, the compound can be effective at treating overproliferation of a lymphoma cell line such as Jeko-1 or JVM-2.

The disclosed compounds can be efficacious against a variety of cancer and related cell lines. In one aspect, the disclosed compounds can be used to treat lymphoma. If a cell line is selected from Jeko-1 and JVM-2, for example, a compound disclosed herein can exhibit an $IC_{50}$ value of about 40, 50, 60, 70, 80, 90, or 100 nM against the cell line. In one aspect, the compound exhibits an $IC_{50}$ value of about 100 nM against a lymphoma cell line.

In a further aspect, based on a pharmacophore analysis, the compounds disclosed herein can act in a similar fashion as pladienolide series and/or FR series compounds. For example, a disclosed compound can be efficacious against a cancer cell line that a PD series and/or FR series compound is also efficacious against.

D. Methods of Making the Compounds

Certain materials, compounds, compositions, and components disclosed herein can be obtained commercially or synthesized using techniques generally known to those of skill in the art or by methods disclosed herein. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Disclosed herein is a method of making a spiro epoxide derivative, comprising the steps of: (a) providing a compound having a structure represented by the formula:

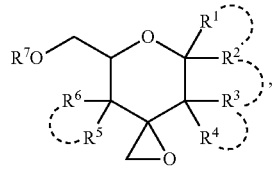

wherein each of $R^1$, $R^2$, $R^3$, $R^4$, $R^5$, $R^6$, and $R^7$ independently comprises halide, hydrogen, hydroxyl, amino, thiol, or optionally substituted organic residue comprising from 1 to 6 carbons; wherein each ----- is an optional covalent bond; and (b) performing an oxidation reaction to provide the a spiro epoxide derivative.

As used herein, the term "spiro epoxide," is intended to refer to the functional group:

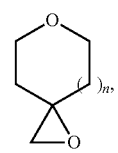

wherein n is an integer from 0-3. Thus, a spiro epoxide derivative can be a compound comprising the aforementioned spiro epoxide functional group. It is understood that a spiro epoxide is a subset of an "aspiro" compound, which comprises at least two rings, wherein two joined rings share only one common atom.

In one aspect, the provided spiro epoxide derivative has a structure represented by a formula:

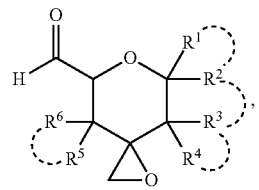

wherein each of $R^1$, $R^2$, $R^3$, $R^4$, $R^5$, and $R^6$ independently comprises halide, hydrogen, hydroxyl, amino, thiol, or optionally substituted organic residue comprising from 1 to 6 carbons, with the proviso that $R^5$ and $R^6$ are not hydroxyl or alkoxyl; wherein each ----- is an optional covalent bond.

In a further aspect, the step of providing a compound having a structure represented by a formula:

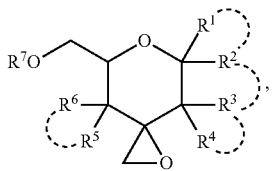

comprises the step of reducing a compound having a structure represented by a formula:

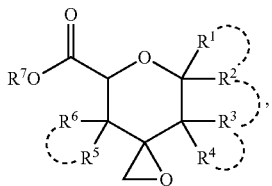

wherein each of $R^1$, $R^2$, $R^3$, $R^4$, $R^5$, $R^6$, and $R^7$ independently comprises halide, hydrogen, hydroxyl, amino, thiol, or an optionally substituted organic residue comprising from 1 to 6 carbons, with the proviso that $R^5$ and $R^6$ are not hydroxyl or alkoxyl; wherein each ----- is an optional covalent bond.

In one aspect, disclosed is a stereoselective method of making a pyranone derivative, comprising the steps of: providing a pyran carboxylate derivative having a structure represented by the formula:

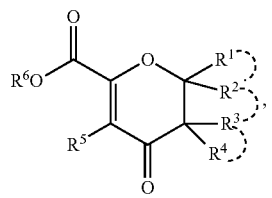

wherein each of $R^1$, $R^2$, $R^3$, $R^4$, $R^5$, $R^6$, and $R^7$ independently comprises halide, hydrogen, hydroxyl, amino, thiol, or an optionally substituted organic residue comprising from 1 to 6 carbons; wherein each ----- is an optional covalent bond; and performing an addition reaction to provide the pyranone derivative.

In a further aspect, disclosed is a method for making a compound comprising anticancer activity comprising the step of reacting a spiro epoxide derivative comprising a structure represented by a formula:

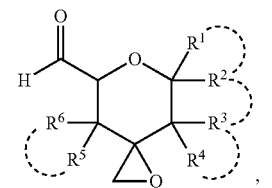

wherein each of $R^1$, $R^2$, $R^3$, $R^4$, $R^5$, and $R^6$ independently comprises halide, hydrogen, hydroxyl, amino, thiol, or optionally substituted organic residue comprising from 1 to 6 carbons, with the proviso that $R^5$ and $R^6$ are not hydroxyl or alkoxyl; wherein each ----- is an optional covalent bond; with a compound comprising a structure represented by a formula:

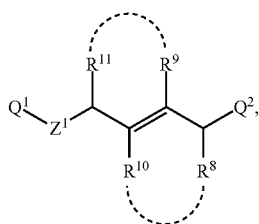

wherein $R^8$, $R^9$, $R^{10}$, and $R^{11}$ independently comprises halide, hydrogen, hydroxyl, amino, thiol, or optionally substituted organic residue comprising from 1 to 6 carbons; wherein $Z^1$ comprises an optionally substituted 3, 4, 5, 6, or 7 membered ring with no more than three chiral centers; wherein $Q^1$ comprises an optionally substituted organic residue comprising from 1 to 26 carbons; and wherein $Q^2$ comprises a sulfonyl group; thereby making the spliceosome inhibitor.

An exemplary, non-limiting approach to synthetic analogues having a structure represented by a formula:

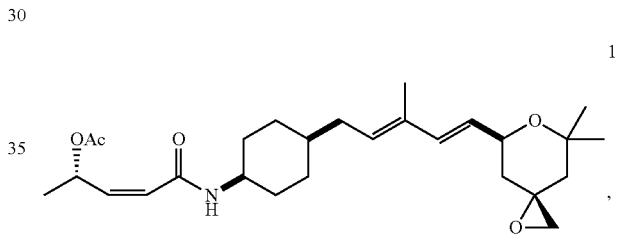

is represented by Scheme 1.

It was found that compound 4 could be a starting material for the left hand portion for various synthetic targets. Appropriate MacMillan conditions (Tuttle, J. B.; Ouellet, S. G.; MacMillan, D. W. C. "Organocatalytic Transfer Hydrogenation of Cyclic Enones." Journal of the American Chemical Society 2006, 128, 12662-12663), can give the desired product 5. Intermediate 6 can allow for the setting of two of three chiral centers in enantiomerically pure targets and can be appropriately functionalized for conversion to various final targets disclosed herein by reduction to give alcohol 7, which in turn can be oxidized to aldehyde 8.

The synthesis of the compounds disclosed herein comprising alkenyl linkers can be accomplished starting with the aldehyde 9 derived from the commercially available cis-cyclohexane derivative 8, followed by homologation to give trans alcohol 10. The product of this reaction can be converted to a corresponding 2-thiobenzthioazole derivative 11 using Mitsunobu conditions (Mitsunobu, O. "The use of diethyl azodicarboxylate and triphenylphosphine in synthesis and transformation of natural products." Synthesis 1981, 1-28) and subsequently oxidized to a corresponding 2-sulfonylbenzothioazole derivative 12 (Motoyoshi, H.; Horigome, M.; Watanabe, H.; Kitahara, T. "Total synthesis of FR901464: second generation." Tetrahedron 2006, 62, 1378-1389).

Removal of any BOC group and coupling of the optically pure (S,Z)-4-(dimethyl-t-butylsilyloxy)pent-2-enoic acid (prepared according to the known procedure) (Motoyoshi, H.; Horigome, M.; Watanabe, H.; Kitahara, T. "Total synthesis of FR901464: second generation. Tetrahedron 2006, 62, 1378-1389") can give the desired functionalized amide 13. Coupling of this reagent with epoxy aldehyde 7, followed by deprotection and acylation can give various target compounds.

Scheme 1

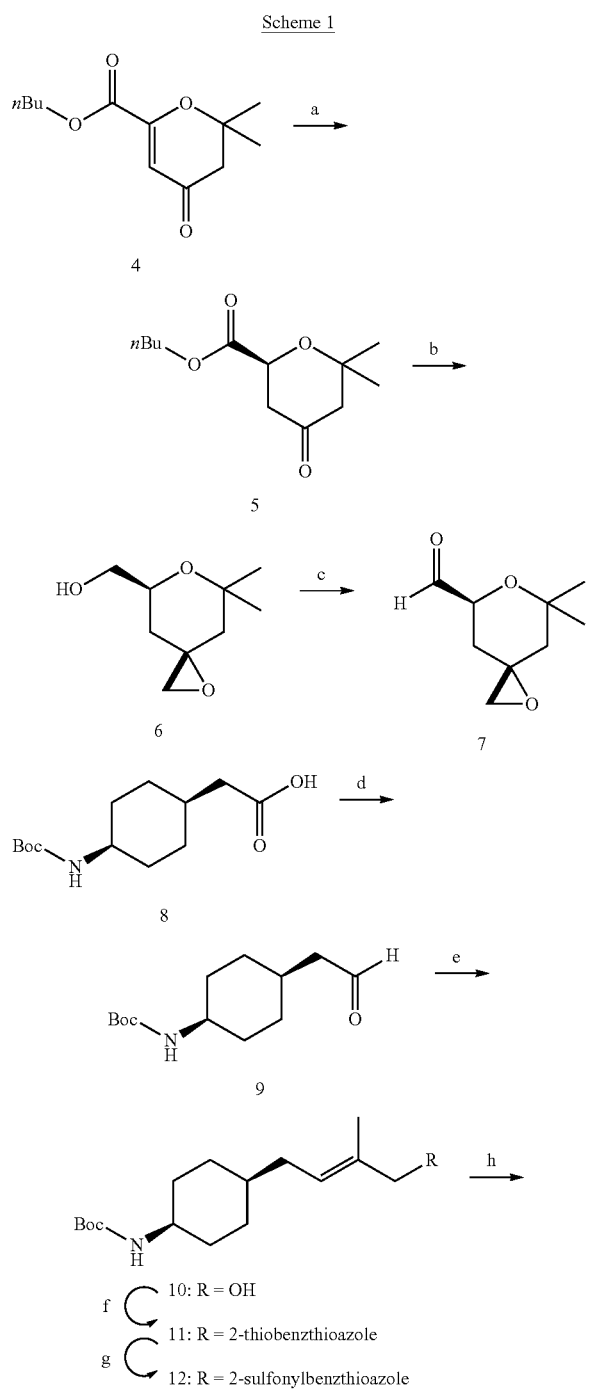

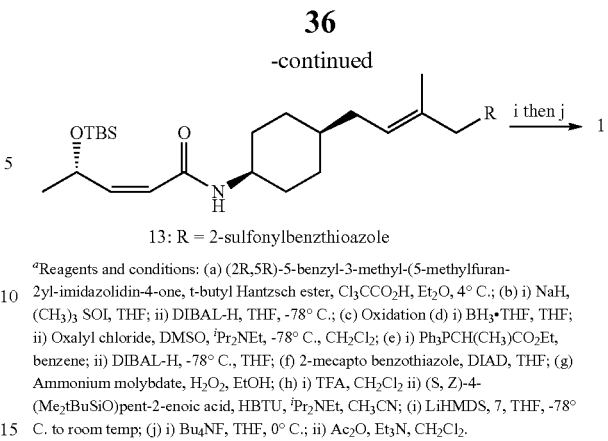

13: R = 2-sulfonylbenzthioazole

[a]Reagents and conditions: (a) (2R,5R)-5-benzyl-3-methyl-(5-methylfuran-2yl-imidazolidin-4-one, t-butyl Hantzsch ester, Cl₃CCO₂H, Et₂O, 4° C.; (b) i) NaH, (CH₃)₃ SOI, THF; ii) DIBAL-H, THF, -78° C.; (c) Oxidation (d) i) BH₃•THF, THF; ii) Oxalyl chloride, DMSO, ⁱPr₂NEt, -78° C., CH₂Cl₂; (e) i) Ph₃PCH(CH₃)CO₂Et, benzene; ii) DIBAL-H, -78° C., THF; (f) 2-mecapto benzothiazole, DIAD, THF; (g) Ammonium molybdate, H₂O₂, EtOH; (h) i) TFA, CH₂Cl₂ ii) (S, Z)-4-(Me₂tBuSiO)pent-2-enoic acid, HBTU, ⁱPr₂NEt, CH₃CN; (i) LiHMDS, 7, THF, -78° C. to room temp; (j) i) Bu₄NF, THF, 0° C.; ii) Ac₂O, Et₃N, CH₂Cl₂.

It will be apparent that various modifications to the compounds and steps listed in Schemes 1 can be carried out, and that a similar synthetic approach, for example, can be readily adapted to produce a variety of compounds disclosed herein Also disclosed herein is the product of any disclosed methods.

It should also be understood that the synthetic methods disclosed herein can be used in connection with the compounds, compositions, and methods disclosed herein. Thus, the synthetic methods disclosed herein can be used to make the compounds disclosed herein.

E. Pharmaceutical Compositions

Also disclosed are pharmaceutical compositions, including dosage forms, comprising one or more disclosed compounds. The disclosed compounds can be administered alone or in combination with pharmaceutically acceptable carriers or excipients, in either single or multiple doses. The pharmaceutical compositions can be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, Pa., 1995.

In one aspect, a dosage form can comprise a therapeutically effective amount of at least one product of the synthetic methods disclosed herein. In a further aspect, a dosage form for administration to a subject can comprise a therapeutically effective amount of any compound disclosed herein and a pharmaceutically acceptable carrier. In a specific aspect, the dosage form can comprise a therapeutically effective amount that can be effective for a mammal, e.g., a human or a mouse.

In one aspect, the term "pharmaceutically acceptable" can mean approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions can contain a therapeutically effective amount of one or more spliceosome inhibitors preferably in purified form, together with a suitable amount of carrier so as to provide the form for proper administration to the patient. The formulation should typically suit the mode of administration.

In one aspect, a composition can be formulated in accordance with routine procedures as a pharmaceutical composition adapted for intravenous administration to humans. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The pharmaceutical compositions can be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, creams, gels, inhalants, dermal patches, implants etc.

For parenteral administration, solutions of the compounds in sterile aqueous solution, aqueous propylene glycol or sesame or peanut oil can be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

It is understood that the pharmaceutical compositions can be used in connection with the methods and compounds disclosed herein.

F. Methods of Using the Compounds and Compositions

1. Treatment of a Disorder

Diseases and disorders involving uncontrolled cellular proliferation or cell overproliferation that can be treated or prevented include but are not limited to, cancers, premalignant conditions (e.g., hyperplasia, metaplasia, dysplasia), benign tumors, hyperproliferative disorders, and benign dysproliferative disorders. Cancer is characterized primarily by an increase in the number of abnormal cells derived from a given normal tissue, invasion of adjacent tissues by these abnormal cells, and lymphatic or blood-borne. Malignancies and related disorders that can be treated, prevented, managed, amerliorated, particularly metastatic cancer, by administration of a compound of the invention that inhibits ceramidase function as discussed below (for a review of such disorders, see Fishman et al., 1985, Medicine, 2d Ed., J. B. Lippincott Co., Philadelphia).

In one aspect, the disclosed compounds and/or compositions can be useful for the treatment of a cancer, including, but not limited to, Leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, curvical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. For a review of such disorders, see Fishman et al., 1985, Medicine, 2d Ed., J.B. Lippincott Co., Philadelphia).

In a further aspect, cancers and related disorders that can be treated or prevented by methods and compositions disclosed herein include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungaling (polypoid), ulcerating, superficial spreading, diffusely spreading, malignant lymphom, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

2. Determining a Therapeutically Effective Amount

Toxicity and therapeutic efficacy of the disclosed compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices can be desirable. While compounds that exhibit toxic side effects can be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds lies preferably within a range of circulating concentrations that include the $ED_{50}$ with little or no toxicity. Dosages can vary within this range depending upon the dosage form employed and the route of administration utilized. For any compound used in disclosed herein, the therapeutically effective dose can be estimated initially from cell culture assays. A dose can be formulated in animal models to achieve a circulating plasma concentration range that includes the $IC_{50}$ as determined in cell culture experiments. Such information can be used to more accurately determine useful doses in humans. Levels in plasma can be measured, for example, by high performance liquid chromatography.

Suitable daily doses for the treatment or prevention of a disorder described herein can be readily determined by those skilled in the art. A recommended dose of a compound of a compound disclosed herein can be from about 0.1 mg to about 1000 mg per day, e.g., from about 0.1 to about 500 mg/kg/day, 0.1 to about 250 mg/kg/day, or 0.1 to about 100 mg/kg/day, per kg of body weight, given as a single dose, a single once-a-day dose, or as divided doses throughout a selected time period.

The anti-cancer activity of the disclosed therapies can be determined by using various experimental animal models of such as the scid mouse model or nude mice with human tumor grafts known in the art and described in Yamanaka, 2001, Microbiol Immunol 2001; 45 (7): 507-14.

The disclosed protocols and compositions can be tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which a patient tissue sample is grown in culture, and exposed to or otherwise administered a protocol, and the effect of such protocol upon the tissue sample is observed.

A lower level of proliferation or survival of the contacted cells can indicate that the therapy can be effective to treat a selected disorder in a subject. Alternatively, instead of culturing cells from a patient, protocols can be screened using cells of a tumor or malignant cell line. Many assays known in the art can be used to assess such survival and/or growth; for example, cell proliferation can be assayed by measuring 3H-thymidine incorporation, by direct cell count, by detecting changes in transcriptional activity of known genes such as proto-oncogenes or cell cycle markers; cell viability can be assessed by trypan blue staining, while differentiation can be assessed visually based on changes in morphology, etc.

Compounds for use in therapy can be tested in suitable animal model systems prior to testing in humans, including but not limited to in rats, mice, chicken, cows, monkeys, rabbits, etc. The principle animal models for cancer known in the art and widely used include mice, such as described in Hann et al., 2001, Curr Opin Cell Biol 2001, 13 (6): 778-84, which is incorporated herein by reference in its entirety.

Further, any assays known to those skilled in the art can be used to evaluate the prophylactic and/or therapeutic utility of the combinatorial therapies disclosed herein for treatment, prophylaxis, management or amelioration of one or more symptoms associated with the disease or disorder as described hereinabove.

3. Co-therapeutic Use

In one aspect, other cancer treatments can be used in combination with the administration of one or more compounds disclosed herein. Such treatments include the use of one or more molecules, or compounds for the treatment of cancer (i.e., cancer therapeutics). Some examples include, but are not limited to, chemoagents, immunotherapeutics, cancer vaccines, anti-angiogenic agents, cytokines, hormone therapies, gene therapies, biological therapies, and radiotherapies. While maintaining or enhancing efficacy of treatment, preferably the methods of the present invention increase patient compliance, improve therapy and/or reduce unwanted or adverse effects.

In one aspect, the methods of the invention includes the administration of one or more angiogenesis inhibitors such as but not limited to: Angiostatin (plasminogen fragment); anti-angiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placenta ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Additional examples of anti-cancer agents that can be used in the various aspects disclosed herein, including pharmaceutical compositions and dosage forms disclosed herein, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin. These two agents are particularly useful when used in methods employing thalidomide and a topoisomerase inhibitor.

In a further aspect, the treatment methods disclosed herein includes the administration of one or more immunotherapeutic agents, such as antibodies and immunomodulators, which include, but are not limited to, HERCEPTINS, RITUXANS, OVAREX™, PANOREX@, BEC2, IMC-C225, VITAMIN, CAMPATH@ I/H, Smart MI95, LYMPHOCIDE™, Smart I D10, and ONCOLYM™, rituximab, gemtuzumab, or trastuzumab.

In a still further aspect, the treatment methods disclosed herein includes administering one or more anti-angiogenic agents, which include, but are not limited to, angiostatin, thalidomide, kringle 5, endostatin, other Serpins, anti-thrombin, 29 kDa N-terminal and 40 kDa C-terminal proteolytic fragments of fibronectin, 16 kDa proteolytic fragment of prolactin, 7.8 kDa proteolytic fragment of platelet factor-4, a 13-amino acid peptide corresponding to a fragment of platelet factor-4 (Maione et al., 1990, Cancer Res. 51: 2077), a 14-amino acid peptide corresponding to a fragment of collagen I<BR> <BR> (Tolma et al., 1993, J. Cell Biol. 122: 497), a 19 amino acid peptide corresponding to a <BR> fragment of Thrombospondin I (Tolsma et al., 1993, J. Cell Biol. 122: 497), a 20-amino acid peptide corresponding to a fragment of SPARC (Sage et al., 1995, J. Cell. Biochem. 57: 1329-), or any fragments, family members, or derivatives thereof, including pharmaceutically acceptable derivatives thereof.

In one aspect, the treatment methods disclosed herein can comprise the use of radiation.

In a further aspect, the treatment methods further comprises the administration of one or more cytokines, which includes, but is not limited to, lymphokines, tumor necrosis factors, tumor necrosis factor-like cytokines, lymphotoxin-a, lymphotoxin-b, interferon-a, interferon-b, macrophage inflammatory proteins, granulocyte monocyte colony stimulating factor, interleukins (including, but not limited to, interleukin-1, interleukin-2, interleukin-6, interleukin-12, interleukin-15, interleukin-18), OX40, CD27, CD30, CD40 or CD137 ligands, Fas-Fas ligand, 4-1BBL, endothelial monocyte activating protein or any fragments, family members, or derivatives thereof, including pharmaceutically acceptable salts thereof.

In a further aspect, the treatment method comprises hormonal treatment. Hormonal therapeutic treatments comprise hormonal agonists, hormonal antagonists (e.g., flutamide, tamoxifen, leuprolide acetate (LUPRON™), LH-RH antagonists), inhibitors of hormone biosynthesis and processing, steroids (e.g., dexamethasone, retinoids, betamethasone, cortisol, cortisone, prednisone, dehydrotestosterone, glucocorticoids, mineralocorticoids, estrogen, testosterone, progestins), antigestagens (e.g., mifepristone, onapristone), antiandrogens (e.g., cyproterone acetate), and the like.

In a further aspect, the disclosure also relates to kits comprising at least one disclosed compound and one or more other therapeutically active compounds, which are usually applied in the treatment of the above mentioned conditions. For example, the disclosed kits can comprise therapeutically effective amounts of one or more disclosed compound and one or anti-cancer agents. The kits can be co-packaged, co-formulated, and/or co-delivered with the anti-cancer agents. For example, a drug manufacturer, a drug reseller, a physician, or a pharmacist can provide a disclosed kit for delivery to a patient.

4. Prophylactic Treatment

In a further aspect, the disclosed compounds, compositions, and methods can be used prophylactically, i.e., to prevent progression to a neoplastic or malignant state, including but not limited to those disorders listed above. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

5. Subjects

The compounds, compositions, and methods disclosed herein can be useful for the treatment or prevention of one or more disorders associated with cell splicing in a subject, as discussed hereinabove. In general, a subject can be any age, including a fetus. A subject to which a compound or compositions disclosed herein can be administered can be an animal, including but not limited to a mammal, such as a non-primate mammal (e.g., cows, pigs, sheep, goats, horses, chickens, dogs, rats, etc.) and a primate (e.g., a monkey such as a acynomolgous monkey and a human). A subject can also be a laboratory animal (e.g, a mouse, rabbit, guinea pig, fruit fly, etc.).

In one aspect, a subject can be diagnosed with one or more disorders as discussed herein elsewhere. In a specific aspect, a subject can be diagnosed with one or more disorders as discussed herein elsewhere before the step of administering to the subject a therapeutically effective amount of one more compounds disclosed herein.

In a further aspect, a subject can be a subject in need of treatment for disorder of uncontrolled cellular proliferation, e.g., cancer. In a still further aspect, a subject can have cancer or a related disorder, as discussed hereinbefore. In one aspect, a subject can be treated prophylactically with a compound or composition disclosed herein, as discussed herein elsewhere.

One or more compounds or compositions disclosed herein can be utilized for the prevention of a variety of cancers, e.g., in individuals who are predisposed as a result of familial history or in individuals with an enhanced risk to cancer due to environmental factors.

The methods and compositions of the invention can be used in patients who are treatment naive, in patients who have previously received or are currently receiving treatment with other pharmaceutical agents or combinations, including but not limited to anti-cancer agents. Other subjects can include patients that have metastasis or no metastasis.

The methods and compositions of the invention are useful not only in untreated patients but are also useful in the treatment of patients partially or completely un-responsive to other treatments. In various aspects, the disclosure provides methods and compositions useful for the treatment of diseases or disorders in patients that have been shown to be or can be refractory or non-responsive to therapies comprising the administration of other agents.

In one aspect, subjects that can be treated with the compositions disclosed herein include those subjects displaying the presence of one or more characteristics of a transformed phenotype, or of a malignant phenotype, displayed in vivo or displayed in vitro by a cell sample from a subject, can indicate the desirability of prophylactic/therapeutic administration of a compound or composition disclosed herein. As mentioned hereinabove, such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc.

In a further aspect, a subject that exhibits one or more of the following predisposing factors for malignancy can be treated by administration of an effective amount of a compound disclosed herein: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), and a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112-113) etc.)

6. Manufacture of a Medicament

Also provided is a method for the manufacture of a medicament for treatment of a disorder in a subject (e.g., a mammal), for modulating spliceosome activity, comprising combining at least one compound having a structure represented by a formula:

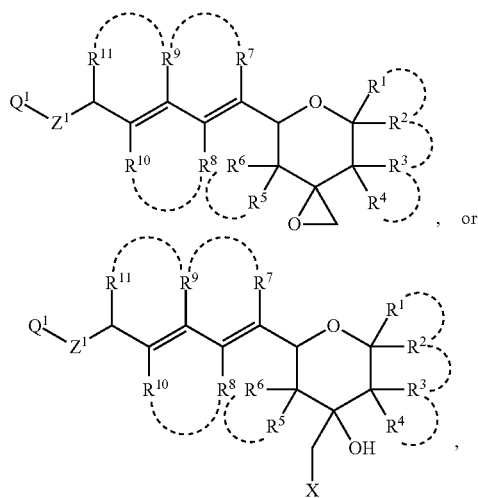

wherein each of $R^1$, $R^2$, $R^3$, $R^4$, $R^5$, and $R^6$ independently comprises halide, hydrogen, hydroxyl, amino, thiol, or optionally substituted organic residue comprising from 1 to 6 carbons; wherein each of $R^7$, $R^8$, $R^9$, $R^{10}$, and $R^{11}$ independently comprises halide, hydrogen, hydroxyl, amino, thiol, or optionally substituted organic residue comprising from 1 to 6 carbons; and wherein each ----- is an optional covalent bond; and wherein X is a leaving group; wherein $Z^1$ comprises an optionally substituted 3, 4, 5, 6, or 7 membered ring; wherein if $R^5$ or $R^6$ is hydroxyl or alkoxyl, then $Z^1$ comprises a ring with no more than three chiral centers; and wherein $Q^1$ comprises an optionally substituted organic residue comprising from 1 to 26 carbons; or a pharmaceutically acceptable derivative thereof, with a pharmaceutically acceptable carrier.

In a further aspect, $Z^1$ comprises a ring with no more than two chiral centers in the 3, 4, 5, 6, or 7 membered ring. For example, $Z^1$ can have two chiral centers in the 3, 4, 5, 6, or 7 membered ring. In a specific aspect, $Z^1$ can have two chiral centers in the 6 membered ring.

In a further aspect, neither $R^5$ nor $R^6$ comprises hydroxyl. In a still further aspect, at least one of $R^5$ and $R^6$ comprises hydroxyl.

In one aspect, $Z^1$ comprises a ring with no more than three stereocenters. In a further aspect, $Z^1$ comprises a ring that can include but is not limited to:

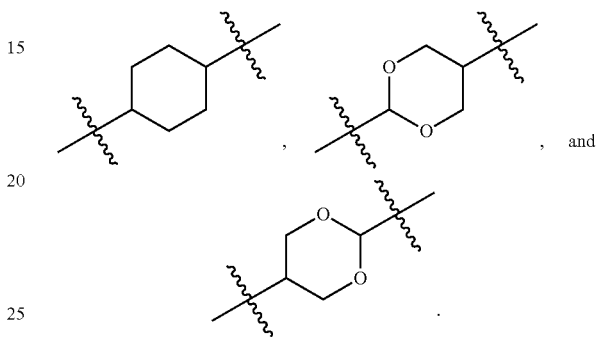

In a further aspect, $R^1$ and $R^2$ independently comprise hydroxyl, methyl, ethyl, propyl, or butyl, and $R^3$, $R^4$, $R^5$, and $R^6$ independently comprises hydrogen. In a still further aspect, both $R^1$ and $R^2$ independently comprise methyl. In one aspect, at least one of $R^1$ and $R^2$ comprises hydroxyl.

In one aspect, each of $R^7$, $R^8$, $R^9$, $R^{10}$, and $R^{11}$ independently comprises hydrogen or optionally substituted organic residue comprising from 1 to 4 carbons. In a specific aspect, $R^9$ comprises methyl. In a further aspect, each of $R^7$, $R^8$, $R^9$, $R^{10}$, and $R^{11}$ is hydrogen.

In one aspect, $Q^1$ comprises optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, or optionally substituted heteroaryl.

In a further aspect, the compound has a structure represented by a formula:

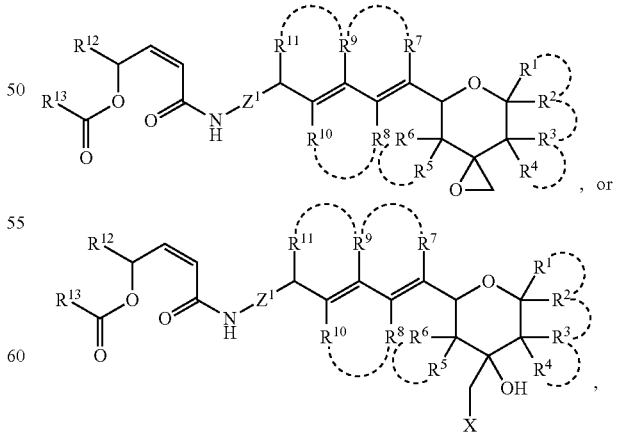

wherein $R^{12}$ and $R^{13}$ independently comprises hydrogen or optionally substituted organic residue comprising from 1 to 16 carbons;

In one aspect, $R^{13}$ comprises hydrogen, methyl, ethyl, propyl, butyl, amino, optionally substituted organic alkoxy, amino alkyl, heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, or optionally substituted heteroaryl. In a further aspect, $R^{13}$ comprises alkylamino, dialkylamino, or cycloalkylamino comprising from 1 to 12 carbons. In a specific aspect, $R^{13}$ comprises optionally substituted piperazinyl.

In a further aspect, $R^{13}$ comprises a substituent having a structure represented by the formula:

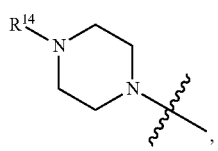

wherein $R^{14}$ comprises alkyl, heteroalkyl, cycloalkyl, or heterocycloalkyl.

In a still further aspect, $R^{14}$ can be optionally substituted methyl, ethyl, propyl, butyl, cyclobutyl, cyclopentyl, and cyclohexyl.

In one aspect, $R^{12}$ comprises hydrogen, optionally substituted methyl, ethyl, propyl, butyl, pentyl, or hexyl.

In a further aspect, the compound comprises a structure represented by a formula:

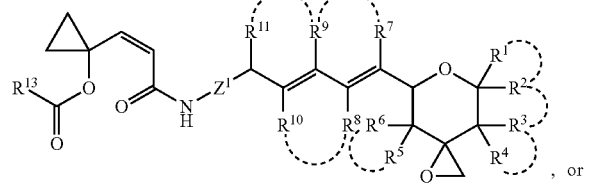, or

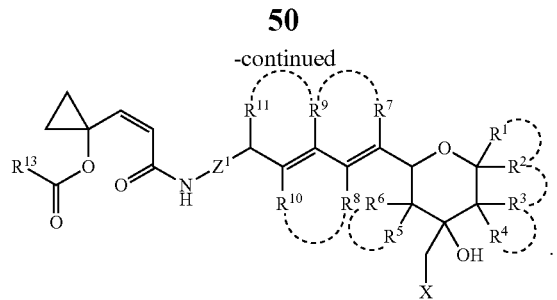

In a still further aspect, both $R^{12}$ and $R^{13}$ independently comprise methyl.

In one aspect, $Z^1$ comprises optionally substituted cycloalkyl or cycloalkenyl or cycloalkynyl, an optionally substituted heterocycloalkyl or heterocycloalkenyl or heterocycloalkynyl, or optionally substituted aryl, or optionally substituted heteroaryl. In a further aspect, $Z^1$ comprises an optionally substituted cyclopropyl, cyclobutyl, cyclopentyl, cyclohexyl, cycloheptyl, heterocyclopropyl, heterocyclobutyl, heterocyclopentyl, heterocyclohexyl, heterocycloheptyl, furan, pyran, oxole, oxazine, thiophene, thioazole, oxathiolane, pyrrolidine, pyrazolidine, imidazolidine, triazolidine, perhydropyridine, azole, morpholine, pyridine, pyrimidine, or benzene.

In a further aspect, $Z^1$ has a structure represented by a formula:

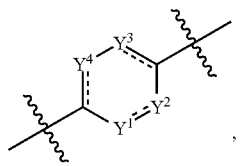

wherein $Y^1, Y^2, Y^3$, and $Y^4$ independently comprises oxygen, optionally substituted carbon, or optionally substituted nitrogen with a structure represented by the formula, $NR^{14}R^{15}$, wherein $R^{14}$ and $R^{15}$ independently comprises hydrogen or optionally substituted alkyl comprising from 1 to 4 carbons; and wherein ----- is an optional bond.

In one aspect, the compound can be present as:

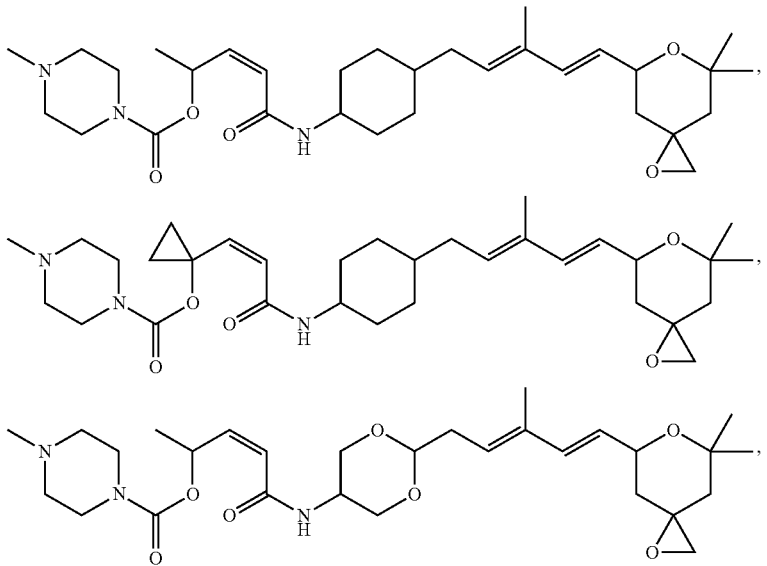

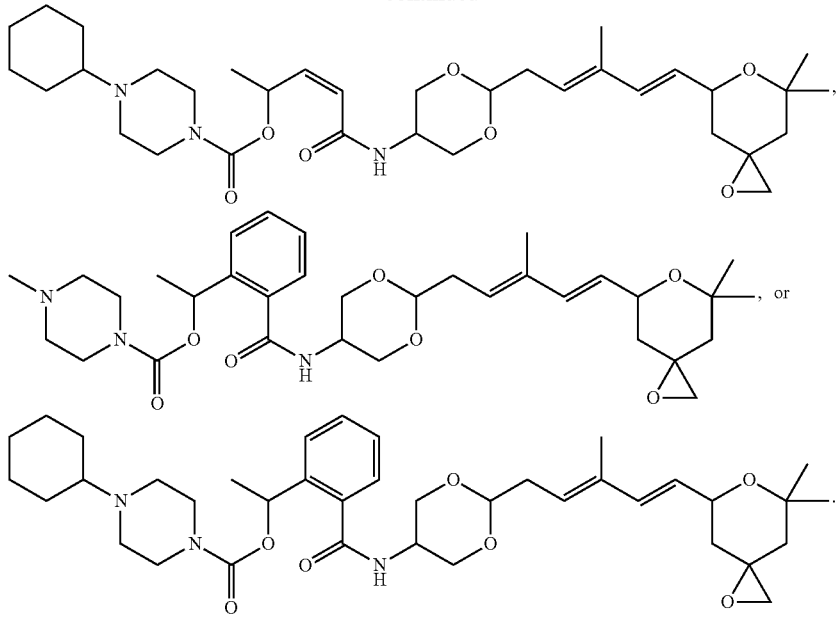
In a specific aspect, the compound can be present as:
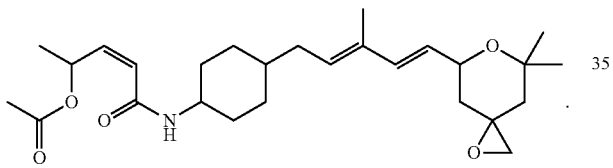
In one aspect, the compound comprises a single diastereomer. For example, the compound can be substantially enantiopure.
In a further aspect, the compound can have a structure represented by a formula selected from:
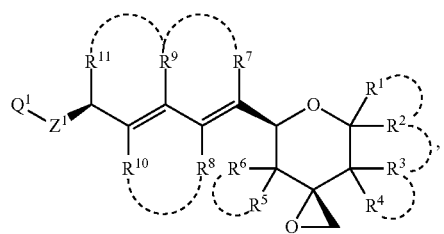
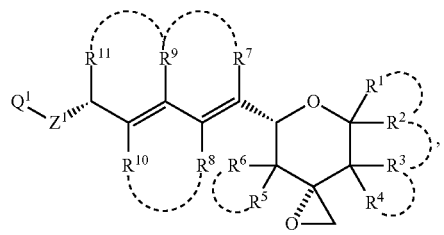
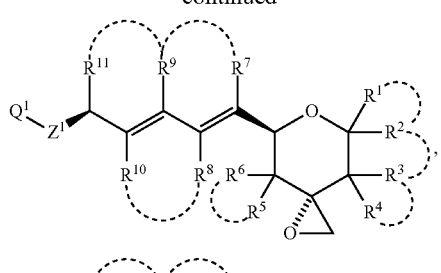
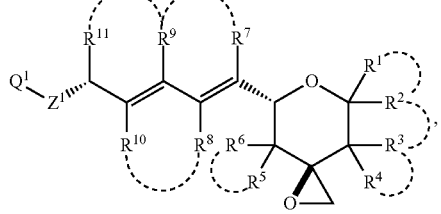
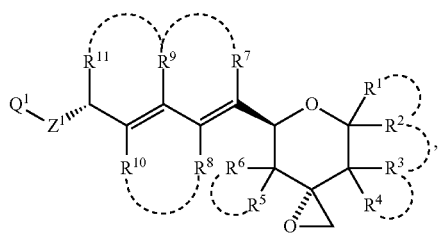

-continued

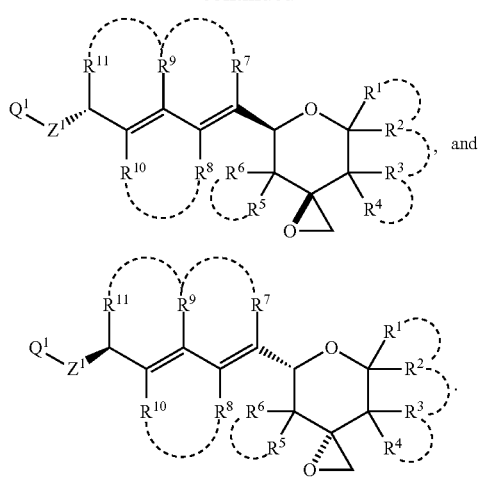

In a specific aspect, the compound can have a structure represented by the formula:

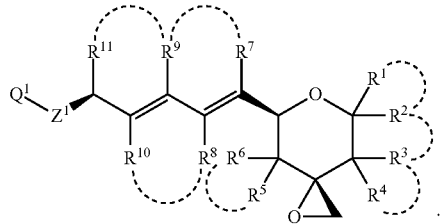

In one aspect, $Q^1$ has a structure represented by a formula selected from:

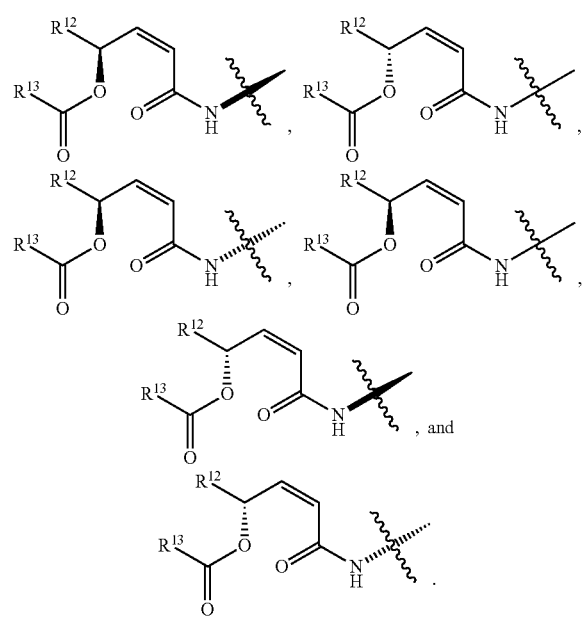

In a further aspect, $Q^1$ has a structure represented by a formula selected from:

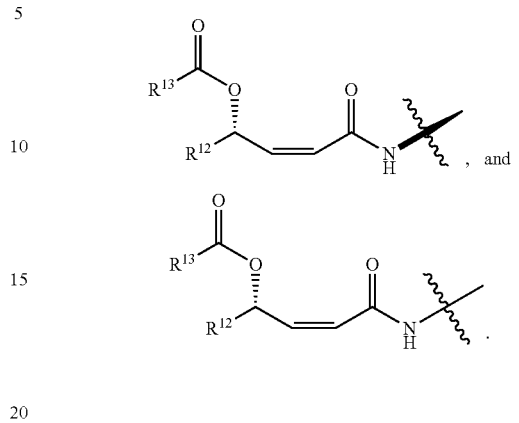

In one aspect, the compound can have a structure represented by the formula:

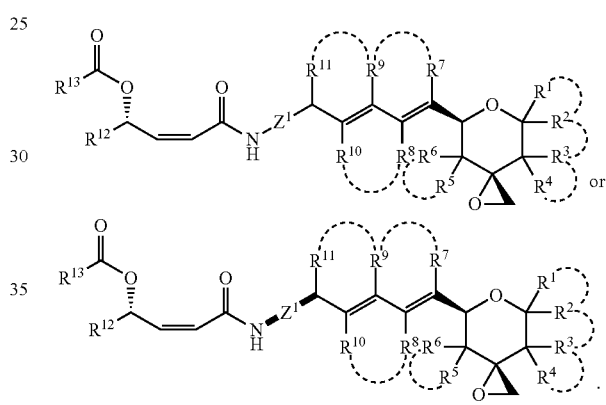

In this aspect, $R^1$ and $R^2$ can be methyl, and each of $R^3$, $R^4$, $R^5$, and $R^6$ can be hydrogen. In a further example of this aspect, $R^9$ can be methyl.

In a further aspect, the compound has a structure represented by the formula:

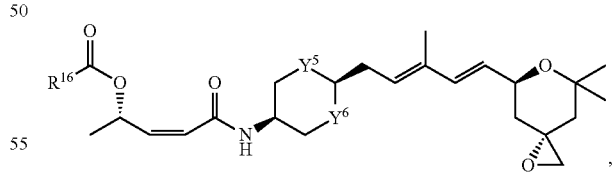

wherein $Y^5$ and $Y^6$ independently represent O or $CH_2$; and wherein $R^{16}$ represents optionally substituted $C_1$-$C_4$ alkyl, optionally substituted aryl, optionally substituted heteroaryl, optionally substituted cycloalkyl, or optionally substituted heterocycloalkyl.

Exemplary compounds within this formula include without limitation the following compounds:

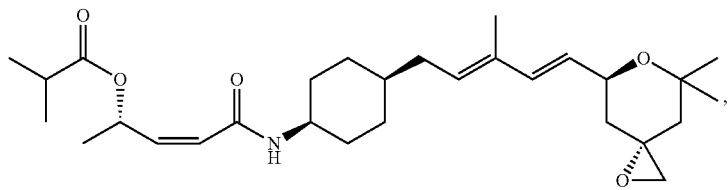
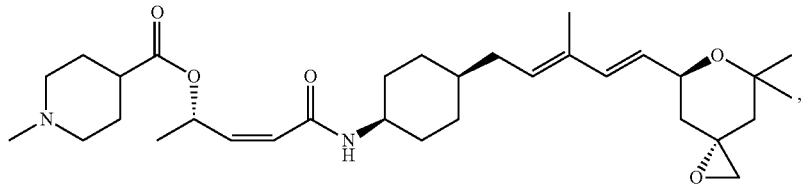
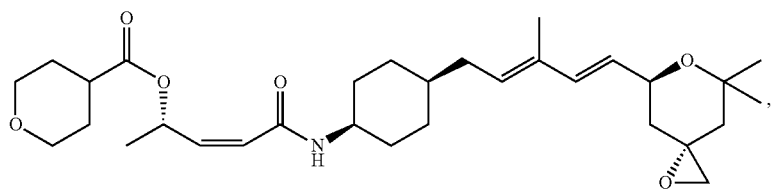
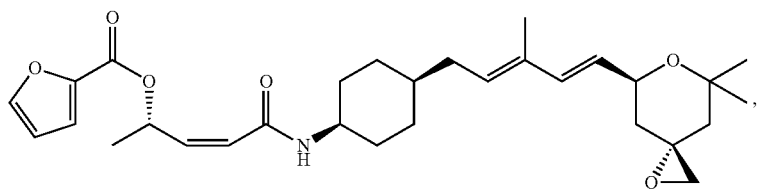
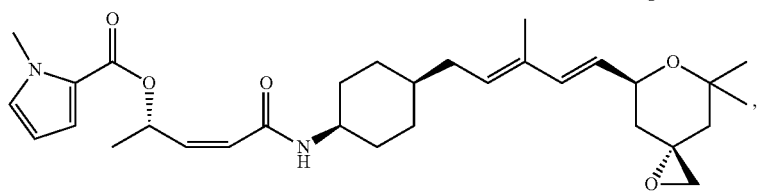
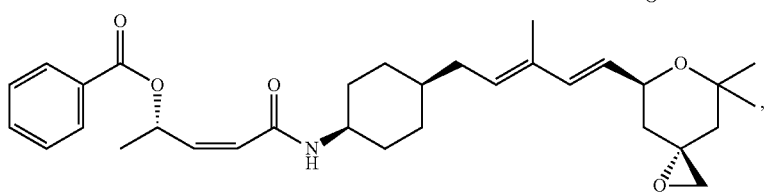
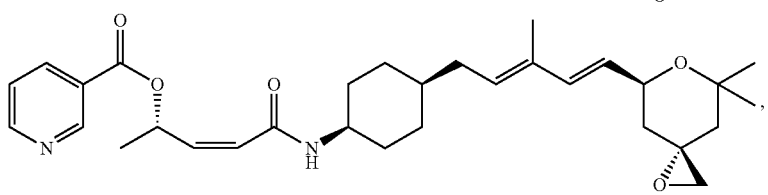
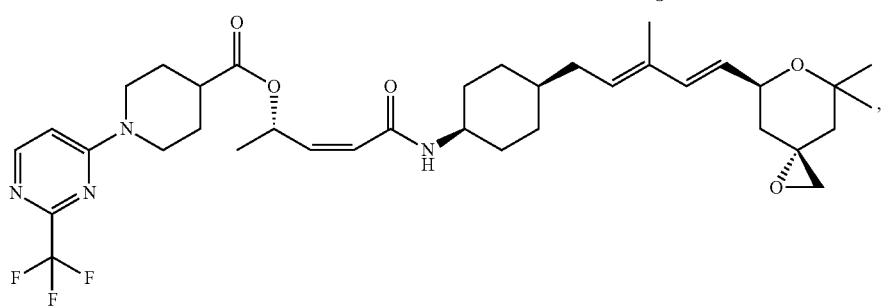

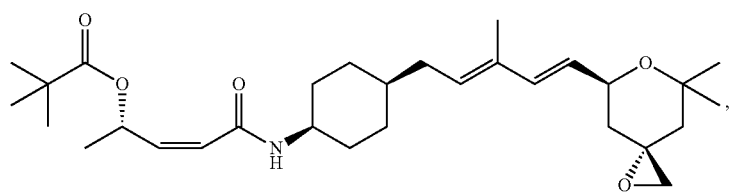
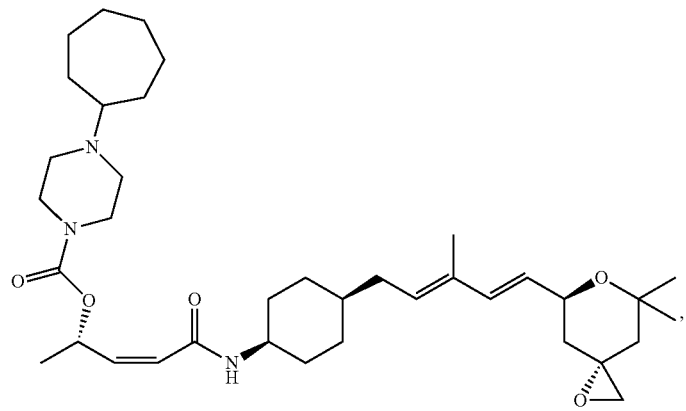
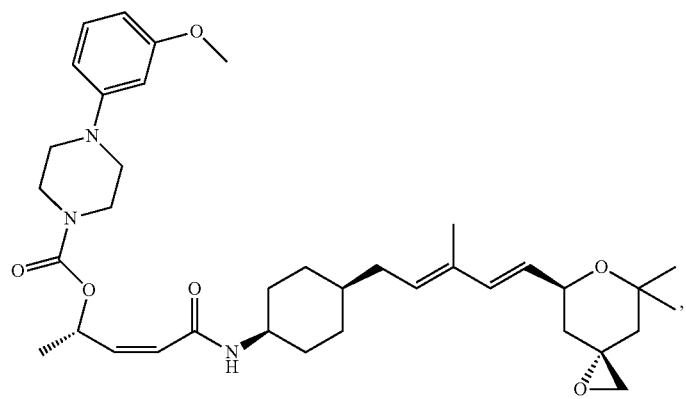
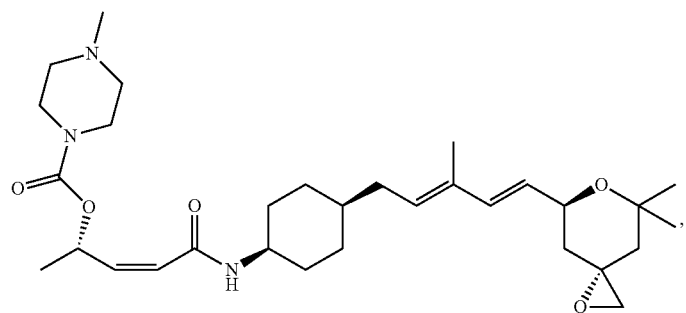
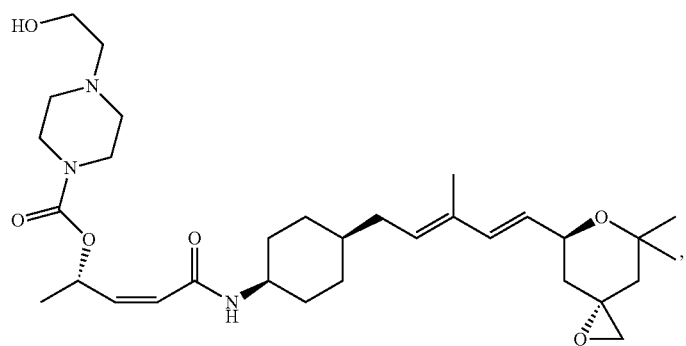

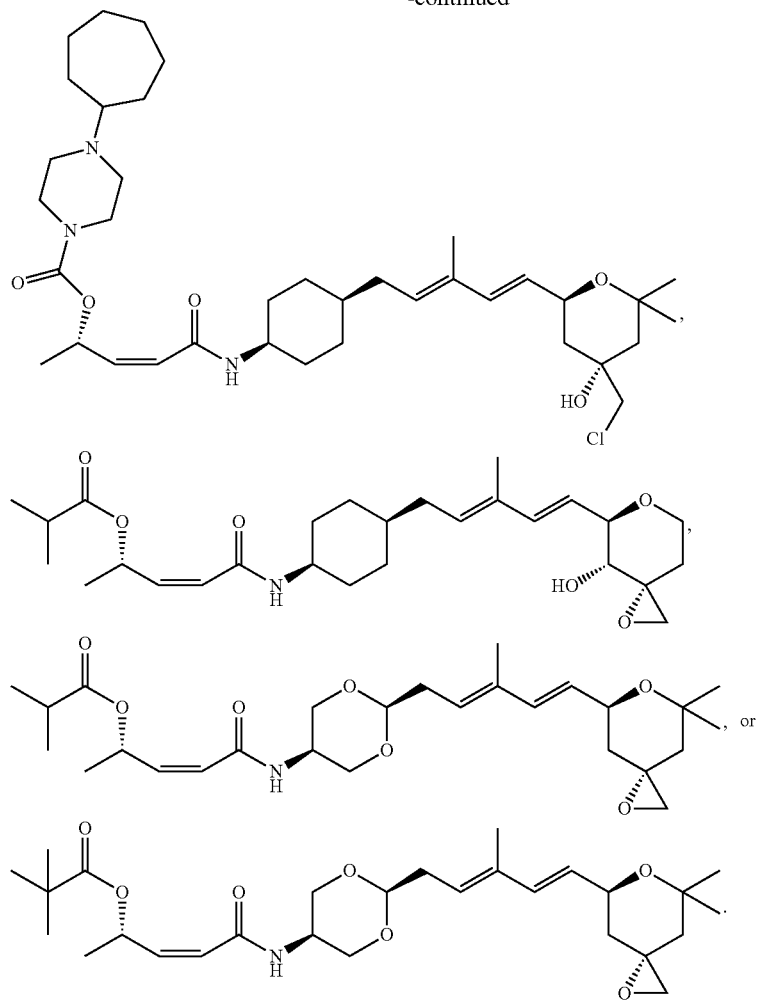

In a further aspect, the compound has a structure represented by the formula:

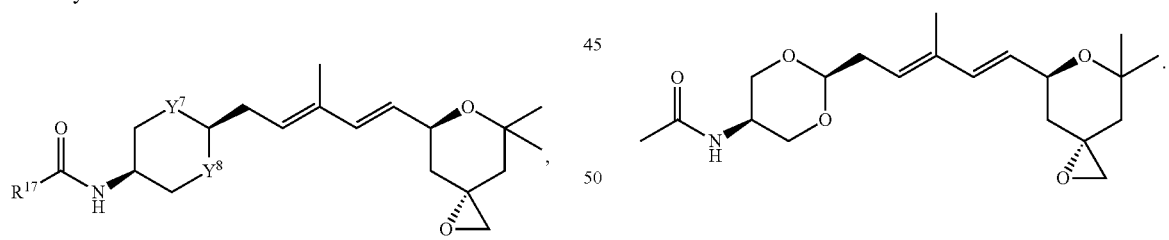

wherein $Y^7$ and $Y^8$ independently represent O or $CH_2$; and wherein $R^{17}$ represents optionally substituted $C_1$-$C_4$ alkyl.

Exemplary compounds within this formula include without limitation:

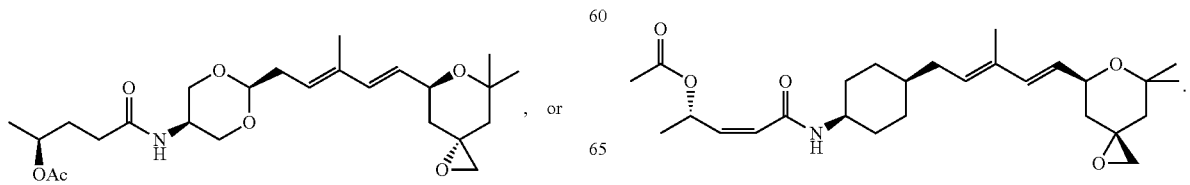

For any compound comprising a single diastereomer or enantiomer, as disclosed herein, $Z^1$ can comprise a 1,4-cyclohexane residue. For example, a compound can have a structure represented by the formula:

In a further aspect, the compound can be present as:

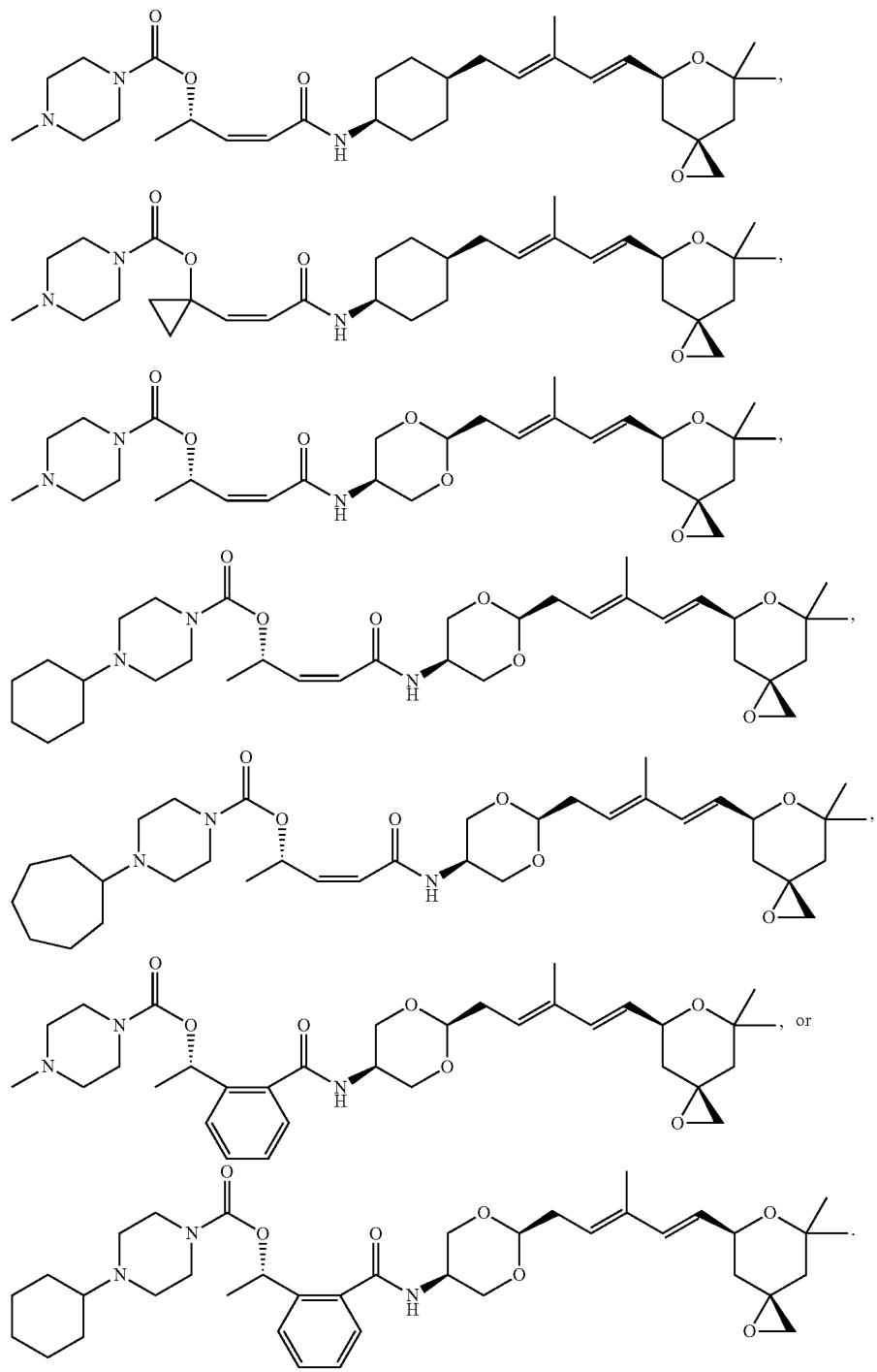

In a still further aspect, the compound can be present as: (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl acetate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl acetate; (S,Z)-5-((2R,5R)-5-((2E,4E)-5-((3R,5S)-7,7-dimethyl-1,6-dioxaspiro[2.5]octan-5-yl)-3-methylpenta-2,4-dienyl)-1,3-dioxan-2-ylamino)-5-oxopent-3-en-2-yl acetate; (S)-1-(2-((1R,4R)-4-((2E,4E)-5-((3R,5S)-7,7-dimethyl-1,6-dioxaspiro[2.5]octan-5-yl)-3-methylpenta-2,4-dienyl)cyclohexylcarbamoyl)phenyl)ethyl acetate; (S)-1-(2-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylcarbamoyl)phenyl)ethyl acetate; (S)-1-(2-((2R,5R)-5-((2E,4E)-5-((3R,5S)-7,7-dimethyl-1,6-dioxaspiro[2.5]octan-5-yl)-3-methylpenta-2,4-dienyl)-1,3-dioxan-2-ylcarbamoyl)phenyl)ethyl acetate;

(S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl 4-methylpiperazine-1-carboxylate; 1-((Z)-3-((1R,4S)-4-((2E,4E)-5-((3R,5S)-7,7-dimethyl-1,6-dioxaspiro[2.5]octan-5-yl)-3-methylpenta-2,4-dienyl)cyclohexylamino)-3-oxoprop-1-enyl)cyclopropyl 4-methylpiperazine-1-carboxylate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl 4-methylpiperazine-1-carboxylate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl 4-cyclohexylpiperazine-1-carboxylate; and (S)-1-(2-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylcarbamoyl)phenyl)ethyl 4-cyclohexylpiperazine-1-carboxylate.

7. Use of Compounds

Also provided are uses of the disclosed compounds. For example, provided is the use of a compound having a structure represented by a formula:

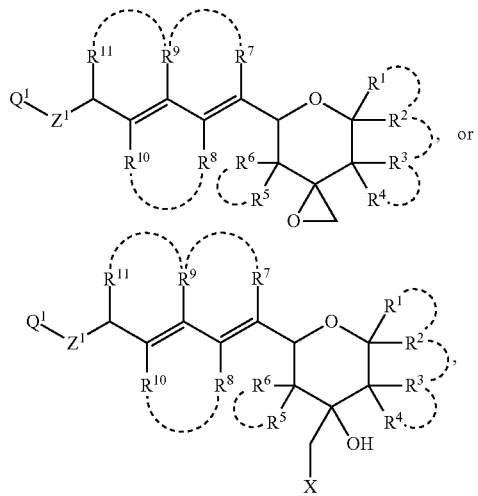

wherein each of $R^1$, $R^2$, $R^3$, $R^4$, $R^5$, and $R^6$ independently comprises halide, hydrogen, hydroxyl, amino, thiol, or optionally substituted organic residue comprising from 1 to 6 carbons; wherein each of $R^7$, $R^8$, $R^9$, $R^{10}$, and $R^{11}$ independently comprises halide, hydrogen, hydroxyl, amino, thiol, or optionally substituted organic residue comprising from 1 to 6 carbons; and wherein each ----- is an optional covalent bond; and wherein X is a leaving group; wherein $Z^1$ comprises an optionally substituted 3, 4, 5, 6, or 7 membered ring; wherein if $R^5$ or $R^6$ is hydroxyl or alkoxyl, then $Z^1$ comprises a ring with no more than three chiral centers; and wherein $Q^1$ comprises an optionally substituted organic residue comprising from 1 to 26 carbons; or a pharmaceutically acceptable derivative thereof, with a pharmaceutically acceptable carrier.

In a further aspect, $Z^1$ comprises a ring with no more than two chiral centers in the 3, 4, 5, 6, or 7 membered ring. For example, $Z^1$ can have two chiral centers in the 3, 4, 5, 6, or 7 membered ring. In a specific aspect, $Z^1$ can have two chiral centers in the 6 membered ring.

In a further aspect, neither $R^5$ nor $R^6$ comprises hydroxyl. In a still further aspect, at least one of $R^5$ and $R^6$ comprises hydroxyl.

In one aspect, $Z^1$ comprises a ring with no more than three stereocenters. In a further aspect, $Z^1$ comprises a ring that can include but is not limited to:

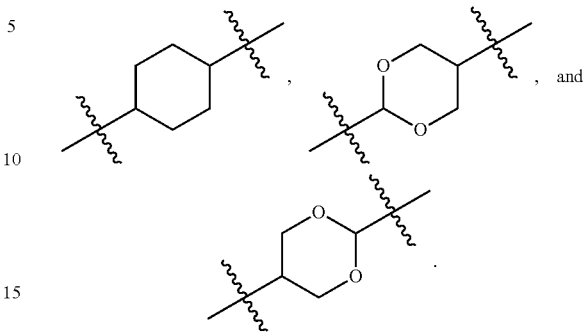

In a further aspect, $R^1$ and $R^2$ independently comprise hydroxyl, methyl, ethyl, propyl, or butyl, and $R^3$, $R^4$, $R^5$, and $R^6$ independently comprises hydrogen. In a still further aspect, both $R^1$ and $R^2$ independently comprise methyl. In one aspect, at least one of $R^1$ and $R^2$ comprises hydroxyl.

In one aspect, each of $R^7$, $R^8$, $R^9$, $R^{10}$, and $R^{11}$ independently comprises hydrogen or optionally substituted organic residue comprising from 1 to 4 carbons. In a specific aspect, $R^9$ comprises methyl. In a further aspect, each of $R^7$, $R^8$, $R^9$, $R^{10}$, and $R^{11}$ is hydrogen.

In one aspect, $Q^1$ comprises optionally substituted heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, or optionally substituted heteroaryl.

In a further aspect, the compound has a structure represented by a formula:

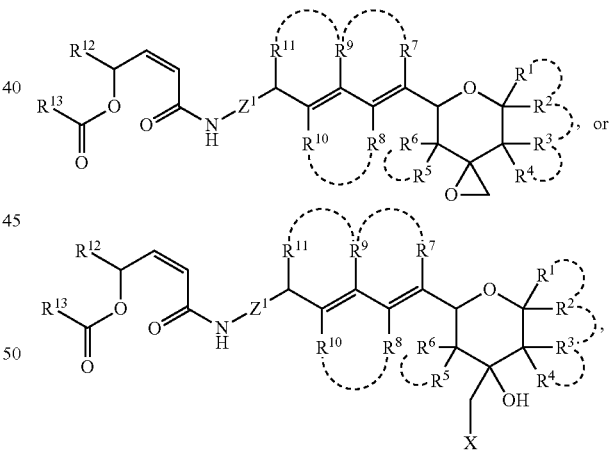

wherein $R^{12}$ and $R^{13}$ independently comprises hydrogen or optionally substituted organic residue comprising from 1 to 16 carbons;

In one aspect, $R^{13}$ comprises hydrogen, methyl, ethyl, propyl, butyl, amino, optionally substituted organic alkoxy, amino alkyl, heteroalkyl or heteroalkenyl or heteroalkynyl, optionally substituted cycloalkyl or cycloalkenyl or cycloalkynyl, optionally substituted heterocycloalkyl or heterocycloalkenyl or heterocycloalkynyl, optionally substituted aryl, or optionally substituted heteroaryl. In a further aspect, $R^{13}$ comprises alkylamino, dialkylamino, or cycloalkylamino comprising from 1 to 12 carbons. In a specific aspect, $R^{13}$ comprises optionally substituted piperazinyl.

In a further aspect, $R^{13}$ comprises a substituent having a structure represented by the formula:

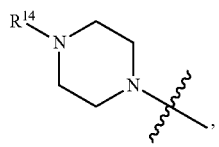

wherein $R^{14}$ comprises alkyl, heteroalkyl, cycloalkyl, or heterocycloalkyl.

In a still further aspect, $R^{14}$ can be optionally substituted methyl, ethyl, propyl, butyl, cyclobutyl, cyclopentyl, and cyclohexyl.

In one aspect, $R^{12}$ comprises hydrogen, optionally substituted methyl, ethyl, propyl, butyl, pentyl, or hexyl.

In a further aspect, the compound comprises a structure represented by a formula:

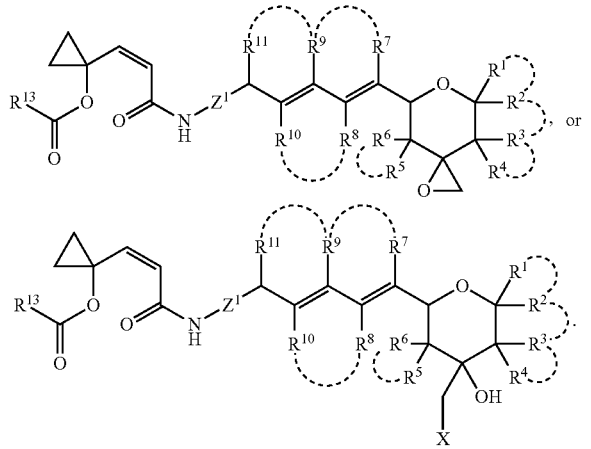

In a still further aspect, both $R^{12}$ and $R^{13}$ independently comprises methyl.

In one aspect, $Z^1$ comprises optionally substituted cycloalkyl or cycloalkenyl or cycloalkynyl, an optionally substituted heterocycloalkyl or heterocycloalkenyl or heterocycloalkynyl, or optionally substituted aryl, or optionally substituted heteroaryl. In a further aspect, $Z^1$ comprises an optionally substituted cyclopropyl, cyclobutyl, cyclopentyl, cyclohexyl, cycloheptyl, heterocyclopropyl, heterocyclobutyl, heterocyclopentyl, heterocyclohexyl, heterocycloheptyl, furan, pyran, oxole, oxazine, thiophene, thioazole, oxathiolane, pyrrolidine, pyrazolidine, imidazolidine, triazolidine, perhydropyridine, azole, morpholine, pyridine, pyrimidine, or benzene.

In a further aspect, $Z^1$ has a structure represented by a formula:

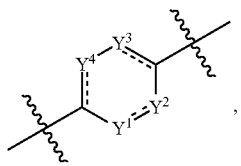

wherein $Y^1$, $Y^2$, $Y^3$, and $Y^4$ independently comprises oxygen, optionally substituted carbon, or optionally substituted nitrogen with a structure represented by the formula, $NR^{14}R^{15}$, wherein $R^{14}$ and $R^{15}$ independently comprises hydrogen or optionally substituted alkyl comprising from 1 to 4 carbons; and wherein ----- is an optional bond.

In one aspect, the compound can be present as:

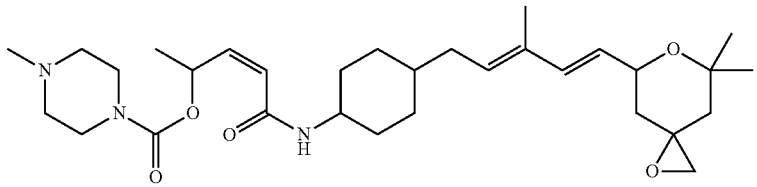

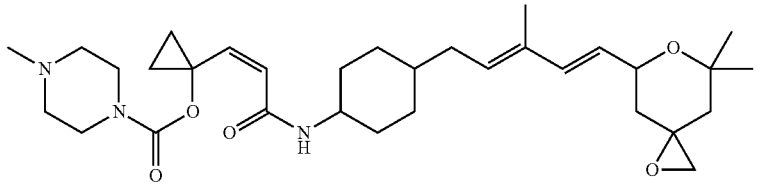

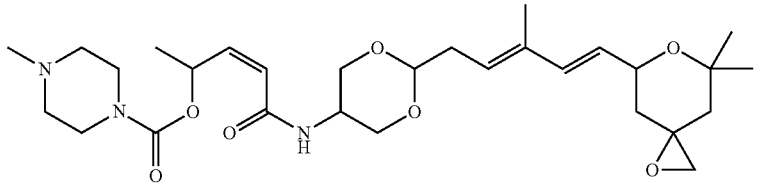

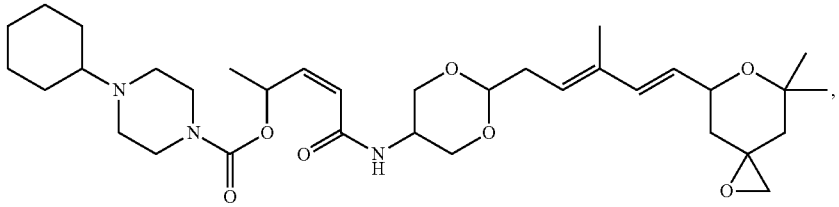

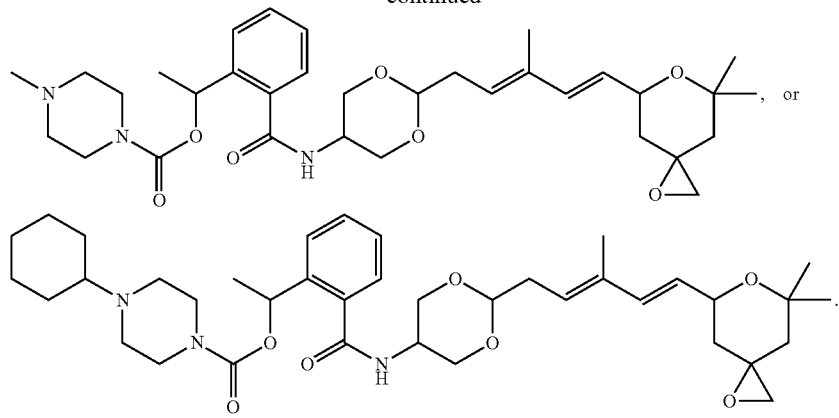, or
In a specific aspect, the compound can be present as:
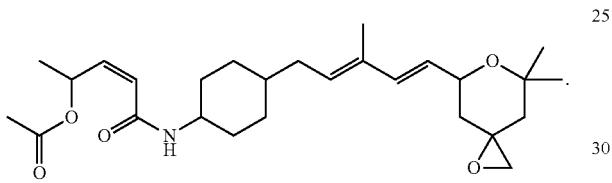
In one aspect, the compound comprises a single diastereomer. For example, the compound can be substantially enantiopure.
In a further aspect, the compound can have a structure represented by a formula selected from:
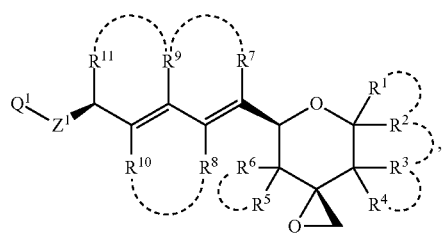
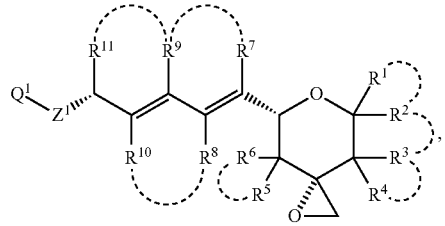
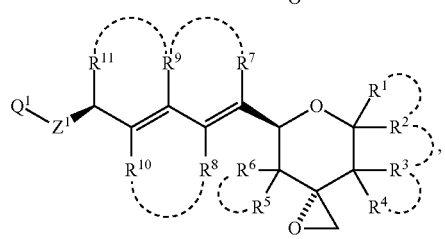
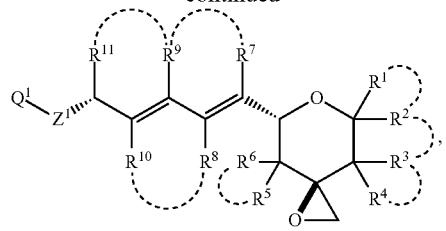
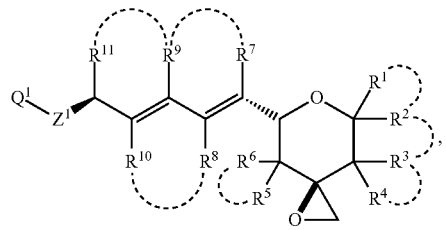
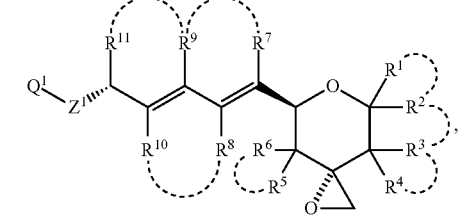
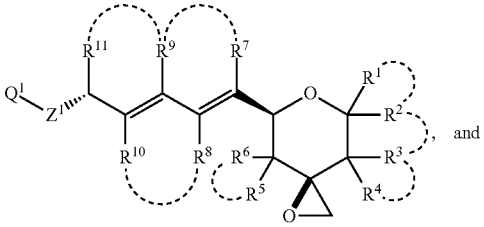
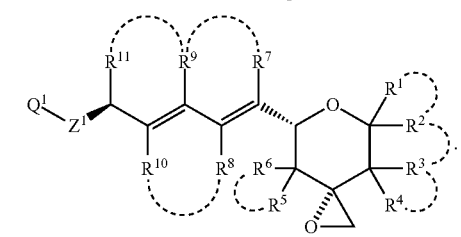, and In a specific aspect, the compound can have a structure represented by the formula:

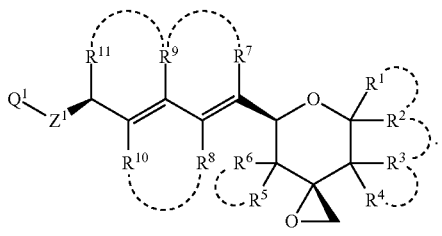

In one aspect, $Q^1$ has a structure represented by a formula selected from:

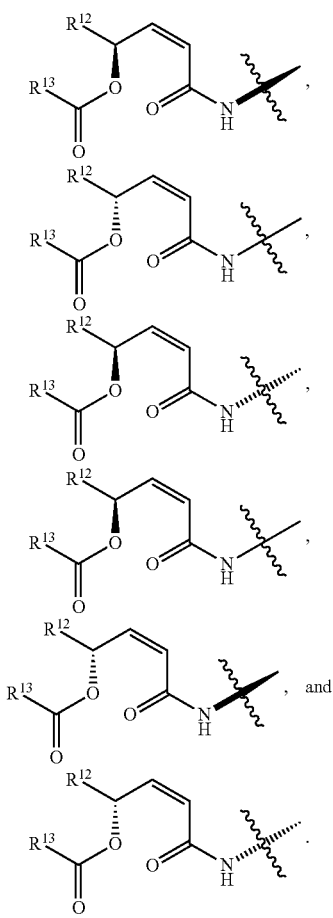

In a further aspect, $Q^1$ has a structure represented by a formula selected from:

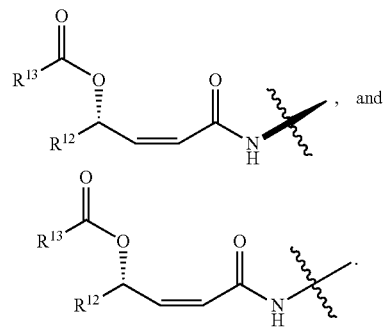

In one aspect, the compound can have a structure represented by the formula:

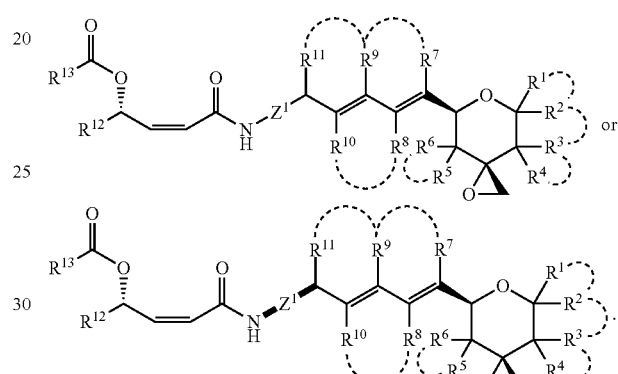

In this aspect, $R^1$ and $R^2$ can be methyl, and each of $R^3$, $R^4$, $R^5$, and $R^6$ can be hydrogen. In a further example of this aspect, $R^9$ can be methyl.

In a further aspect, the compound has a structure represented by the formula:

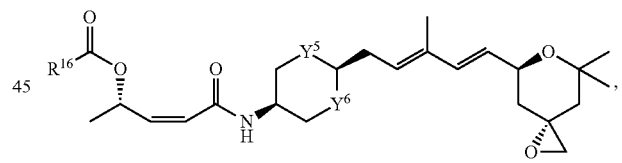

wherein $Y^5$ and $Y^6$ independently represent O or $CH_2$; and wherein $R^{16}$ represents optionally substituted $C_1$-$C_4$ alkyl, optionally substituted aryl, optionally substituted heteroaryl, optionally substituted cycloalkyl, or optionally substituted heterocycloalkyl.

Exemplary compounds within this formula include without limitation the following compounds:

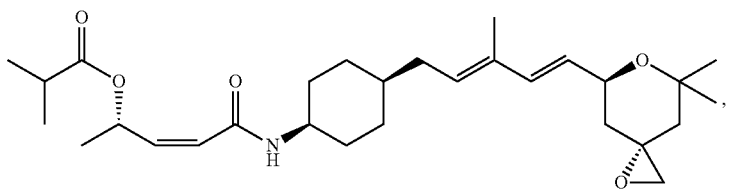

-continued
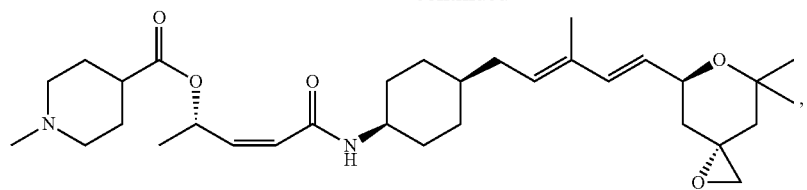
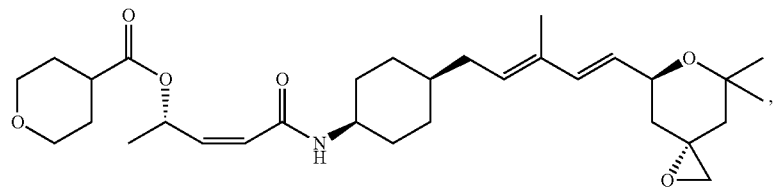
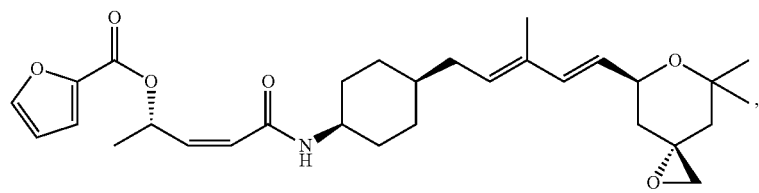
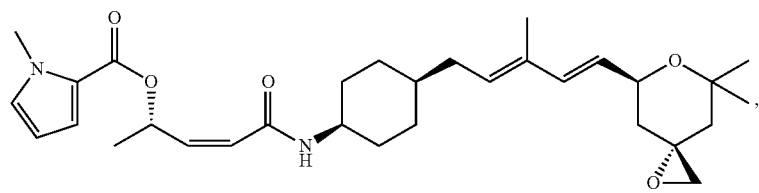
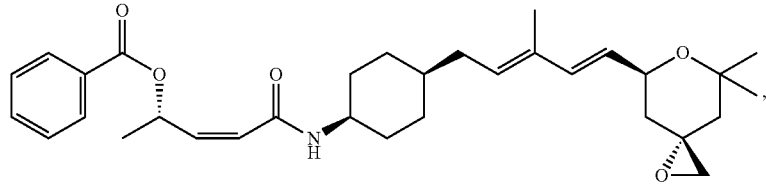
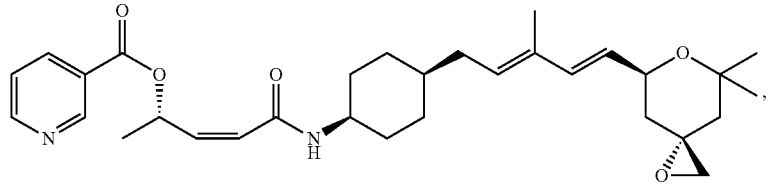
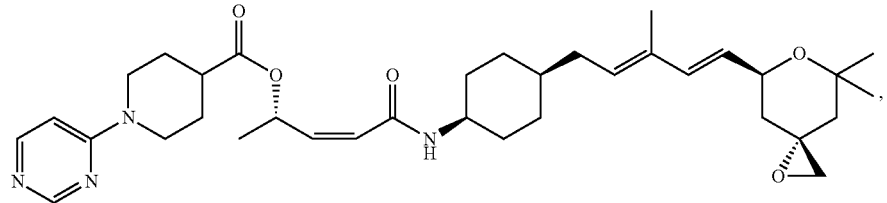
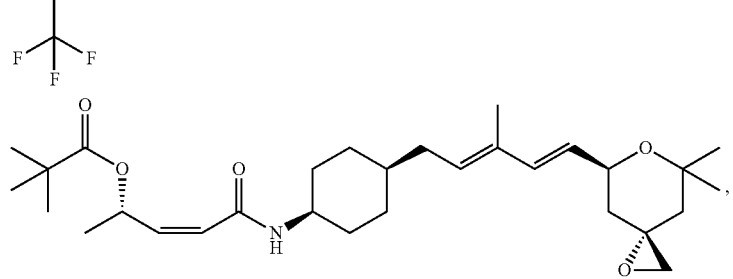

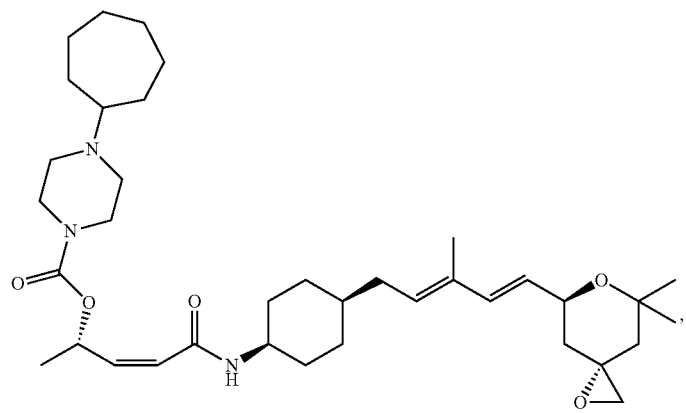
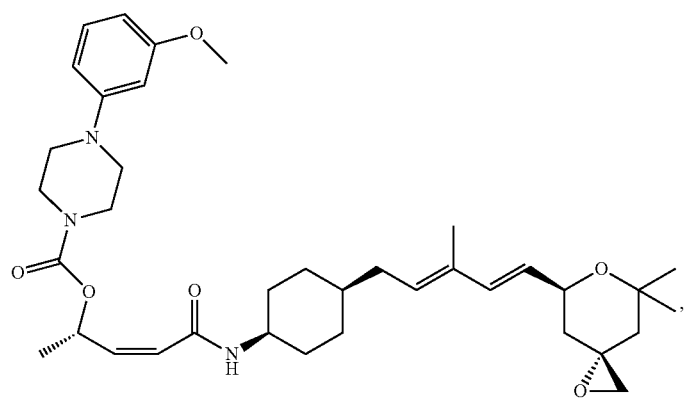
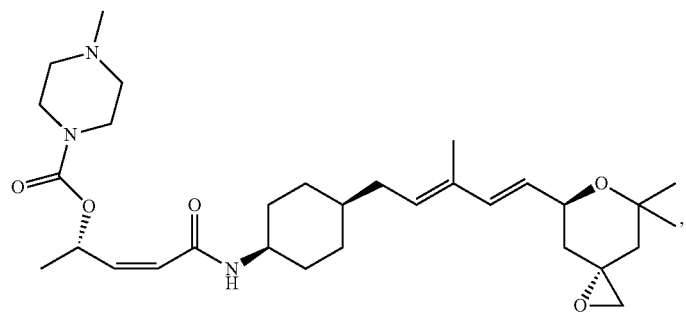
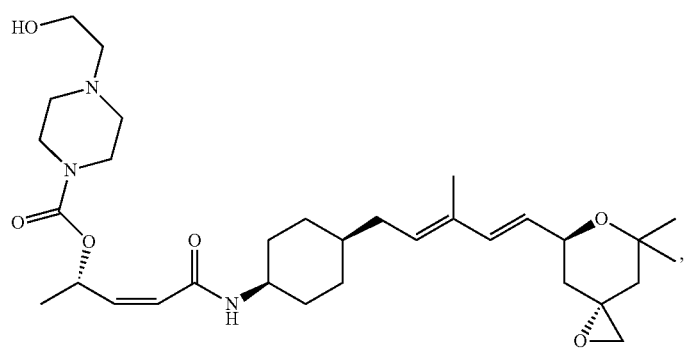

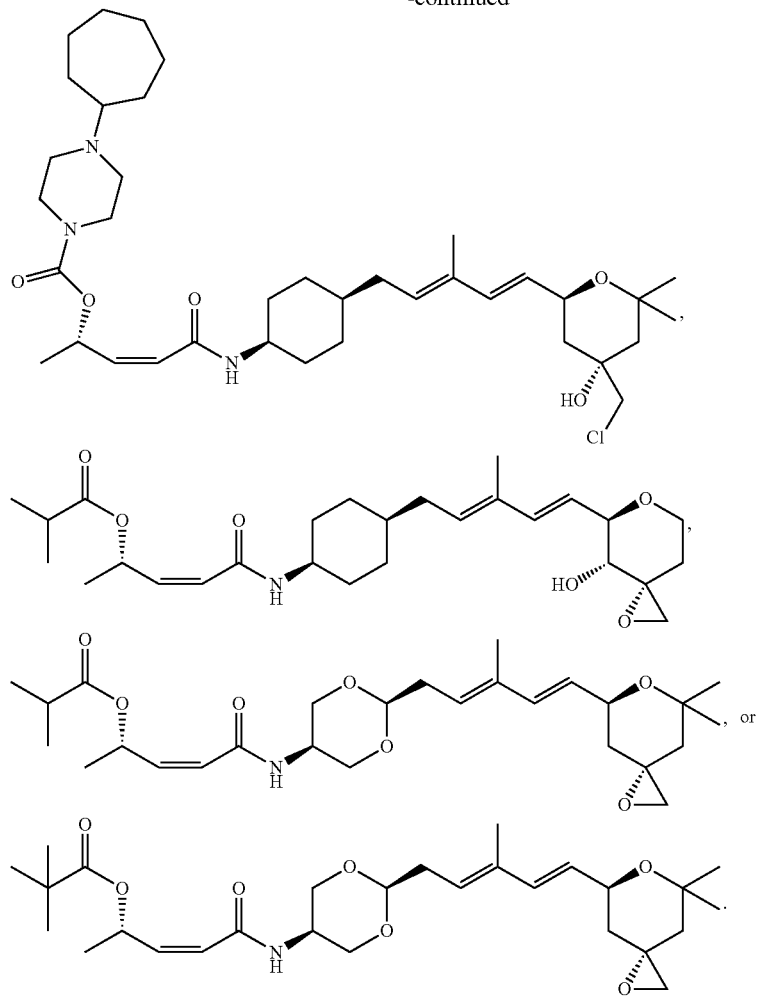

In a further aspect, the compound has a structure represented by the formula:

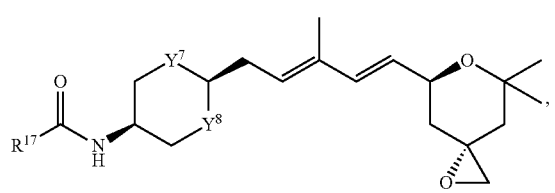

wherein $Y^7$ and $Y^8$ independently represent O or $CH_2$; and wherein $R^{17}$ represents optionally substituted $C_1$-$C_4$ alkyl.

Exemplary compounds within this formula include without limitation:

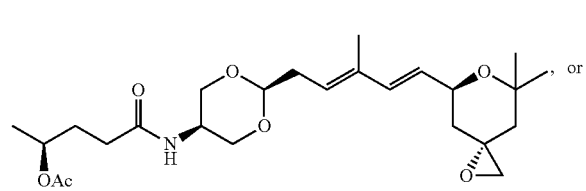

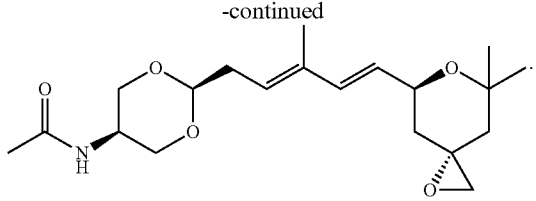

For any compound comprising a single diastereomer or enantiomer, as disclosed herein, $Z^1$ can comprise a 1,4-cyclohexane residue. For example, a compound can have a structure represented by the formula:

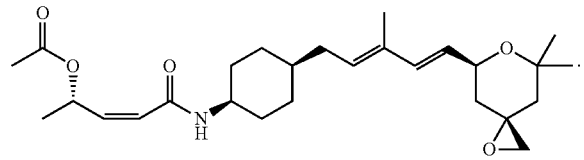 [SMILES: CC(=O)O[C@@H](C)/C=C\C(=O)N[C@H]1CC[C@@H](C/C=C(C)/C=C/[C@@H]2C[C@]3(CO3)CC(C)(C)O2)CC1]

In a further aspect, the compound can be present as:

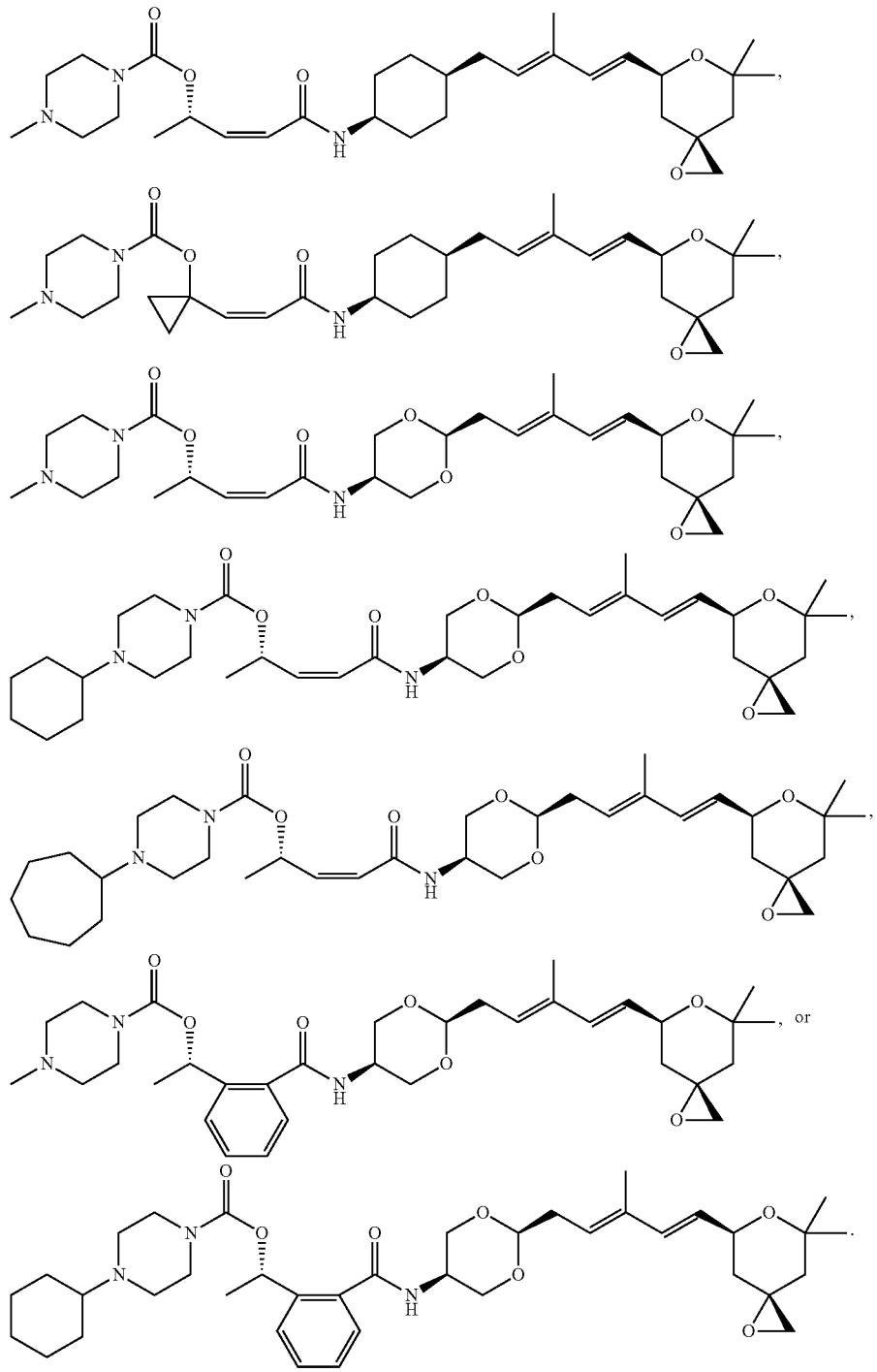

In a still further aspect, the compound can be present as: (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl acetate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl acetate; (S,Z)-5-((2R,5R)-5-((2E,4E)-5-((3R,5S)-7,7-dimethyl-1,6-dioxaspiro[2.5]octan-5-yl)-3-methylpenta-2,4-dienyl)-1,3-dioxan-2-ylamino)-5-oxopent-3-en-2-yl acetate; (S)-1-(2-((1R,4R)-4-((2E,4E)-5-((3R,5S)-7,7-dimethyl-1,6-dioxaspiro[2.5]octan-5-yl)-3-methylpenta-2,4-dienyl)cyclohexylcarbamoyl)phenyl)ethyl acetate; (S)-1-(2-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylcarbamoyl)phenyl)ethyl acetate; (S)-1-(2-((2R,5R)-5-((2E,4E)-5-((3R,5S)-7,7-dimethyl-1,6-dioxaspiro[2.5]octan-5-yl)-3-methylpenta-2,4-dienyl)-1,3-dioxan-2-ylcarbamoyl)phenyl)ethyl acetate;

(S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl 4-methylpiperazine-1-carboxylate; 1-((Z)-3-((1R,4S)-4-((2E,4E)-5-((3R,5S)-7,7-dimethyl-1,6-dioxaspiro[2.5]octan-5-yl)-3-methylpenta-2,4-dienyl)cyclohexylamino)-3-oxoprop-1-enyl)cyclopropyl 4-methylpiperazine-1-carboxylate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl 4-methylpiperazine-1-carboxylate; (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl 4-cyclohexylpiperazine-1-carboxylate; and (S)-1-(2-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylcarbamoyl)phenyl)ethyl 4-cyclohexylpiperazine-1-carboxylate.

In one aspect, the use relates to the treatment of a disorder in a subject, e.g., a mammal, including a human.

G. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. General Methods

Reactions carried out under anhydrous conditions were performed under $N_2$ using oven-dried glassware specified otherwise. THF, toluene, acetonitrile and $CH_2Cl_2$ were distilled before use. All other reagents and solvents used were reagent grade. Flash column chromatography was performed according to Still's procedure using 100-700 times excess 32-64 mm grade silica gel. TLC analysis was performed using glass TLC plates (0.25 mm, 60 F-254 silica gel). Visualization of the developed plates was accomplished by staining with ethanolic phosphomolybdic acid, ceric ammonium molybdate, or ethanolic ninhydrin followed by heating on a hot plate (120° C.). The values δH7.26 and δC 77.0 ppm were used as references for NMR spectroscopy in $CDCl_3$. The coupling constants deduced in $^1H$ NMR data cases were obtained by first-order coupling analysis.

2. Synthesis of (S)-butyl 6,6-dimethyl-4-oxotetrahydro-2H-pyran-2-carboxylate

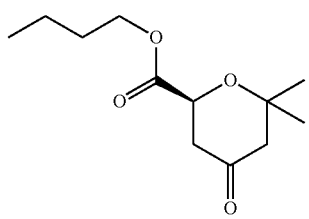 [SMILES: CCCCOC(=O)[C@@H]1CC(=O)CC(C)(C)O1]

A solution of Indalon (230 mg) and 2R,5R-5-butyl-methyl-2-(5-methylfuran-2-yl) imidazolidin-4-one (55 mg) in dry ether (4.6 mL) was stirred and cooled at ice bath temp (0-4° C.) as t-Butyl Hantzch ester (346 mg) and trichloroacetic acid (32 mg) were added sequentially. The resulted yellow solution was stirred at ice bath temp for 3 days, and monitored by TLC. The reaction mix was passed through a short pad of silica gel and eluted with ether (60 mL). Concentration of the ether and purified by flash chromatography (20% EtOAc in Hexane) gave 204 mg (88%) of the product as oil: $^1H$ NMR (400 MHz, $CDCl_3$) δ 4.46 (dd, 1H, J=4.0, 11.0 Hz), 4.19 (td, 2H, J=2.7, 6.7 Hz), 2.58 (dd, 1H, J=1.6, 14.0 Hz), 2.56 (d, 1H, J=13.2), 2.50 (s, H, J=13.2 Hz), 2.32 (dd, 1H, J=1.6, 14.0 Hz), 1.64 (m, 2H), 1.46 (s, 3H), 1.37 (m, 2H), 1.23 (s, 3H), 0.94 (t, 3H, J=7.4 Hz); $^{13}C$ NMR ($CDCl_3$, 100 MHz) ä 205.2, 170.1, 76.2, 70.0, 65.4, 52.9, 43.5, 30.5, 28.6, 28.0, 23.8, 19.0, 13.6.

3. Synthesis of (3R,5S)-butyl 7,7-dimethyl-1,6-dioxaspiro[2.5]octane-5-carboxylate

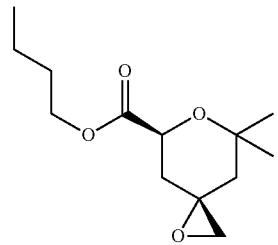 [SMILES: CCCCOC(=O)[C@@H]1C[C@]2(CO2)CC(C)(C)O1]

In a 25 mL two neck RB flask, NaH (96 mg, 60% on mineral oil) and oxotrimethylsulfonium iodide (491 mg) were taken and dissolved in (4.2 mL) of DMSO (dried over 4 Å molecular sieves) at room temperature. The suspension was stirred for 30 min to become clear solution. The starting material (500 mg) in DMSO (1.0 mL) was added dropwise and the solution was turned into light yellow during addition, and stirred for another 1 hour at room temperature and TLC was showed the completion of the reaction. The reaction was quenched with ice cold water. The product was extracted with EtOAc (3×30 mL) and washed with water (2×15 mL) and brine (20 mL), dried over $MgSO_4$. The solvent was evaporated under reduced pressure to give crude residue. Chromatography (20% EtOAc in hexane) gave 430 mg (81%) of epoxide derivative as a liquid. $^1H$ NMR (400 MHz, $CDCl_3$) δ 4.53 (dd, 1H, J=2.7, 12.1 Hz), 4.13 (t, 2H, J=6.7 Hz), 2.61 (dd, 2H, J=4.5, 13.9 Hz), 2.08 (m, 2H), 1.61 (m, 2H), 1.47 (ddd, 1H, J=4.2, 6.7, 10.9 Hz), 1.39 (s, 3H), 1.35 (m, 2H), 1.34 (s, 3H), 1.16 (dd, 1H, J=2.0, 14.0 Hz), 0.93 (t, 3H, J=7.3); $^{13}C$ NMR ($CDCl_3$, 100 MHz) ä 171.5, 74.0, 68.3, 64.9, 55.2, 51.1, 42.2, 35.2, 31.0, 30.5, 23.3, 19.0, 13.7.

4. Synthesis of tert-butyl (1S,4S)-4-(2-hydroxyethyl)cyclohexylcarbamate

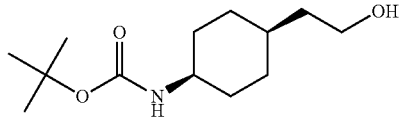 [SMILES: CC(C)(C)OC(=O)N[C@H]1CC[C@@H](CCO)CC1]

In a 100 mL RB single neck flask, the acid (1.0 g) was dissolved in THF (16 mL) and cooled at 0° C. $BH_3$-THF (10.1 mL, 1.0 M in THF) was added drop wise. The resulting colorless and homogenous solution was stirred for 3 hours at 23° C. TLC showed the all of the starting material was consumed. Reaction was cooled at 0° C. and aq. 3N NaOH (3.2 mL) was added to destroy the excess borane reagent and hydrolyze the NH-borane complex. The mixture was stirred for 1.5 hours. After THF removed by roto-evaporator, EtOAc (100 mL) and aq NaHCO₃ (40 mL) were added. The product was extracted with EtOAc (2×50 mL). The combined layers were washed with water (40 mL) and brine (40 mL), dried over MgSO₄. Evaporation of solvent gave crude residue that was purified on silica-gel chromatography (60% EtOAc in hexane) to give 840 mg (89%) of the alcohol as a white solid; $^1$H NMR (400 MHz, CDCl₃) δ 4.65 (s, 1H), 3.71 (dd, 3H, J=6.4, 11.6 Hz), 1.58 (m, 10H), 1.47 (s, 9H), 1.25 (s, 3H); $^{13}$C NMR (CDCl₃, 100 MHz) ä 155.2, 79.1, 60.8, 46.4, 38.4, 29.7, 28.6, 27.8.

5. Synthesis of tert-butyl 4-(2-oxoethyl)cyclohexylcarbamate

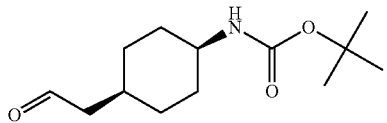 [SMILES: CC(C)(C)OC(=O)N[C@H]1CC[C@@H](CC=O)CC1]

In a 100 mL single neck RB flask, 8 mL of dry DCM and oxalyl chloride (2.96 mL, 2.0 M in DCM) were taken. The solution was cooled to −78° C. and DMSO (0.42 mL) was then added drop wise. The reaction was stirred for 20 min at the same temp and the alcohol (800 mg) in DCM (10 mL) containing 0.5 mL DMSO was added dropwise. The whole mixture was then stirred for 2 h at the same temp and then diisopropylethyl amine (2.9 mL) was added drop wise. The mixture was then allowed to warm to room temp for 1 h and water (60 mL) was added. The product was extracted with DCM (2×100 mL) and washed with aq. 1N HCl (60 mL), water (75 mL) and brine (75 mL), and dried over Na₂SO₄. The solvent was evaporated under vacuum to give crude aldehyde (840 mg) that was used in the next step without further purification. $^1$H NMR (400 MHz, CDCl₃) δ 9.76 (t, 1H, J=2.0 Hz), 4.59 (s, 1H), 3.72 (s, 1H), 2.37 (dd, 2H, J=2.0, 6.9 Hz), 2.04 (s, 1H), 1.62 (dd, 7H, J=4.5, 14.8 Hz), 1.44 (s, 10H), 1.26 (dd, 3H, J=12.5, 21.4 Hz); $^{13}$C NMR (CDCl₃, 100 MHz) 202.1, 155.2, 79.2, 49.5, 46.2, 30.4, 29.5, 28.4, 27.8.

6. Synthesis of (E)-ethyl-4-((1S,4S)-4-(tert-butoxycarbonylamino)cyclohexyl)-2-methylbut-2-enoate

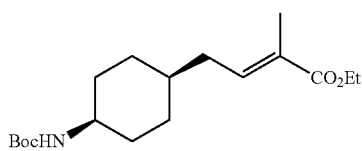 [SMILES: CCOC(=O)/C(C)=C/C[C@H]1CC[C@@H](NC(=O)OC(C)(C)C)CC1]

A solution of aldehyde (from Example 5) in benzene (12 mL) at room temp as ylide (1.42 g) was added. The resulting yellow solution was heated at 60° C. for 2.5 hours. The reaction was then cooled to room temp and the solvent was evaporated under reduced pressure to give crude residue. $^1$H NMR of the crude shows ratio of E/Z is 25:1. Purification of the crude by silica gel chromatography (30% EtOAc in hexane) gave 910 mg of pure conjugated ester (E) and 70 mg of mix of two isomers were obtained. $^1$H NMR (400 MHz, CDCl₃) δ 6.75 (dd, 1H, J=6.3, 7.6 Hz), 4.62 (s, 1H), 4.18 (m, 2H), 3.73 (s, 1H), 2.12 (t, 2H, J=7.2 Hz), 1.82 (s, 3H), 1.60 (t, 8H, J=10.1 Hz), 1.45 (s, 9H), 1.29 (t, 3H, J=7.1 Hz); $^{13}$C NMR (CDCl₃, 100 MHz) δ 68.1, 155.2, 140.6, 128.6, 99.9, 79.0, 60.3, 35.9, 34.7, 29.7, 28.4, 27.8, 14.3, 12.5.

7. tert-butyl(1S,4S)-4-((E)-4-hydroxy-3-methylbut-2-enyl)cyclohexylcarbamate

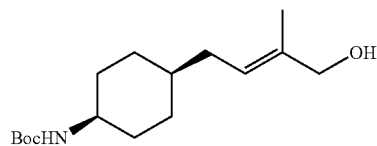 [SMILES: C/C(=C\C[C@H]1CC[C@@H](NC(=O)OC(C)(C)C)CC1)CO]

A solution of ester (650 mg, from Example 6) in dry toluene (9 mL) was stirred and cooled at −78° C. as DIBAL-H (6 mL) was added dropwise. The solution was slowly allowed to warm to −5-0° C. and stirred for 30 min. The solution was then cooled to −70° C. and quenched with MeOH (1.25 mL). The whole mixture was poured into a 1N HCl (cold) (60 mL) and the product was then extracted with EtOAc (3×60 mL). The combined extracts were washed sequentially with water (50 mL), sat aq NaHCO3 (50 mL) and brine (50 mL), dried over NaSO₄. The solvent was evaporated under reduced pressure to give crude residue which was then purified on silica-gel chromatography (40% EtOAc in hexane) to provide corresponding alcohol (510 mg, 90%) as liquid. $^1$H NMR (400 MHz, CDCl₃) δ 5.40 (t, 1H, J=7.4 Hz), 4.65 (s, 1H), 4.01 (d, 2H, J=4.4 Hz), 3.71 (s, 1H), 1.97 (t, 2H, J=7.1 Hz), 1.65 (s, 4H), 1.60 (dd, 6H, J=11.2, 16.0 Hz), 1.44 (s, 11H), 1.18 (m, 2H); $^{13}$C NMR (CDCl₃, 100 MHz) δ 155.2, 135.5, 124.6, 79.0, 68.9, 46.4, 36.4, 33.6, 29.8, 28.4, 27.7, 13.87.

8. Synthesis of tert-butyl (1S,4S)-4-((E)-4-(benzo[d]thiazol-2-ylthio)-3-methylbut-2-enyl)cyclohexylcarbamate

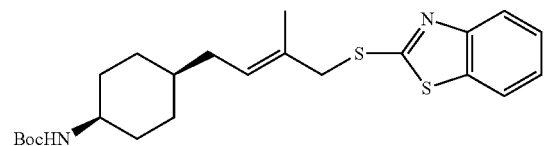 [SMILES: C/C(=C\C[C@H]1CC[C@@H](NC(=O)OC(C)(C)C)CC1)CSc1nc2ccccc2s1]

A solution of 2-mercaptobenzotiozol (407 mg) and Ph₃P (640 mg) in dry THF (5 mL) was stirred and cooled at 0° C. as alcohol (460 mg, from Example 7) in dry THF was added for 10 min. The DIAD (492 mg) in toluene was added slowly at the same temp. The resulting yellow suspension was stirred as TLC indicated that starting material was still there. Reaction was then allowed to warm to room temp and stirred overnight. The solvent was evaporated and diluted with hexane (mL) and filtered through celite pad. Purification of the crude by column chromatography (10% EtOAc in hexane) gave the corresponding thiol derivative (580 mg, 83%) as liquid. $^1$H NMR (400 MHz, CDCl₃) δ 7.79 (m, 1H), 7.67 (m, 1H), 7.34 (ddd, 1H, J=1.3, 7.3, 8.2 Hz), 7.22 (ddd, 1H, J=1.7, 5.4, 9.6 Hz), 5.47 (t, 1H, J=7.4 Hz), 4.53 (s, 1H), 3.91 (s, 2H), 3.60 (s, 1H), 1.87 (t, 2H, J=7.2 Hz), 1.69 (s, 3H), 1.50 (m, 2H), 1.37 (s, 14H), 1.02 (m, 2H); $^{13}$C NMR (CDCl₃, 100 MHz) δ 166.6, 155.2, 153.1, 135.3, 130.0, 129.1, 126.0, 124.3, 121.5, 120.9, 79.0, 46.3, 43.3, 36.3, 34.3, 29.7, 28.4, 27.6, 15.4.

9. Synthesis of tert-butyl (1S,4S)-4-((E)-4-(benzo[d]thiazol-2-ylsulfonyl)-3-methylbut-2-enyl)cyclohexylcarbamate

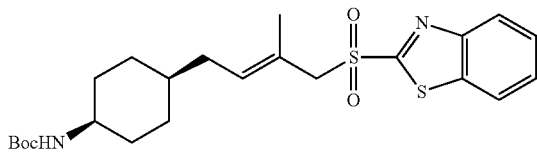 [SMILES: C/C(=C\C[C@H]1CC[C@@H](NC(=O)OC(C)(C)C)CC1)CS(=O)(=O)c1nc2ccccc2s1]

To a solution of thiol derivative (from Example 8, 140 mg) in EtOH (2 mL) were added Ammonium molybdate·4 H$_2$O (80 mg) and 30% H$_2$O$_2$ (0.36 mL) at 0° C. The resulting solution was stirred at room temp for 3 h. The mixture was quenched with 10% aq. potassium thiosulfate (mL). The product was extracted with EtOAc (3×20 mL) and washed with sat aq. NaHCO$_3$ (20 mL) and brine (20 mL), and dried over Na$_2$SO$_4$. The solvent was removed under reduced pressure to give crude that was purified on silica gel chromatography (30% EtOAc in hexane) to give sulfone derivative (105 mg, 70%) as white solid. $^1$H NMR (400 MHz, CDCl$_3$) δ 8.22 (d, 1H, J=8.0 Hz), 8.00 (d, 1H, J=7.8), 7.62 (m, 2H), 7.26 (s, 4H), 5.35 (s, 1H), 4.54 (m, 1H), 4.18 (s, 2H), 3.61 (s, 1H), 1.86 (m, 5H), 1.36 (m, 19H), 1.09 (s, 1H), 0.91 (d, 2H, J=10.5 Hz); $^{13}$C NMR (100 MHz, CDCl$_3$) δ 165.6, 152.7, 136.8, 136.5, 128.0, 127.7, 125.4, 122.7, 122.2, 79.0, 46.1, 36.1, 34.5, 29.6, 23.3, 16.9.

10. Synthesis of (S,Z)—N-((1S,4R)-4-((E)-4-(benzo[d]thiazol-2-ylsulfonyl)-3-methylbut-2-enyl)cyclohexyl)-4-(tert-butyldimethylsilyloxy)pent-2-enamide

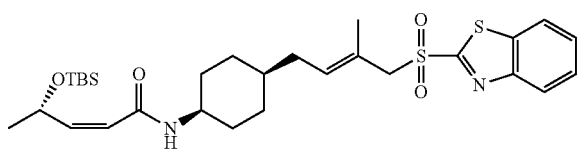 [SMILES: C/C(=C\C[C@H]1CC[C@@H](NC(=O)/C=C\[C@H](C)O[Si](C)(C)C(C)(C)C)CC1)CS(=O)(=O)c1nc2ccccc2s1]

A solution of sulfone derivative (100 mg, from Example 9) in DCM (2 mL) at 0° C. as 1:1 ratio of TFA/CH$_2$Cl$_2$ was added drop wise. The resulting solution was allowed to warm to room temp and stirred for 2 hours. The solvent was evaporated and put the residue for drying under vacuum. The crude amine salt was used in the next step without further purification. A solution of conjugated acid (17.22 mg) in dry CH$_3$CN (4 mL) at room temperature as HBTU (81 mg) and diisopropyl ethylamine (0.15 µl) were added sequentially. The above solution was transferred via needle canula into a solution containing amine derivative mg) in CH$_3$CN (4 mL). The resulting solution was the stirred for another 2 hours at room temperature at which time TLC showed the consumption of all starting material. The reaction was quenched with sat NH$_4$Cl (2 mL) and most of the organic solvent was removed in vacuo. The product was extracted with EtOAc (3×20 mL) and washed with water and brine (20 mL). Dried over Na$_2$SO$_4$ and concentrated the solvent to give residue that was purified by flash chromatography (30% EtOAc in hexane to obtain 88 mg (71% in two steps) of amide derivative as a liquid. $^1$H NMR and LC/MS are good. $^1$H NMR (400 MHz, CDCl$_3$) δ 8.21 (dd, 1H, J=1.3, 7.6), 8.00 (m, 1H), 7.61 (dtd, 2H, J=1.3, 7.2, 15.0), 5.96 (dd, 1H, J=7.8, 11.6), 5.72 (d, 1H, J=7.9), 5.55 (m, 2H), 5.44 (t, 1H, J=7.3), 4.18 (s, 2H), 3.99 (m, 1H), 1.95 (t, 2H, J=6.8), 1.83 (s, 3H), 1.52 (d, 2H, J=13.4), 1.37 (dd, 2H, J=7.1, 18.0), 1.26 (m, 7H), 1.05 (m, 2H), 0.86 (d, 9H, J=2.9), 0.03 (m, 6H); $^{13}$C NMR (100 MHz, CDCl$_3$) δ 165.7, 164.8, 152.7, 150.1, 136.8, 128.1, 127.7, 125.4, 122.6, 122.3, 119.8, 65.4, 64.6, 44.6, 36.1, 34.1, 29.4, 29.4, 27.1, 25.9, 23.8, 18.2, 17.0, 4.6, 4.7.

11. Synthesis of (S,Z)-4-(tert-butyldimmethylsilyloxy)-N-((1R,4R)-4-((2E,4E)-5-((3R,5S)-7,7-dimethyl-1,6-dioxaspiro[2.5]octan-5-yl)-3-methylpenta-2,4-dienyl)cyclohexyl)pent-2-enamide

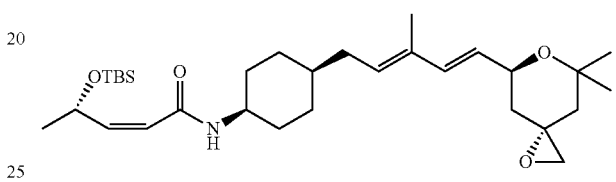

A solution of sulfone derivative (from Example 10, 75 mg) in dry THF (1.1 mL) was stirred and cooled at −78° C. as LiHMDS (0.26 mL, 1.0 M in t-butyl ether) was added drop wise. The solution was turned into orange color. After stirring for 10 min at the same temp, the aldehyde (17 mg) in dry THF (0.3 mL) was introduced to above solution. The resulting suspension was stirred at −78° C. for 1 h and allowed to warm room temp and stirred for over night. Sat NH$_4$Cl solution (3 mL) was added and the product was extracted with EtOAc (3×15 mL). The combined extracts were washed with brine (20 mL), and dried over Mg$_2$SO$_4$. The solvent was evaporated to give crude, which was purified on silica-gel chromatography (25% EtOAc in hexane) to give 15 mg of diene as liquid. $^1$H NMR (400 MHz, CDCl$_3$) δ 6.22 (d, 1H, J=15.7), 5.94 (dd, 1H, J=7.8, 11.6), 5.48 (ddt, 5H, J=8.1, 16.0, 23.6), 4.52 (m), 4.41 (m, 1H), 3.98 (s, 1H), 2.52 (s, 2H), 2.03 (t, 2H, J=7.2), 1.89 (m, 2H), 1.67 (s, 3H), 1.56 (d, 6H, J=10.1), 1.52 (s, 3H), 1.42 (s, 1H), 1.35 (s, 3H), 1.22 (m, 6H), 1.13 (m, 4H), 0.81 (d, 9H, J=8.9), −0.01 (d, 6H, J=5.3).

12. Synthesis of (S,Z)—N-((1R,4R)-4-((2E,4E)-5-((3R,5S)-7,7-dimethyl-1,6-dioxaspiro[2.5]octan-5-yl)-3-methylpenta-2,4-dienyl)cyclohexyl)-4-hydroxypent-2-enamide

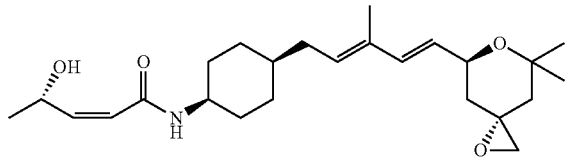 [SMILES: CC(/C=C/[C@@H]1C[C@]2(CO2)CC(C)(C)O1)=C\C[C@H]1CC[C@@H](NC(=O)/C=C\[C@H](C)O)CC1]

A solution of TBS protected diene (13 mg, from Example 11) in 1.0 mL of THF at 0° C. as TBAF (49 uL) was added. The yellow solution was stirred for 2 hours at room temp at which time the TLC was showed that all of starting material was disappeared. THF was evaporated and the residue was purified by silica-gel chromatography (60%-80% EtOAc in hexane (2×50 mL) to give the alcohol derivative (9.5 mg, 95%) as liquid. ¹H NMR (400 MHz, CDCl₃) δ 6.21 (d, 1H, J=15.7), 6.09 (dd, 1H, J=5.4, 11.9), 5.80 (s, 1H), 5.68 (dd, 1H, J=1.6, 12.0), 5.46 (m, 3H), 4.70 (s, 1H), 4.40 (m, 1H), 3.99 (s, 1H), 2.51 (s, 2H), 2.02 (t, 2H, J=7.3), 1.89 (m, 3H), 1.65 (s, 4H), 1.56 (d, 8H, J=14.1), 1.34 (s, 3H), 1.28 (d, 3H, J=6.7), 1.15 (m, 9H); ¹³C NMR (100 MHz, CDCl₃) δ 165.9, 150.0, 136.1, 134.1, 131.6, 127.1, 123.1, 73.0, 69.6, 55.7, 51.0, 45.8, 42.4, 38.6, 36.4, 34.1, 31.5, 29.2, 27.8, 27.7, 23.8, 22.8.

13. Synthesis of (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl acetate

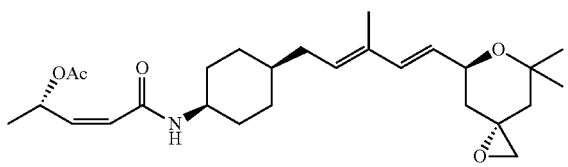 [SMILES: CC(=O)O[C@@H](C)/C=C\C(=O)N[C@H]1CC[C@@H](C/C=C(C)/C=C/[C@@H]2C[C@]3(CO3)CC(C)(C)O2)CC1]

A solution of alcohol (7 mg, from Example 12) in DCM (0.9 mL) at 0° C. as Et₃N (16 μL) and DMAP (2.0 mg) were sequentially added. After 5 minutes, Ac₂O (5.4 μL) was added using micro pipet. The solution was stirred for min at same temp. The solvent was evaporated and the residue was directly loaded on silica-gel column for purify and eluted with 50% EtOAc in hexane to give the acelated product (6.1 mg, 79%) as viscous oil. ¹H NMR (400 MHz, CDCl₃) δ 7.04 (s, 1H), 6.27 (d, 1H, J=15.7), 5.81 (dd, 2H, J=6.1, 17.7), 5.66 (dd, 1H, J=9.2, 11.6), 5.52 (m, 2H), 4.46 (m, 1H), 4.09 (s, 1H), 2.57 (s, 2H), 1.99 (m, 7H), 1.72 (s, 4H), 1.61 (s, 9H), 1.40 (s, 3H), 1.36 (d, 3H, J=6.4), 1.28 (s, 4H), 1.24 (d, 3H, J=8.3), 1.17 (m, 3H); ¹³C NMR (100 MHz, CDCl₃) δ 171.1, 164.8, 137.9, 136.2, 133.8, 131.9, 126.9, 125.4, 73.0, 69.6, 69.2, 55.6, 51.0, 45.5, 42.4, 38.6, 36.4, 34.2, 31.5, 29.4, 27.8, 27.6, 23.7, 21.2, 20.3, 12.4.

14. Synthesis of (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl isobutyrate (15)

A solution of alcohol derivative 14 (215 mg, 0.52 mmol) in CH₂Cl₂ (5 mL) was stirred and cooled at 0° C. as Et₃N (0.36 mL, 2.63 mmol) and DMAP (12 mg, 0.10 mmol) were sequentially added. After 5 min, isobutyryl chloride (0.16 mL, 1.58 mmol) was added drop-wise. The resulting solution was allowed to stir for 30 min at the same temp. The reaction mixture was diluted with water (10 mL) and CH₂Cl₂ (30 mL). The organic layer was separated and the aqueous layer was again extracted with CH₂Cl₂ (2×15 mL). The combined organic layers were washed with saturated aqueous NaHCO₃ (20 mL) and brine (20 mL), and dried over Na₂SO₄. The solvent was evaporated and the crude residue was purified by silica-gel chromatography (30% ethyl acetate in hexane) to give 215 mg (84%) of 15 as white viscous solid. ¹H NMR (400 MHz, CDCl₃) δ 7.25 (d, J=5.2 Hz, 1H), 6.27 (d, J=15.7 Hz, 1H), 5.78 (d, 11.8 Hz, 1H), 5.78-5.72 (m, 1H), 5.63 (dd, J=11.8, 9.1 Hz, 1H), 5.55 (dd, J=15.7, 6.7 Hz, 1H), 5.49 (t, J=7.5 Hz, 1H), 4.50-4.42 (m, 1H), 4.16-4.09 (m, 1H), 2.57 (s, 2H), 2.58-2.49 (m, 1H), 2.12-2.04 (d, J=14.2 Hz, 2H), 2.03-1.86 (m, 2H), 1.72 (s, 3H). 1.72-1.66 (m, 1H), 1.64-1.54 (m, 6H), 1.40 (s, 3H), 1.36 (d, J=6.4 Hz, 3H), 1.28 (s, 3H), 1.25-1.19 (m, 3H) 1.17 (d, J=7.0 Hz, 6H), 1.14 (d, J=2.0 Hz, 1H); ¹³C NMR (100 MHz, CDCl₃) δ 177.36, 164.87, 137.59, 136.22, 133.77, 132.06, 126.97, 125.62, 73.04, 69.59, 68.97, 55.69, 51.05, 45.31, 42.46, 38.64, 36.60, 34.44, 34.00, 31.55, 29.58, 29.47, 27.84, 27.54, 23.77, 20.30, 18.98, 18.86, 12.49; IR (Neat Film) 3314, 2973, 2931, 2856, 1733, 1688, 1628, 1533, 1450, 1368, 1241, 1195, 1047 cm⁻¹; MS (ESI) m/z 488.6 (M+1)⁺; HRMS (ESI) m/z Calcd for C₂₉H₄₆NO₅ (M+1)⁺ 488.3376. found 488.3376.

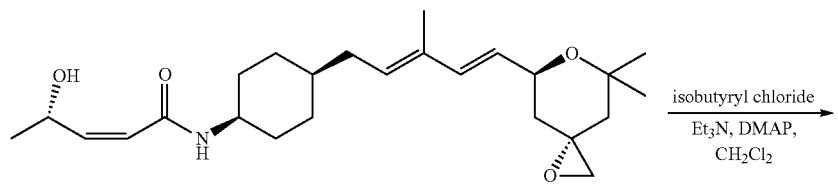

14

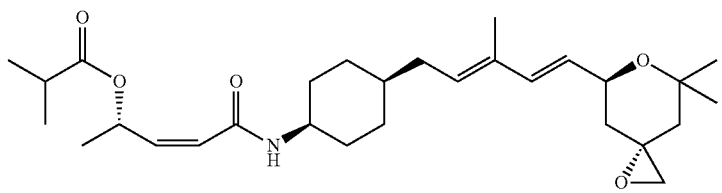

15

15. Synthesis of (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl 1-methylpiperidine-4-carboxylate (16)

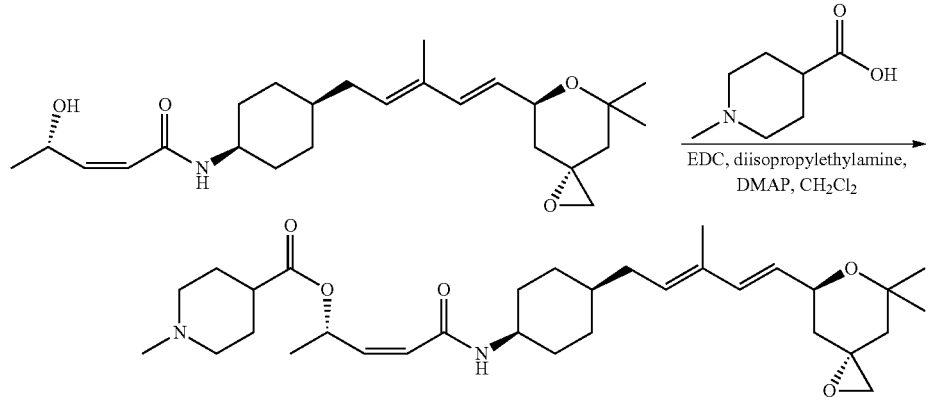

16

A solution of alcohol derivative 14 (10 mg, 0.024 mmol) in $CH_2Cl_2$ (0.22 mL) was treated with 1-methylpiperidine-4-carboxylic acid (9.3 mg, 0.065 mmol) diisopropylethylamine (13 μL, 0.072 mmol), DMAP (7.3 mg, 0.06 mmol). The reaction solution was cooled to 0° C. as treated with EDC (11.4 mg, 0.06 mmol). The resulting suspension was allowed to stir at room temperature for overnight. Saturated aqueous $NH_4Cl$ (1 mL) was added and the product was extracted with $CH_2Cl_2$ (2×5 mL). The combined organic layers were washed with saturated aqueous $NaHCO_3$ (3 mL) and brine (3 mL), and dried over $Na_2SO_4$. Concentrated and the residue was purified by silica column (5% MeOH in $CHCl_3$ w/0.2% $Et_3N$) to give 5 mg (39%) of 16 as a viscous liquid. $^1H$ NMR (400 MHz, $CDCl_3$) δ 7.04 (bd, 1H), 6.27 (d, J=15.7 Hz, 1H), 5.90-5.74 (m, 2H), 5.71-5.42 (m, 3H), 4.46 (ddd, J=11.1, 6.7, 1.8 Hz, 1H), 4.12 (m, 1H), 2.82 (d, J=11.5 Hz, 2H), 2.57 (s, 2H), 2.28 (s, 4H), 2.12-1.90 (m, 9H), 1.72 (s, 3H), 1.70-1.66 (m, 2H); 1.64-1.54 (m, 6H), 1.40 (s, 3H), 1.34 (d, 3H), 1.27 (s, 3H), 1.26-1.12 (m, 4H); $^{13}C$ NMR (101 MHz, $CDCl_3$) δ 175.07, 164.78, 138.02, 136.22, 133.80, 132.02, 127.00, 125.50, 77.35, 77.23, 77.03, 76.71, 73.05, 69.61, 69.17, 55.70, 54.81, 51.06, 46.28, 45.86, 45.37, 42.47, 38.65, 36.60, 34.42, 31.55, 29.55, 29.44, 28.07, 27.87, 27.60, 23.78, 20.27, 12.52; IR (Neat Film) 3284, 2927, 2853, 1729, 1666, 1628, 1533, 1449, 1374, 1218, 1182, 1047 $cm^{-1}$; MS (ESI) m/z 543 $(M+1)^+$; HRMS (ESI) m/z Calcd for $C_{32}H_{51}N_2O_5$ $(M+1)^+$ 543.3798. found 543.3784.

16. Preparation of Ester Derivatives from Alcohol Using a Variety of Acid Chlorides

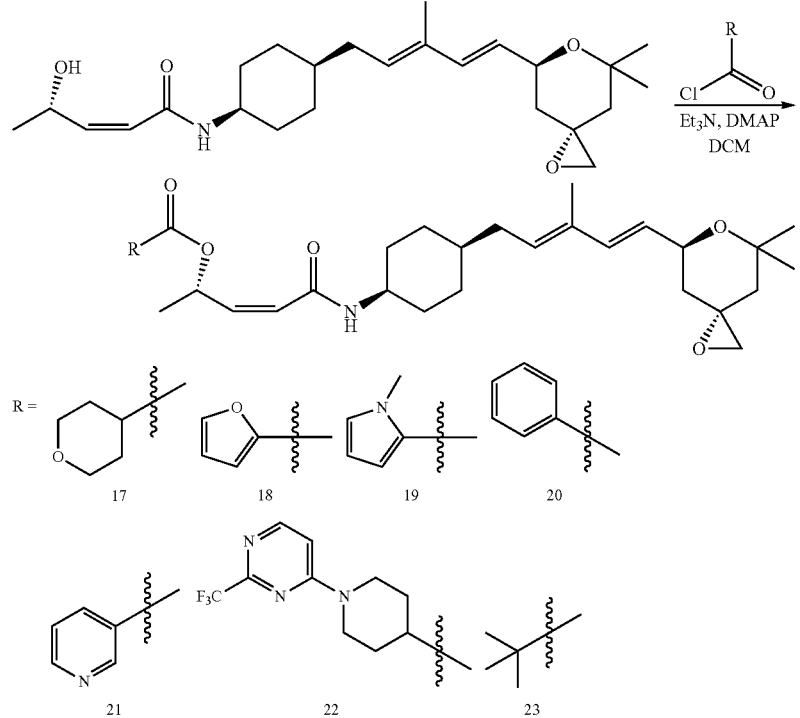

A stirred solution of alcohol derivative 14 (10 mg, 0.52 mmol) in CH$_2$Cl$_2$ (0.5 mL) at 0° C. was treated with Et$_3$N (16.6 μL, 0.12 mmol) and DMAP (4.8 μL, 0.10 mmol, 0.5M in CH$_2$Cl$_2$) sequentially. After 5 min at 0° C., appropriate acid chloride (0.07 mmol) was added drop-wise. The resulting solution was allowed to stir for 1 h at the same temp. The reaction mixture was diluted with water (3 mL) and CH$_2$Cl$_2$ (6 mL). The aqueous layer was extracted with CH$_2$Cl$_2$ (2×5 mL). The combined organic layers were washed with saturated aqueous NaHCO$_3$ (3 mL) and brine (3 mL), and dried over Na$_2$SO$_4$. The solvent was evaporated and the crude residues were purified by silica-gel chromatography (ethyl acetate in hexane) to give corresponding ester derivative.

17. (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl tetrahydro-2H-pyran-4-carboxylate (17)

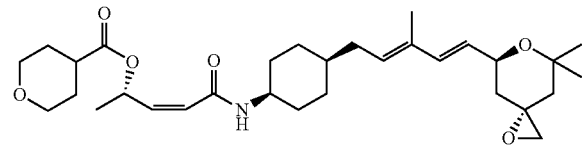 [SMILES: CC(/C=C/[C@@H]1C[C@]2(CO2)CC(C)(C)O1)=C\C[C@H]1CC[C@@H](NC(=O)/C=C\[C@H](C)OC(=O)C2CCOCC2)CC1]

Yield: 8 mg (63%) as viscous oil. $^1$H NMR (400 MHz, CDCl$_3$) δ 7.00 (d, J=7.7 Hz, 1H), 6.27 (d, J=15.7 Hz, 1H), 5.93-5.83 (m, 1H), 5.80 (d, J=11.7 Hz, 1H), 5.65 (dd, J=11.7, 8.9 Hz, 1H), 5.55 (dd, J=15.7, 6.7 Hz, 1H), 5.48 (t, J=7.5 Hz, 1H), 4.52-4.40 (m, 1H), 4.11 (s, 1H), 3.96 (dt, J=11.6, 3.6 Hz, 2H), 3.43 (td, J=11.3, 2.9 Hz, 2H), 2.57 (s, 2H), 2.56-2.47 (m, 1H), 2.10-2.04 (m, 2H), 2.02-1.87 (m, 2H), 1.86-1.74 (m, 4H), 1.72 (s, 3H), 1.71-1.65 (m, 1H), 1.64-1.55 (m, 6H), 1.40 (s, 3H), 1.37 (d, J=6.5 Hz, 3H), 1.28 (s, 3H), 1.26-1.12 (m, 4H); $^{13}$C NMR (101 MHz, CDCl$_3$) δ 174.60, 164.71, 138.11, 136.19, 133.81, 131.97, 127.05, 125.45, 73.05, 69.60, 69.30, 67.04, 67.02, 55.69, 51.05, 45.38, 42.46, 40.14, 38.64, 36.56, 34.42, 31.55, 29.72, 29.54, 28.64, 28.59, 27.88, 27.60, 23.78, 20.25, 12.52; MS (ESI) m/z 530.5 (M+1)$^+$; IR (Neat Film) 3319, 2927, 2853, 1731, 1668, 1629, 1533, 1447, 1378, 1184, 1093, 1046 cm$^{-1}$; HRMS (ESI) m/z Calcd for C$_{31}$H$_{48}$NO$_6$ (M+1)$^+$ 530.3482. found 530.3481.

18. (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl furan-2-carboxylate (18)

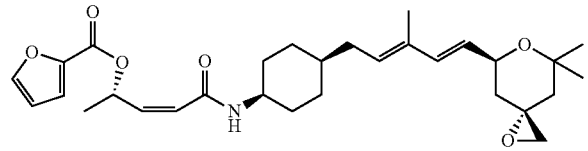 [SMILES: CC(/C=C/[C@@H]1C[C@]2(CO2)CC(C)(C)O1)=C\C[C@H]1CC[C@@H](NC(=O)/C=C\[C@H](C)OC(=O)c2ccco2)CC1]

Yield: 8 mg (65.3%) as viscous oil. $^1$H NMR (400 MHz, CDCl$_3$) δ 7.59 (dd, J=1.7, 0.9 Hz, 1H), 7.20 (dd, J=3.5, 0.8 Hz, 1H), 6.98 (d, J=7.6 Hz, 1H), 6.52 (dd, J=3.5 Hz, 1.7, 1H), 6.26 (d, J=15.7 Hz, 1H), 6.09 (dd, J=8.2, 6.5 Hz, 1H), 5.82 (dt, J=11.7, 10.0 Hz, 2H), 5.59-5.45 (m, 2H), 4.45 (ddd, J=10.9, 6.7, 1.8 Hz, 1H), 4.18-4.07 (m, 2H), 2.57 (s, 2H), 2.15-2.06 (m, 2H), 2.03-1.87 (m, 2H), 1.71 (s, 4H), 1.67-1.56 (m, 6H), 1.50 (d, J=6.5 Hz, 3H), 1.40 (s, 3H), 1.29-1.26 (m, 5H), 1.24-1.12 (m, 2H); $^{13}$C NMR (101 MHz, CDCl$_3$) δ 164.76, 158.57, 146.55, 144.53, 137.88, 136.25, 133.84, 132.01, 126.98, 125.62, 118.44, 111.96, 77.35, 77.03, 76.71, 73.04, 69.99, 69.63, 55.69, 51.05, 45.58, 42.47, 38.64, 36.43, 31.55, 29.73, 29.50, 29.38, 27.88, 27.63, 23.79, 20.40, 12.48; IR (Neat Film) 3320, 2924, 2853, 1715, 1668, 1629, 1532, 1473, 1309, 1181, 1118, 1045 cm$^{-1}$; MS (ESI) m/z 512 (M+1)$^+$; HRMS (ESI) m/z Calcd for C$_{30}$H$_{42}$NO$_6$ (M+1)$^+$ 512.3012. found 522.3007.

19. (S,Z)-5-((1R,4R)-4-((2E,4E)-5-((3R,5S)-7,7-Dimethyl-1,6-dioxaspiro[2.5]octan-5-yl)-3-methylpenta-2,4-dienyl)cyclohexylamino)-5-oxopent-3-en-2-yl 1-methyl-1H-pyrrole-2-carboxylate (19)

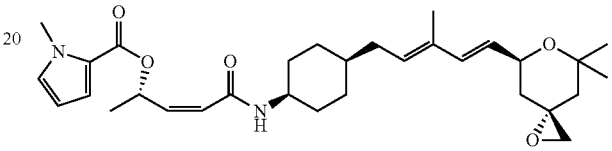

Yield: 7 mg (56%) as viscous oil. $^1$H NMR (400 MHz, CDCl$_3$) δ 7.54 (d, J=7.8 Hz, 1H), 6.98 (dd, J=4.0, 1.8 Hz, 1H), 6.80 (t, J=2.1 Hz, 1H), 6.25 (d, J=15.7 Hz, 1H), 6.12 (dd, J=4.0, 2.5 Hz, 1H), 5.95-5.87 (m, 1H), 5.85-5.71 (m, 2H), 5.56-5.46 (m, 2H), 4.52-4.38 (m, 1H), 4.16 (s, 1H), 3.91 (s, 3H), 2.57 (s, 2H), 2.13-1.83 (m, 4H), 1.80-1.75 (m, 1H), 1.69 (s, 3H), 1.65-1.55 (m, 6H), 1.45 (d, J=6.5 Hz, 3H), 1.40 (s, 3H), 1.28 (s, 3H), 1.26-1.24 (m, 2H), 1.23-1.14 (m, 2H); $^{13}$C NMR (101 MHz, CDCl$_3$) δ 165.04, 161.38, 137.59, 136.19, 133.75, 131.98, 130.04, 127.03, 125.61, 122.13, 118.46, 108.07, 73.05, 69.61, 68.67, 55.68, 51.05, 45.20, 42.47, 38.64, 36.89, 36.80, 31.55, 29.73, 29.68, 29.56, 27.95, 27.64, 23.79, 20.53, 12.47; IR (Neat Film) 3318, 2923, 2852, 1703, 1667, 1628, 1530, 1412, 1245, 1047 cm$^{-1}$; MS (ESI) m/z 525 (M+1)$^+$; HRMS (ESI) m/z Calcd for C$_{31}$H$_{45}$N$_2$O$_5$ (M+1)$^+$ 525.3328. found 525.3320.

20. (S,Z)-5-((1R,4R)-4-((2E,4E)-5-((3R,5S)-7,7-dimethyl-1,6-dioxaspiro[2.5]octan-5-yl)-3-methylpenta-2,4-dienyl)cyclohexylamino)-5-oxopent-3-en-2-yl benzoate (20)

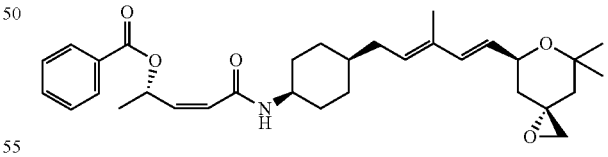

Yield: 8 mg (64%) as viscous oil. $^1$H NMR (400 MHz, CDCl$_3$) δ 8.08-8.02 (m, 2H), 7.62-7.55 (m, 1H), 7.45 (dd, J=10.6, 4.8 Hz, 2H), 7.32 (d, J=7.8 Hz, 1H), 6.26 (d, J=15.7 Hz, 1H), 6.05 (dd, J=8.8, 6.5 Hz, 1H), 5.81 (dt, J=11.7, 10.4 Hz, 2H), 5.59-5.46 (m, 2H), 4.44 (ddd, J=11.0, 6.7, 1.9 Hz, 1H), 4.16 (s, 1H), 2.57 (s, 2H), 2.10 (dd, J=11.2, 7.2 Hz, 2H), 2.03-1.86 (m, 2H), 1.82-1.68 (m, 2H), 1.68-1.58 (m, 6H), 1.52 (d, J=6.5, 3H), 1.40 (s, 3H), 1.38-1.10 (m, 9H) $^{13}$C NMR (101 MHz, CDCl$_3$) δ 166.62, 164.90, 137.56, 136.23, 133.81, 133.27, 132.03, 129.98, 129.67, 128.44, 126.99, 125.80, 73.04, 69.86, 69.61, 55.69, 51.05, 45.39, 42.47, 38.63, 36.62, d 31.55, 29.73, 29.62, 29.51, 27.86, 27.58, 23.79, 20.45, 12.49; IR (Neat Film) 3317, 2924, 2853, 1718, 1668, 1627, 1533, 1451, 1325, 1269, 1195, 1046 cm$^{-1}$; MS (ESI) m/z 522 (M+1)$^+$; HRMS (ESI) m/z Calcd for $C_{32}H_{44}NO_5$ (M+1)$^+$ 522.3219. found 522.3209.

21. (S,Z)-5-((1R,4R)-4-((2E,4E)-5-((3R,5S)-7,7-dimethyl-1,6-dioxaspiro[2.5]octan-5-yl)-3-methyl-penta-2,4-dienyl)cyclohexylamino)-5-oxopent-3-en-2-yl nicotinate (21)

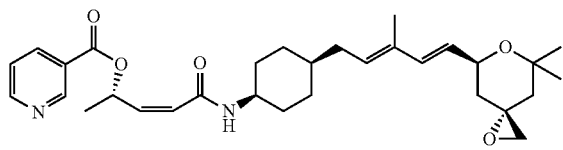 [SMILES: CC(/C=C/[C@@H]1C[C@]2(CO2)CC(C)(C)O1)=C\C[C@H]1CC[C@@H](NC(=O)/C=C\[C@H](C)OC(=O)c2cccnc2)CC1]

Yield: 3 mg (24%) as white solid. $^1$H NMR (400 MHz, CDCl$_3$) δ 9.23 (dd, J=2.2, 0.8 Hz, 1H), 8.79 (dd, J=4.9, 1.7 Hz, 1H), 8.34-8.25 (m, 1H), 7.40 (ddd, J=8.0, 4.9, 0.9 Hz, 1H), 6.83 (d, J=7.5 Hz, 1H), 6.25 (dd, J=11.7, 8.5 Hz, 2H), 5.89-5.82 (m, 2H), 5.62-5.43 (m, 2H), 4.53-4.40 (m, 1H), 4.14 (s, 1H), 2.57 (s, 2H), 2.12-2.06 (m, 2H), 2.03-1.86 (m, 2H), 1.75-1.70 (m, 1H), 1.67-1.58 (5H), 1.54 (d, J=6.5 Hz, 3H), 1.40 (s, 3H), 1.32-1.24 (m, 5H), 1.24-1.12 (m, 2H); IR (Neat Film) 3333, 2921, 2851, 1723, 1667, 1628, 1534, 1327, 1275, 1119, 1045 cm$^{-1}$; MS (ESI) m/z 523 (M+1)$^+$; HRMS (ESI) m/z Calcd for $C_{31}H_{43}N_2O_5$ (M+1)$^+$ 523.3172. found 523.3148.

22. (S,Z)-5-((1R,4R)-4-((2E,4E)-5-((3R,5S)-7,7-dimethyl-1,6-dioxaspiro[2.5]octan-5-yl)-3-methyl-penta-2,4-dienyl)cyclohexylamino)-5-oxopent-3-en-2-yl 1-(2-(trifluoromethyl)pyrimidin-4-yl)piperidine-4-carboxylate (22)

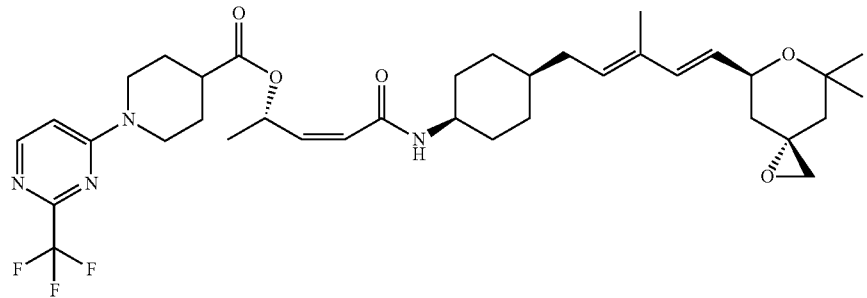 [SMILES: CC(/C=C/[C@@H]1C[C@]2(CO2)CC(C)(C)O1)=C\C[C@H]1CC[C@@H](NC(=O)/C=C\[C@H](C)OC(=O)C2CCN(c3ccnc(C(F)(F)F)n3)CC2)CC1]

Yield: 9 mg (56%) as white solid. $^1$H NMR (400 MHz, CDCl$_3$) δ 8.48 (d, J=4.8 Hz, 1H), 6.97 (d, J=7.7 Hz, 1H), 6.73 (d, J=4.8 Hz, 1H), 6.26 (d, J=15.7 Hz, 1H), 5.88 (dt, J=12.7, 6.3 Hz, 1H), 5.80 (dd, J=11.7, 0.7 Hz, 1H), 5.66 (dd, J=11.7, 8.9 Hz, 1H), 5.54 (dd, J=15.7, 6.7 Hz, 1H), 5.47 (t, J=7.5 Hz, 1H), 4.67 (dd, J=9.5, 4.0 Hz, 2H), 4.46 (ddd, J=11.1, 6.8, 2.1 Hz, 1H), 4.10 (s, 1H), 3.19-3.05 (m, 2H), 2.67-2.55 (m, 3H), 2.06 (td, J=7.3, 2.9 Hz, 2H), 2.03-1.87 (m, 4H), 1.78-1.65 (m, 7H), 1.64-1.54 (m, 5H), 1.42-1.35 (m, 6H), 1.28 (s, 3H), 1.25-1.11 (m, 4H); $^{13}$C NMR (101 MHz, CDCl$_3$) δ 174.64, 164.67, 161.40, 161.35, 160.10, 156.46, 156.12, 138.11, 136.16, 133.81, 131.95, 127.04, 125.46, 104.43, 73.04, 69.58, 69.37, 55.69, 51.06, 45.39, 43.09, 43.07, 42.47, 41.32, 38.64, 36.55, 34.40, 31.55, 29.53, 29.42, 27.89, 27.86, 27.79, 27.61, 23.78, 20.26, 12.48; IR (Neat Film) 3328, 2930, 2857, 1729, 1667, 1627, 1592, 1523, 1449, 1329, 1243, 1132, 1046 cm$^{-1}$; MS (ESI) m/z 675 (M+1)$^+$; HRMS (ESI) m/z Calcd for $C_{36}H_{50}N_4O_5F_3$ (M+1)$^+$ 675.3733. found 675.3721.

23. (S,Z)-5-((1R,4R)-4-((2E,4E)-5-((3R,5S)-7,7-dimethyl-1,6-dioxaspiro[2.5]octan-5-yl)-3-methyl-penta-2,4-dienyl)cyclohexylamino)-5-oxopent-3-en-2-yl pivalate

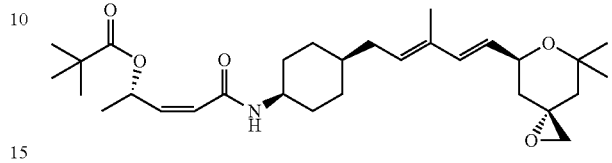

Yield: 7 mg (58%) as viscous oil. $^1$H NMR (400 MHz, CDCl$_3$) δ 7.35 (d, J=7.9 Hz, 1H), 6.27 (d, J=15.7 Hz, 1H), 5.81 (d, J=11.7 Hz, 1H), 5.73 (tt, J=12.7, 6.1 Hz, 1H), 5.61 (dd, J=11.7, 9.2 Hz, 2H), 5.49 (t, J=7.4 Hz, 1H), 4.46 (ddd, J=11.1, 6.7, 1.8 Hz, 1H), 4.14 (d, J=3.9 Hz, 1H), 2.57 (s, 2H), 2.11-2.04 (m, 2H), 2.02-1.88 (m, 3H), 1.75-1.68 (m, 5H), 1.65-1.55 (m, 5H), 1.40 (s, 3H), 1.36 (d, J=6.4 Hz, 3H), 1.32-1.22 (m, 14H); $^{13}$C NMR (101 MHz, CDCl$_3$) δ 178.82, 164.89, 137.40, 136.24, 133.77, 132.09, 126.98, 125.73, 73.05, 69.60, 69.02, 55.69, 51.05, 45.23, 42.47, 38.69, 38.64, 36.67, 34.53, 31.55, 29.73, 29.64, 29.52, 27.84, 27.54, 27.11, 23.78, 20.24, 12.51; IR (Neat Film) 3320, 2924, 2931, 2853, 1728, 1668, 1627, 1533, 1479, 1396, 1278, 1163, 1048 cm$^{-1}$; MS (ESI) m/z 502 (M+1)+; HRMS (ESI) m/z Calcd for $C_{31}H_5ON_3O_5$ (M+1)+ 502.3532. found 502.3518.

24. (S,Z)-5-((1R,4R)-4-((2E,4E)-5-((3R,5S)-7,7-dimethyl-1,6-dioxaspiro[2.5]octan-5-yl)-3-methyl-penta-2,4-dienyl)cyclohexylamino)-5-oxopent-3-en-2-yl 4-nitrophenyl carbonate (Activated Carbonate)

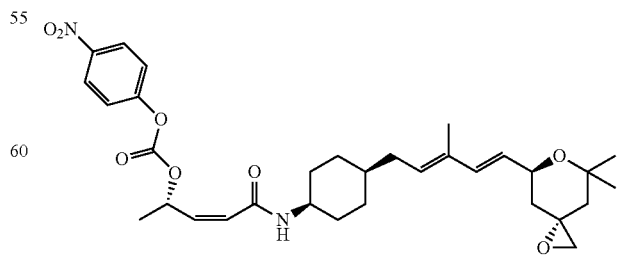

A stirred solution of alcohol 14 (45 mg, 0.108 mmol) in anhyd CH$_2$Cl$_2$ (2 mL) was treated with Et$_3$N (30 μL, 0.21 mmol) and 4-nitrophenyl chloroformate (32.6 mg, 0.16 mmol) at room temperature. The resulting light yellow suspension was allowed to stir for 4 h at room temperature. This mixture was then diluted with $CH_2Cl_2$ (20 mL) and washed with aqueous 1N HCl (8 mL), saturated aqueous $NaHCO_3$ (8 mL) and brine (8 mL), and dried over $Na_2SO_4$. Concentration and purification of the residue by silica-gel chromatography (30-40% ethyl acetate in hexane) gave 36 mg (57%) of the desired compound as a liquid; $^1H$ NMR (400 MHz, $CDCl_3$) δ 8.33-8.20 (m, 8H), 8.31-8.22 (m, 8H), 7.45-7.32 (m, 8H), 7.42-7.35 (m, 8H), 7.26 (s, 10H), 6.37-6.19 (m, 8H), 6.37-6.21 (m, 7H), 6.05 (d, J=7.7 Hz, 3H), 5.97 (dd, J=11.6, 8.1 Hz, 5H), 6.12-5.78 (m, 12H), 5.84 (dd, J=11.6, 1.0 Hz, 4H), 5.55 (dd, J=15.7, 6.7 Hz, 3H), 5.62-5.39 (m, 7H), 5.45 (s, 3H), 4.46 (s, 4H), 4.46 (s, 4H), 4.10 (dd, J=15.4, 8.2 Hz, 6H), 4.12-4.00 (m, 5H), 2.57 (s, 6H), 2.57 (d, J=3.6 Hz, 8H), 2.56 (s, 1H), 2.11-1.84 (m, 18H), 2.10-1.85 (m, 18H), 1.74-1.51 (m, 59H), 1.40 (s, 10H), 1.76-1.07 (m, 117H), 1.32-1.08 (m, 39H), 0.85 (dd, J=11.2, 7.2, 4H); MS (ESI) m/z 605 (M+Na)$^+$.

25. Preparation of Carbamate Analogs 26. (S,Z)-5-((1R,4R)-4-((2E,4E)-5-((3R,5S)-7,7-dimethyl-1,6-dioxaspiro[2.5]octan-5-yl)-3-methyl-penta-2,4-dienyl)cyclohexylamino)-5-oxopent-3-en-2-yl 4-cycloheptylpiperazine-1-carboxylate (24)

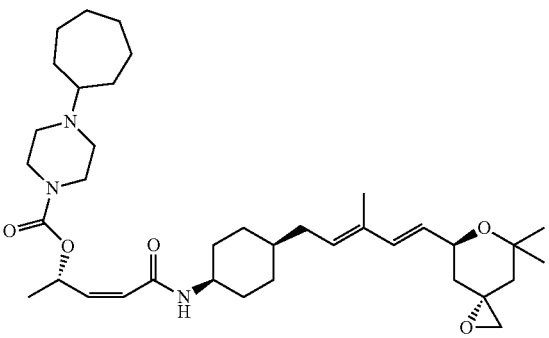 [SMILES: CC(/C=C/[C@@H]1C[C@]2(CO2)CC(C)(C)O1)=C\C[C@H]1CC[C@@H](NC(=O)/C=C\[C@H](C)OC(=O)N2CCN(C3CCCCCC3)CC2)CC1]

A solution of activated carbonate 23 (4.2 mg, 7.21 μmol) in 1,2 dichloroethane (0.2 mL) was stirred at room temperature as 1-cycloheptyl piperizine (0.21 mL, 0.02 mmol, 0.1M stock solution) was added. The resulting solution was stirred for 1

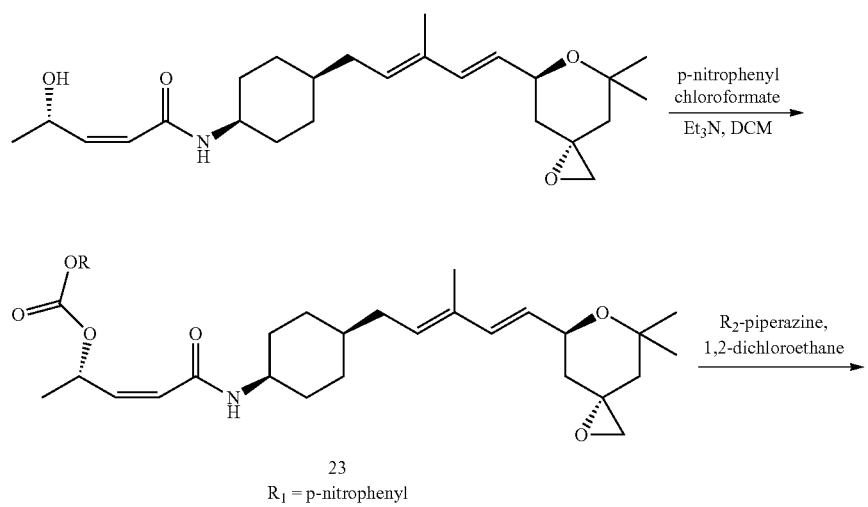

23
$R_1$ = p-nitrophenyl

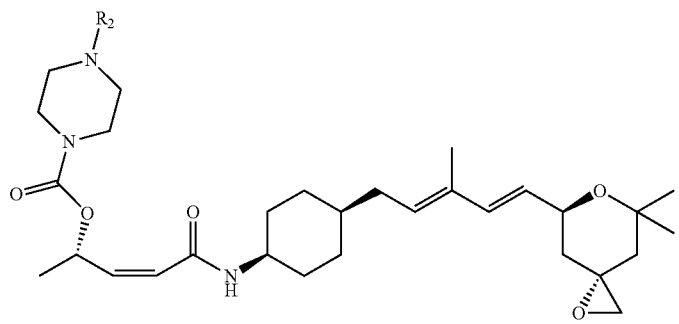

24: $R_1$ = cycloheptyl
25: $R_1$ = 3-methoxyphenyl
26: $R_1$ = methyl
27: $R_1$ = 2-hydroxyethane h 15 min and the solvent was removed under vacuum. The crude was purified by Pre-SFC (30% MeOH_OD-H) to give 1.8 mg of carbamate derivative as viscous oil. Purified again by a small silica-gel column using 2-3% MeOH in CH$_2$Cl$_2$ (50 mL and 75 mL) to give 1.13 mg of 24 as viscous oil. $^1$H NMR (400 MHz, CDCl$_3$) δ 8.22-8.08 (m, 1H), 6.27 (d, J=15.7 Hz, 1H), 5.82 (d, J=11.2, 1H), 5.59 (d, J=11.1 Hz, 4H), 4.55-4.40 (m, 1H), 4.20-4.07 (m, 1H), 3.46 (s, 4H), 2.57 (s, 2H), 2.49 (s, 3H), 2.08 (s, 2H), 1.99 (d, J=13.9 Hz, 2H), 1.78 (s, 2H), 1.72 (s, 4H), 1.59 (s, 20H), 1.40 (s, 5H), 1.34 (d, J=6.0 Hz, 4H), 1.28 (s, 3H), 1.25 (s, 4H). IR (Neat Film) 3300, 2926, 2855, 1668, 1535, 1434, 1372, 1244, 1121, 1049 cm$^{-1}$; MS (ESI) m/z 627 (M+1)$^+$; HRMS (ESI) m/z Calcd for C$_{37}$H$_{60}$N$_3$O$_5$ (M+1)$^+$ 626.4533. found 626.4526.

27. (S,Z)-5-((1R,4R)-4-((2E,4E)-5-((3R,5S)-7,7-dimethyl-1,6-dioxaspiro[2.5]octan-5-yl)-3-methyl-penta-2,4-dienyl)cyclohexylamino)-5-oxopent-3-en-2-yl 4-(3-methoxyphenyl)piperazine-1-carboxylate (25)

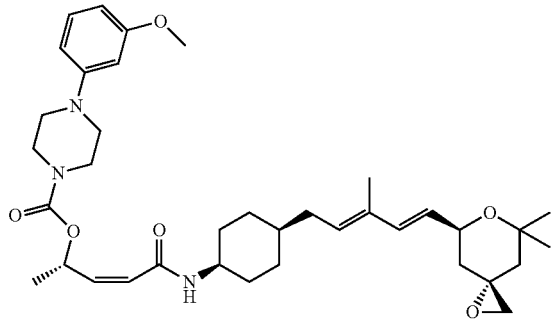 [SMILES: COc1cccc(N2CCN(C(=O)O[C@@H](C)/C=C\C(=O)N[C@H]3CC[C@@H](C/C=C(C)/C=C/[C@@H]4C[C@]5(CO5)CC(C)(C)O4)CC3)CC2)c1]

Yield: 3 mg (46%) as viscous oil. $^1$H NMR (400 MHz, CDCl$_3$) δ 7.98 (d, J=7.9, 1H), 7.19 (s, 1H), 6.54 (dd, J=7.9, 1.7 Hz, 1H), 6.50-6.43 (m, 2H), 6.27 (d, J=15.7 Hz, 1H), 5.84 (d, J=10.9 Hz, 1H), 5.70-5.61 (m, 2H), 5.52 (ddd, J=26.0, 17.2, 9.0 Hz, 2H), 4.53-4.40 (m, 1H), 4.12 (d, J=7.1 Hz, 1H), 3.80 (s, 3H), 3.63 (s, 4H), 3.15 (s, 4H), 2.56 (d, J=7.0 Hz, 2H), 2.08 (dd, J=11.5, 7.2 Hz, 2H), 2.02 (dd, J=25.4, 10.0 Hz, 3H), 1.72 (s, 4H), 1.59 (d, J=12.1 Hz, 17H), 1.38 (dd, J=8.2, 5.6 Hz, 7H), 1.31-1.13 (m, 8H); $^{13}$C NMR (101 MHz, CDCl$_3$) δ 165.05, 160.64, 155.17, 152.27, 136.64, 136.24, 133.74, 132.24, 129.96, 126.94, 126.23, 109.45, 105.22, 103.27, 73.05, 69.94, 69.63, 55.70, 55.25, 54.05, 51.06, 49.31, 45.35, 43.10, 42.47, 38.65, 36.61, 34.54, 31.55, 29.62, 27.48, 23.79, 20.64, 12.52.

28. (S,Z)-5-((1R,4R)-4-((2E,4E)-5-((3R,5S)-7,7-dimethyl-1,6-dioxaspiro[2.5]octan-5-yl)-3-methyl-penta-2,4-dienyl)cyclohexylamino)-5-oxopent-3-en-2-yl 4-methylpiperazine-1-carboxylate (26)

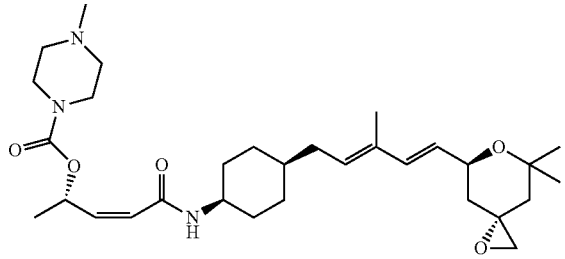 [SMILES: CC(/C=C/[C@@H]1C[C@]2(CO2)CC(C)(C)O1)=C\C[C@H]1CC[C@@H](NC(=O)/C=C\[C@H](C)OC(=O)N2CCN(C)CC2)CC1]

A solution of activated carbonate 23 (6 mg, 10.3 μmol) in 1,2 dichloroethane (0.2 mL) was stirred at room temperature as 1-methylpiperazine (31 μL, 0.03 mmol, 1M stock solution) was added. The resulting solution was stirred for 1 h and the solvent was removed under vacuum. The crude was purified by silica-gel column (2-3% MeOH in CHCl$_3$) to give 2.5 mg of 26 as viscous oil. $^1$H NMR (400 MHz, CDCl$_3$) δ 8.07 (d, J=7.9, 1H), 6.27 (d, J=15.7 Hz, 1H), 5.83 (d, J=10.9, 1H), 5.56 (ddd, J=24.5, 18.0, 9.1 Hz, 4H), 4.52-4.41 (m, 1H), 4.14 (s, 1H), 3.50 (s, 4H), 2.56 (d, J=7.2 Hz, 2H), 2.37 (t, J=4.7 Hz, 4H), 2.31 (s, 3H), 2.07 (d, J=3.1 Hz, 2H), 1.99 (d, J=13.9 Hz, 1H), 1.92 (dd, J=13.7, 11.7 Hz, 1H), 1.73 (d, J=14.6 Hz, 5H), 1.58 (d, J=11.8 Hz, 10H), 1.41 (d, J=6.8 Hz, 3H), 1.35 (d, J=6.1 Hz, 4H), 1.28 (s, 3H), 1.27-1.12 (m, 5H); $^{13}$C NMR (101 MHz, CDCl$_3$) δ 165.09, 155.18, 136.46, 136.26, 133.63, 132.29, 126.93, 126.27, 77.35, 77.23, 77.03, 76.71, 73.05, 69.76, 69.63, 55.69, 54.66, 51.06, 46.20, 42.47, 38.66, 31.55, 29.64, 29.49, 27.83, 27.48, 23.79, 20.64, 12.50; MS (ESI) m/z 544 (M+1)$^+$; HRMS (ESI) m/z Calcd for C$_{31}$H$_{50}$N$_3$O$_5$ (M+1)$^+$ 544.3750. found 544.3737.

29. (S,Z)-5-((1R,4R)-4-((2E,4E)-5-((3R,5S)-7,7-dimethyl-1,6-dioxaspiro[2.5]octan-5-yl)-3-methyl-penta-2,4-dienyl)cyclohexylamino)-5-oxopent-3-en-2-yl 4-(2-hydroxyethyl)piperazine-1-carboxylate (27)

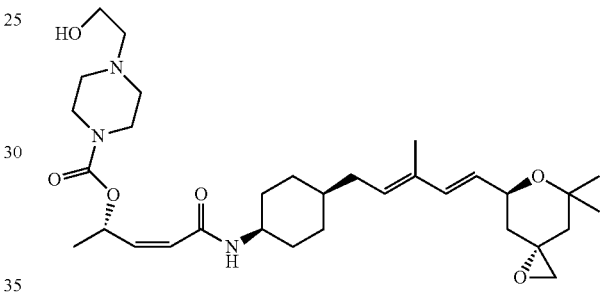

A solution of activated carbonate 23 (2 mg, 2.3 μmol) in 1,2 dichloroethane (0.2 mL) was stirred at room temperature as 1-hydroxyethyl 1piperazine (10 μL, 10.3 μmol, 1M stock solution) was added. The resulting solution was stirred for 1 h and the solvent was removed under vacuum. The crude was purified by silica-gel column (2-3% MeOH in CHCl$_3$) to give 1 mg of 27 as viscous oil. HRMS (ESI) m/z Calcd for C$_{32}$H$_{52}$N$_3$O$_6$ (M+1)$^+$ 574.3856. found 544.3858.

30. (S,Z)-5-((1R,4R)-4-((2E,4E)-5-((2S,4R)-4-(chloromethyl)-4-hydroxy-6,6-dimethyltetrahydro-2H-pyran-2-yl)-3-methylpenta-2,4-dienyl)cyclohexy-lamino)-5-oxopent-3-en-2-yl 4-cycloheptylpiperazine-1-carboxylate (28)

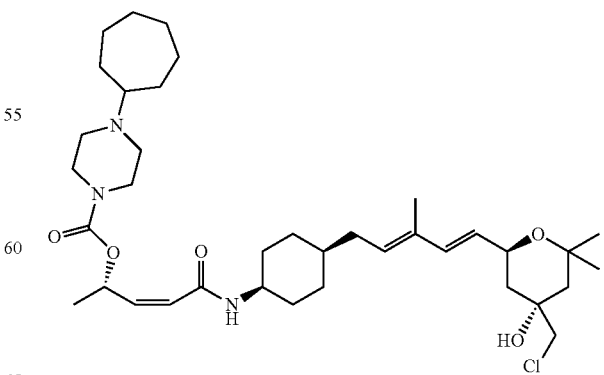

Yield: 1.5 mg (47%) as viscous oil. $^1$H NMR (400 MHz, CDCl$_3$) δ 8.23-8.13 (m, 1H), 7.17-7.07 (m, 1H), 6.87-6.76

(m, 1H), 6.29 (d, J=15.7 Hz, 1H), 5.83 (d, J=11.1 Hz, 1H), 5.66-5.46 (m, 4H), 4.54-4.42 (m, 1H), 4.20-4.05 (m, 2H), 3.46 (d, J=1.8 Hz, 6H), 2.62-2.53 (m, 1H), 2.49 (s, 4H), 2.08 (s, 3H), 1.78 (s, 2H), 1.70 (d, J=14.6 Hz, 8H), 1.56 (s, 18H), 1.45 (s, 8H), 1.36 (t, J=9.7 Hz, 7H), 1.26 (s, 6H); MS (ESI) m/z 662 (M)⁺.

31. Synthesis of Analog 38

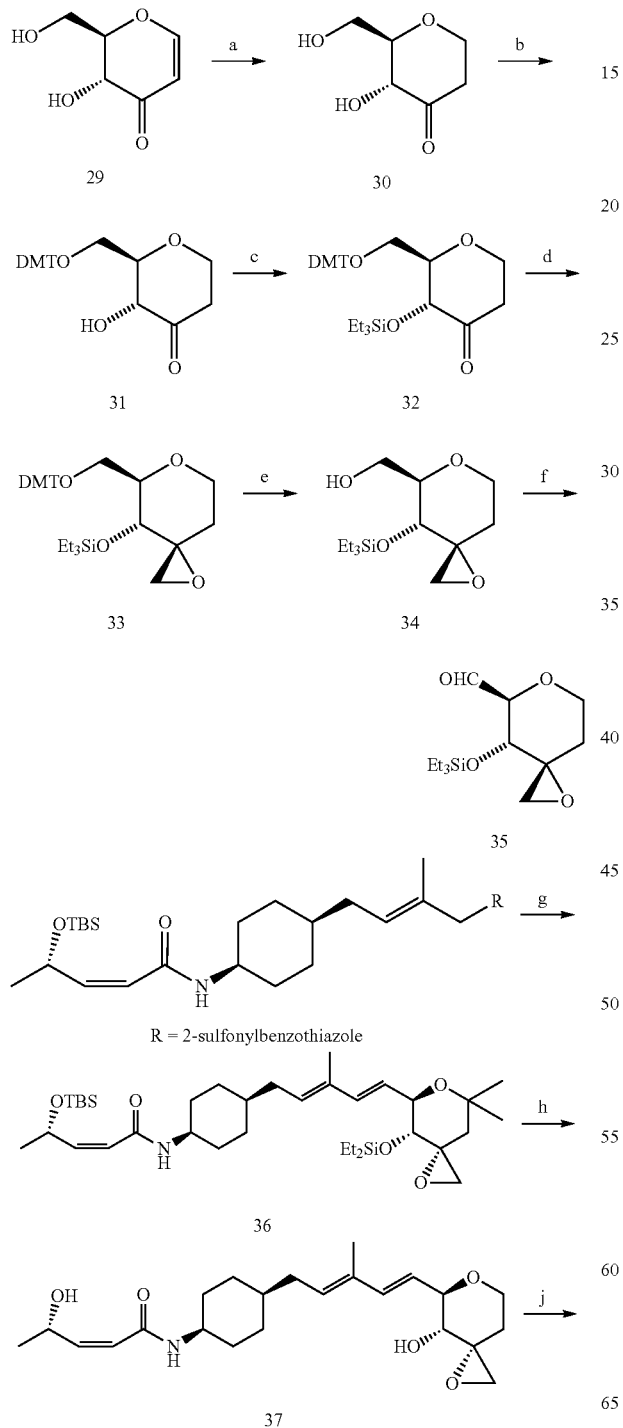

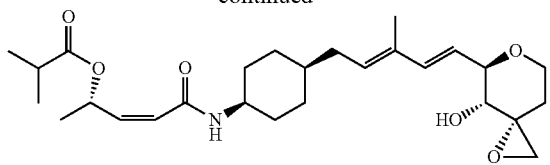

38

Reagents and conditions: (a) Pd/C, H₂, MeOH; (b) DMTCl; pyridine; c) Et₃SiCl, Et₃N; (d) Me₃SI, n-BuLi, -78° C. -0° C., THF; e) 10% Pd/C, H₂, MeOH; (f) TPAP, NMO, 4Å MS, CH₂Cl₂; (g) LHMDS, aldehyde, THF, -78° C. to rt; (h) Bu₄NF, THF 0° C.; I) isobutyric anhydride, Et₃N, DMAP, CH₂Cl₂.

32. (2R,3R)-3-hydroxy-2-(hydroxymethyl)dihydro-2H-pyran-4(3H)-one (30)

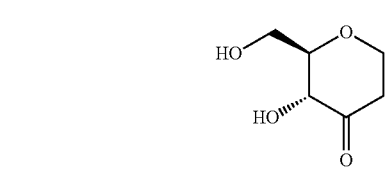

The olefin 29 (2.03 g, 14.08 mmol) and Pd/C (100 mg) were dissolved in EtOAc (200 mL) and placed first under nitrogen and then hydrogen. The reaction mixture was stirred for 18 hrs. A TLC was taken in 100% EtOAc and stained with anisaldehyde. The reaction mixture was filtered through celite. The celite was washed several times with EtOAc and the filtrate was concentrated yielding colorless oil. The crude product was chromatographed by using a gradient from 90-100% EtOAc/Hex. ¹H NMR (400 MHz, MeOD) δ 4.27 (ddd, J=11.3, 7.5, 1.2 Hz, 1H), 4.15-4.10 (m, 1H), 3.87 (dd, J=12.0, 2.2 Hz, 1H), 3.78-3.72 (m, 1H), 3.68-3.59 (m, 1H), 3.35-3.32 (m, 1H), 2.79 (tdd, J=12.6, 7.5, 1.4 Hz, 1H), 2.40 (ddd, J=14.0, 2.4, 1.2 Hz, 1H).

33. (2R,3R)-2-((bis(4-methoxyphenyl)(phenyl)methoxy)methyl)-3-hydroxydihydro-2H-pyran-4(3H)-one 31

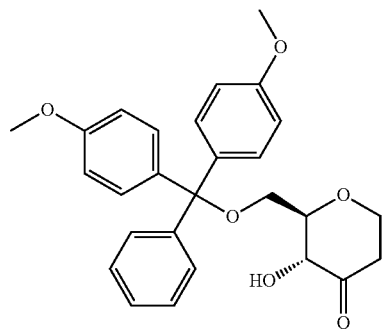 [SMILES: COc1ccc(C(OC[C@H]2OCCC(=O)[C@@H]2O)(c2ccccc2)c2ccc(OC)cc2)cc1]

Dissolve (2R,3R)-3-hydroxy-2-(hydroxymethyl)dihydro-2H-pyran-4(3H)-one (662 mg, 4.53 mmol) and DMTCl (1.688 g, 4.98 mmol) in pyridine (5 mL). The reaction was stirred overnight and a TLC was taken in 30% EtOAc/Hexane. The crude reaction mixture was partitioned with 1M CuSO₄ (10 mL) and the aqueous layer extracted with DCM (3×30 mL). The combined organic fractions were washed once with water (20 mL) and dried over Na₂SO₄. The crude product was chromatographed using a gradient from 10%-30% EtOAc/Hexane to yield 1.51 g (74%). ¹H NMR (400 MHz, CDCl₃) δ 7.49 (dd, J=8.4, 1.2 Hz, 2H), 7.40-7.35 (m, 4H), 7.29 (t, J=4.3, 2H), 7.20 (t, J=7.3 Hz, 1H), 6.86-6.80 (m, 4H), 4.39 (ddd, J=11.3, 7.5, 1.0 Hz, 1H), 4.26 (ddd, J=9.5, 3.8, 1.4 Hz, 1H), 3.79 (s, 6H), 3.70-3.61 (m, 1H), 3.47 (dd, J=5.8, 2.8 Hz, 2H), 3.43-3.34 (m, 2H), 2.90-2.78 (m, 1H), 2.60-2.53 (m, 1H). ¹³C NMR (101 MHz, CDCl₃) δ 208.13, 158.91, 145.38, 136.50, 130.62, 129.60, 128.70, 128.25, 127.20, 113.56, 86.57, 84.09, 74.84, 67.87, 64.25, 55.67, 41.45; IR (neat film) 3458, 2938, 1720, 1509, 1250, 1178, 1110; LRMS for $C_{27}H_{28}O_6$ (M+Na) 471.02.

34. (2R,3R)-2-((bis(4-methoxyphenyl)(phenyl)methoxy)methyl)-3-(triethylsilyloxy)dihydro-2H-pyran-4(3H)-one 32

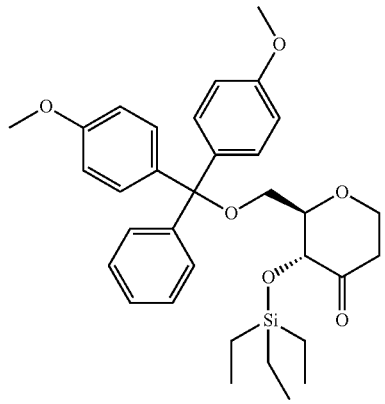 [SMILES: CC[Si](CC)(CC)O[C@H]1C(=O)CCO[C@@H]1COC(c1ccccc1)(c1ccc(OC)cc1)c1ccc(OC)cc1]

To a solution of (2R,3R)-2-((bis(4-methoxyphenyl)(phenyl)methoxy)methyl)-3-hydroxydihydro-2H-pyran-4(3H)-one (1.26 g, 2.81 mmol) and imidazole (383 mg, 5.62 mmol) in pyridine (8 mL), in an ice bath, was added drop-wise TESCl (710 μL, 4.21 mmol). The reaction was stirred in an ice bath for 20 min and at room temperature for 20 min after which the first TLC was taken in 30% EtOAc/Hex and showed that there was no starting material present. The reaction was partitioned with EtOAc and sat NaHCO₃ and the aqueous layer extracted with EtOAc. The combined organic fractions were dried over Na₂SO₄, concentrated and chromatographed using 15% EtOAc/Hex with 0.5% TEA to load the column and to obtain the product 31, 1.58 g (84%). ¹H NMR (400 MHz, CDCl₃) δ 7.42 (dd, J=8.4, 1.2 Hz, 2H), 7.30 (dd, J=8.9, 1.8 Hz, 4H), 7.21 (t, J=4.3 Hz, 2H), 7.16-7.10 (m, 1H), 6.78-6.72 (m, 4H), 4.31-4.24 (m, 1H), 4.06 (d, J=9.6 Hz, 1H), 3.72 (s, 6H), 3.62 (td, J=12.5, 2.4 Hz, 1H), 3.55 (ddd, J=9.6, 6.0, 1.8 Hz, 1H), 3.41 (dd, J=10.0, 1.8 Hz, 1H), 3.15 (dd, J=10.0, 6.0 Hz, 1H), 2.66 (ddd, J=13.8, 7.9, 6.8 Hz, 1H), 2.44-2.36 (m, 1H), 0.71 (t, J=7.9 Hz, 9H), 0.46-0.27 (m, 6H). ¹³C NMR (101 MHz, CDCl₃) δ 206.28, 158.91, 145.41, 136.60, 130.64, 128.76, 128.18, 127.15, 113.50, 86.46, 83.94, 76.33, 67.47, 64.74, 55.66, 42.64, 7.22, 5.35; IR (neat film) 2955, 1732, 1608, 1509, 1250, 1178, 1139, 1040, 831, 735; LRMS for $C_{33}H_{42}O_6Si$ (M+Na) 585.09.

35. ((3R,4R,5R)-5-(bis(4-methoxyphenyl)(phenyl)methoxy)methyl)-1,6-dioxaspiro[2.5]octan-4-yloxy)triethylsilane 33

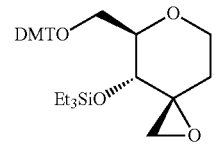

A suspension of trimethylsulfonium iodide (471 mg, 2.31 mmol) in THF (2 mL) was treated with n-BuLi (2.2 mL, 2.22 mmol, 1.6 M in THF) at −78° C. The suspension was stirred for 30 min, and then the suspension was allowed to warm to room temperature. The reaction was then cooled to −10-0° C. (salt ice bath) and ketone derivative 32 (250 mg, 0.44 mmol) in THF (1 mL) was added drop-wise. The suspension was allowed to stir at 0° C. for 1 h by which time analytical SFC (silica column, 5-20% MeOH) showed that all of starting material has been consumed. The reaction mixture was poured into an ice water (25 mL) and the product was then extracted with ethyl acetate (2×25 mL), washed with brine and dried over Na₂SO₄. The residue was purified by silica-gel chromatography (15% ethyl acetate in hexane) to give 130 mg (51%) of 33 as white semi solid. ¹H NMR (400 MHz, CDCl₃) δ ¹H NMR (400 MHz, CDCl₃) δ 7.53-7.46 (m, 2H), 7.40-7.34 (m, 4H), 7.31-7.25 (m, 2H), 7.19 (t, J=7.3 Hz, 1H), 6.82 (d, J=8.9 Hz, 4H), 4.15 (dd, J=11.4, 3.8 Hz, 1H), 3.78 (s, 6H), 3.61 (dd, J=18.3, 5.8 Hz, 2H), 3.50-3.41 (m, 1H), 3.37 (dd, J=9.8, 1.7 Hz, 1H), 3.14 (dd, J=9.8, 6.9 Hz, 1H), 2.96 (d, J=5.6, 1H), 2.50 (d, J=5.6 Hz, 1H), 2.29-2.13 (m, 1H), 1.41 (d, J=13.2 Hz, 1H), 0.75 (dd, J=9.6, 6.3 Hz, 9H), 0.46-0.20 (m, 6H); ¹³C NMR (101 MHz, CDCl₃) δ 158.41, 145.15, 136.40, 136.32, 130.22, 128.35, 127.70, 126.60, 113.01, 85.86, 82.08, 68.43, 66.36, 64.44, 60.30, 55.20, 48.81, 33.88, 6.78, 4.60; HRMS (ESI) m/z Calcd for $C_{40}H_{39}O_5$ (M+1)⁺ 599.2797. found 599.2795.

36. ((3R,4R,5R)-4-(triethylsilyloxy)-1,6-dioxaspiro[2.5]octan-5-yl)methanol 34

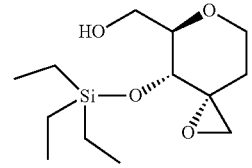 [SMILES: CC[Si](CC)(CC)O[C@@H]1[C@@H](CO)OCC[C@@]12CO2]

A solution of diprotected epoxide 33 (90 mg, 0.15 mmol) in MeOH (2.1 mL) at room temperature as 10% Pd/C (16 mg) was added and stirred under H₂ atm (balloon) for over night. Diluted with ethyl acetate (10 mL) and the solids were filtered through celite. The solvent was concentrated and purified by silica column (20% ethyl acetate in hexane) to give 35 mg (82%) of 34 as a liquid. ¹H NMR (400 MHz, CDCl₃) δ 4.06 (dd, J=11.4, 5.2, 1H), 3.88-3.82 (m, 1H), 3.77 (d, J=9.3 Hz, 1H), 3.74-3.64 (m, 1H), 3.62-3.54 (m, 1H), 3.29-3.24 (m, 1H), 3.00 (d, J=5.6 Hz, 1H), 2.52 (d, J=5.6 Hz, 1H), 2.27-2.16 (m, 1H), 1.96 (t, J=6.3 Hz, 1H), 1.40 (d, J=13.4 Hz, 1H), 0.98-0.91 (m, 9H), 0.66-0.60 (m, 6H); ¹³C NMR (101 MHz, CDCl$_3$) δ 75.13, 74.82, 74.50, 65.70, 64.28, 60.44, 57.89, 46.36, 31.58, 4.61, 2.55; MS (API) m/z 275.5 (M+1)$^+$.

37. (3R,4R,5S)-4-(triethylsilyloxy)-1,6-dioxaspiro[2.5]octane-5-carbaldehyde 35

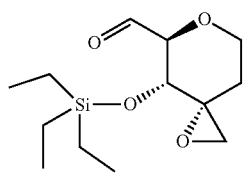 [SMILES: CC[Si](CC)(CC)O[C@@H]1[C@@H](C=O)OCC[C@@]12CO2]

A stirred suspension of alcohol 34 (15 mg, 0.05 mmol) and 4A° MS (15 mg) in CH$_2$Cl$_2$ (1 mL) at 0° C. was treated sequentially with N-methylmorpholine-N-oxide (9.6 mg, 0.08 mmol) and tetrapropylammonium perruthenate (1.9 mg, 5.47 μmol). After 10 min at 0° C., the resulting suspension was allowed to warm to room temperature and stirred for 30 min by which time TLC showed that all of starting material has been consumed. The suspension was directly loaded onto silica column and eluted with 40% ethyl acetate in hexane to give 7 mg (47%) of 35 as liquid. $^1$H NMR (400 MHz, CDCl$_3$) δ 9.76 (d, J=0.9 Hz, 1H), 4.16 (ddd, J=11.5, 5.0, 2.7 Hz, 1H), 3.95-3.76 (m, 2H), 3.65 (td, J=11.5, 2.6 Hz, 1H), 3.05 (dd, J=5.3, 1.4 Hz, 1H), 2.59 (d, J=5.4 Hz, 1H), 2.21-2.07 (m, 1H), 1.59 (t, J=2.6 Hz, 1H), 0.98-0.89 (m, 10H), 0.66-0.55 (m, 6H).

38. (S,Z)-4-(tert-butyldimethylsilyloxy)-N-((1S,4R)-4-((2E,4E)-3-methyl-5-((3R,4R,5R)-4-(triethylsilyloxy)-1,6-dioxaspiro[2.5]octan-5-yl)penta-2,4-dienyl)cyclohexyl)pent-2-enamide (36)

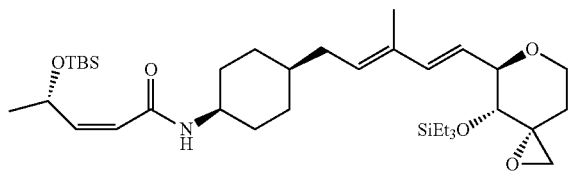

A solution of sulfone derivative (from Example 9, 15.2 mg, 0.02 mmol) in dry THF (0.5 mL) was stirred and cooled at −78° C. as Lithium bis(trimethylsilyl) amide (48 uL, 0.04 mmol, 1.0 M in THF) was added dropwise. The solution was turned into orange color. After stirring for 10 min at −78° C., the aldehyde (6 mg, 0.02 mmol) in dry THF (0.5 mL) was introduced drop-wise. The resulting suspension was stirred at −78° C. for 1.5 h and allowed to warm to room temperature and stirred for 4 h. LC/MS and TLC were showed that all of starting material has been consumed. The reaction was poured into a saturated aqueous NH$_4$Cl solution (5 mL) and the product was extracted with CH$_2$Cl$_2$ (2×15 mL). The combined extracts were washed with saturated aqueous NaHCO$_3$ (5 mL) and brine (5 mL), and dried over Na$_2$SO$_4$. The solvent was evaporated and the crude residue was purified by column chromatography (20% ethyl acetate in hexane) to give 6 mg (43%) of 36 as a viscous liquid. $^1$H NMR (400 MHz, CDCl$_3$) δ 6.33 (d, J=15.7 Hz, 1H), 6.03-5.95 (m, 1H), 5.58 (d, J=1.2 Hz, 5H), 4.15-4.00 (m, 2H), 3.71-3.55 (m, 3H), 3.05 (dd, J=5.6, 1.3 Hz, 1H), 2.53 (d, J=5.7 Hz, 1H), 2.25 (td, J=12.9, 5.3 Hz, 1H), 2.10 (t, J=7.9 Hz, 2H), 1.74 (s, 3H), 1.43-1.42 (m, 3H), 1.32-1.21 (m, 16H), 0.96-0.81 (m, 12H), 0.60-0.55 (m, 6H), 005 (d, J=5.6 Hz, 6H); $^{13}$C NMR (101 MHz, CDCl$_3$) δ 164.82, 150.04, 136.17, 133.93, 131.78, 127.11, 119.94, 73.06, 69.59, 65.48, 55.68, 51.05, 45.39, 42.46, 38.64, 36.34, 34.03 31.55, 29.45, 29.33, 27.95, 27.89, 25.91, 23.82, 23.78, 18.22, 12.54, −4.67, −4.69.

39. (S,Z)-4-hydroxy-N-((1S,4R)-4-((2E,4E)-5-((3R,4R,5R)-4-hydroxy-1,6-dioxaspiro[2.5]octan-5-yl)-3-methylpenta-2,4-dienyl)cyclohexyl)pent-2-enamide 37

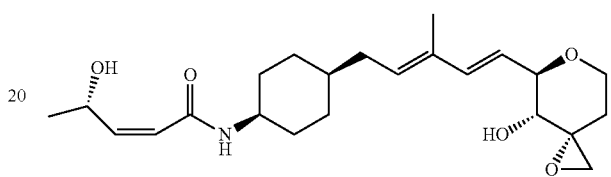

A solution of TBS protected diene 36 (6 mg, 0.09 mmol) in THF (0.4 mL) was stirred and cooled at 0° C. as TBAF (47 μL, 0.047 mmol, 1.0 M in THF) was added. The resulting yellow solution was allowed to stir for 2.5 h at 0° C. by which time the TLC showed that all of starting material has been consumed. Evaporation of THF and purification of the residue by flash chromatography (70-80% ethyl acetate in hexane) gave 2.0 mg (51%) of 37 as a liquid. $^1$H NMR (400 MHz, CDCl$_3$) δ 6.42 (d, J=15.7 Hz, 1H), 6.16 (dd, J=11.9, 5.4 Hz, 1H), 5.83 (d, J=6.9 Hz, 1H), 5.74 (d, J=12.1, 1H), 5.63 (dd, J=15.7, 6.9 Hz, 1H), 5.58-5.46 (m, 2H), 4.76 (dd, J=11.6, 5.5 Hz, 1H), 4.18-4.00 (m, 2H), 3.70 (dd, J=31.2, 8.5 Hz, 16H), 3.20 (d, J=4.8 Hz, 1H), 2.67 (d, J=5.0 Hz, 1H), 2.30 (td, J=12.7, 4.4, 1H), 2.28 (ddd, J=22.2, 15.3, 6.1 Hz, 1H), 2.10 (t, J=7.2 Hz, 10H), 1.76 (s, 3H); MS (ESI) m/z 406 (M+1)$^+$.

40. (S,Z)-5-((1S,4R)-4-((2E,4E)-5-((3R,4R,5R)-4-hydroxy-1,6-dioxaspiro[2.5]octan-5-yl)-3-methyl-penta-2,4-dienyl)cyclohexylamino)-5-oxopent-3-en-2-yl isobutyrate (38)

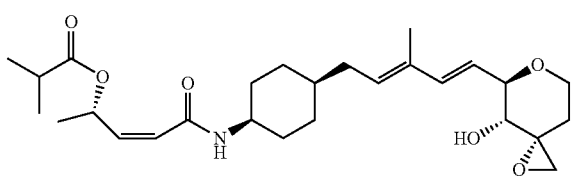 [SMILES: CC(/C=C/[C@H]1OCC[C@@]2(CO2)[C@@H]1O)=C\C[C@H]1CC[C@@H](NC(=O)/C=C\[C@H](C)OC(=O)C(C)C)CC1]

A solution of alcohol 37 (1.45 mg, 3.45 μmol) in anhyd CH$_2$Cl$_2$ (0.2 mL) at 0° C. as Et$_3$N (3.44 μL, 0.017 mmol) and DMAP (5 μL, 0.2 M) were added. After 5 min, isobutyric anhydride (7.6 μL) was added. The solution was allowed to stir for 2 h at the same temp by which time the TLC showed that all of sm has been consumed. The solvent was evaporated and the crude residue was purified by Pre-SFC (ADH column, 20% MeOH) to give 0.28 mg of 38 as viscous oil; MS (ESI) m/z 476 (M+1)$^+$.

41. Synthesis of Analog 48

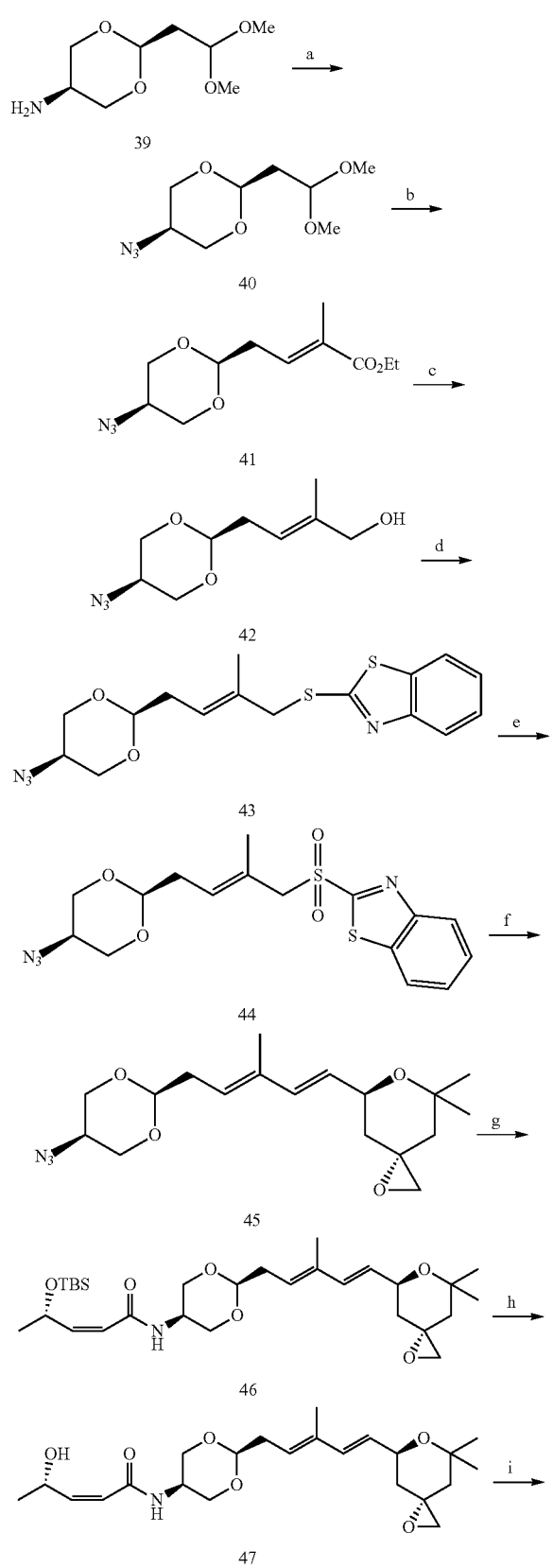

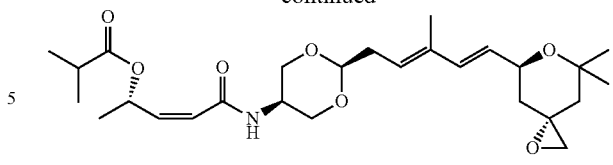

48

Reagents and conditions: (a) 1H-imidazole-1-sulfonyl azide-HCl, K₂CO₃, MeOH, 0° C.-rt (b) i) 20% TFA, CHCl₃, 0° C. ii) Ph₃PC(CH₃)CO₂Et, benzene; (c) DIBALH, -78° C., CH₂Cl₂; (d) 2-mercapto benzothiazole, DIAD, THF; (e) ammonium molybdate 4H₂O, H₂O₂, EtOH, buffer pH7; (f) LiHMDS, aldehyde, THF, -78° C. to rt; (g) i) Ph₃P, benzene, H₂O, 45° C.; ii) (S,Z)-4-(TBSO)pent-2-enoic acid, HBTU, Hunig's base, CH₃CN; (h) Bu₄NF, THF, 0° C.; i) isobutyric anhydride, Et₃N, DMAP, CH₂Cl₂.

42. (2S,5S)-5-azido-2-(2,2-dimethoxyethyl)-1,3-dioxane 40

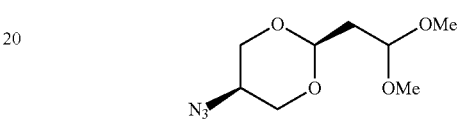

Crude 2-(2,2-dimethoxyethyl)-1,3-dioxan-5-amine 39 (59.8 g, 313 mmol) was dissolved in MeOH (1.5 L) and cooled to 0° C. K₂CO₃ (86 g, 625 mmol) and CuSO₄.5H₂O (780 mg, 3.13 mmol) were added to the reaction flask at 0° C. followed by 1H-imidazole-1-sulfonyl azide-HCl (65.3 g, 375 mmol). The reaction was warmed to room temperature and stirred overnight. A TLC was taken in 10% MeOH/CHCl₃ and stained with CAM. The reaction mixture was concentrated and diluted with water. The resulting mixture was extracted with EtOAc (3×10 mL). The combined organic fractions were dried over Na₂SO₄ and concentrated. The crude product was chromatographed using 30% EtOAc/Hex with 0.5% TEA to obtain the product 40, a colorless oil, 33.65 g (50%). ¹H NMR (400 MHz, CDCl₃) δ 4.72 (t, J=5.5 Hz, 1H), 4.56 (t, J=5.9 Hz, 1H), 4.21 (dd, J=1.4, 12.5 Hz, 2H), 4.05-3.98 (m, 2H), 3.33 (d, J=3.7 Hz, 6H), 3.01 (s, 1H), 1.99 (t, J=5.7 Hz, 2H). ¹³C NMR (101 MHz, CDCl₃) δ 100.90, 99.96, 69.59, 53.38, 53.13, 38.19; IR (neat film) 2950, 2107, 1409, 1123; LRMS for C₈H₁₅N₃O₄ (M+Na) 239.79.

43. (E)-ethyl 4-((2S,5S)-5-azido-1,3-dioxan-2-yl)-2-methylbut-2-enoate (41)

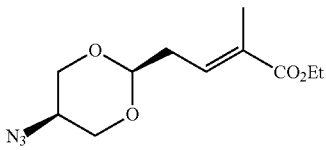 [SMILES: CCOC(=O)/C(C)=C/C[C@H]1OC[C@@H](N=[N+]=[N-])CO1]

5-azido-2-(2,2-dimethoxyethyl)-1,3-dioxane 40 (33.65 g, 155 mmol) was dissolved in CHCl₃ (1 L) with water (6.25 mL, 347 mmol) and cooled to 0° C. TFA (250 mL, 3.366 mol) was added to the reaction mixture to give 20% TFA/CHCl₃ which was stirred at 0° C. for 40 min. The reaction was quenched with solid NaHCO₃ (400 g, 4.76 mol) at 0° C. The reaction mixture was filtered and concentrated. The resulting aldehyde was used in the next step without further purification.

The impure aldehyde (26.59 g, 155 mmol) was dissolved in benzene (333 mL) and cooled in an ice bath to 0° C. (Carbethoxyethyldiene)triphenylphosphorane (51.15 g, 141 mmol) was added to the reaction mixture at 0° C. which was warmed to room temperature and stirred for 2 hrs. A TLC was taken in 20% EtOAc/Hex. The reaction mixture was concentrated and the crude product was chromatographed using 20% EtOAc/Hex with 0.5% TEA to give 41, 28.61 g (72%). $^1$H NMR (400 MHz, CDCl$_3$) δ 6.78 (td, J=7.2, 1.5 Hz, 1H), 4.74 (t, J=5.1 Hz, 1H), 4.24 (dd, J=12.5, 1.4 Hz, 2H), 4.18 (q, J=7.1 Hz, 2H), 4.07-3.99 (m, 2H), 2.99 (s, 1H), 2.56 (ddd, J=7.1, 5.2, 1.0 Hz, 2H), 1.84 (d, J=1.2 Hz, 3H), 1.27 (t, J=7.4 Hz, 3H). $^{13}$C NMR (101 MHz, CDCl$_3$) δ 167.80, 134.53, 130.54, 101.12, 69.76, 60.58, 53.12, 34.44, 14.28, 12.71; IR (neat film) 2981, 2860, 2105, 1707, 1654, 1451, 1254, 885; LRMS for C$_{11}$H$_{17}$N$_3$O$_4$ (M+Na) 277.84.

44. (E)-4-((2S,5S)-5-azido-1,3-dioxan-2-yl)-2-methylbut-2-en-1-ol (42)

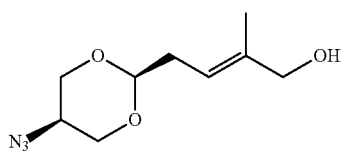

The ester 41 (28.61 g, 112 mmol) was dissolved in DCM (500 mL) and cooled to −78° C. in an acetone/dry ice bath. DIBALH (280 mL, 1M in hexanes, 280 mmol) was added drop-wise and the reaction was allowed to stir for 1 hr. A TLC was taken in 40% EtOAc/Hex. The top spot is 5-azido-2-(2,2-dimethoxyethyl)-1,3-dioxane which stains yellow with anisaldehyde. The lower spot is the product which stains black. The reaction was quenched with MeOH (200 mL) at −78° C. after which saturated aqueous potassium sodium tartrate tetrahydrate (200 mL) was added. The reaction mixture was filtered and extracted with DCM. The combined organic fractions were dried over MgSO$_4$ and concentrated. The crude product was chromatographed using 30% EtOAc/Hex. ~4 g of 5-azido-2-(2,2-dimethoxyethyl)-1,3-dioxane was recovered along with product, 42 17.32 g, (73%). $^1$H NMR (400 MHz, CDCl$_3$) δ 5.50 (s, 1H), 4.67 (t, J=4.9 Hz, 1H), 4.24 (d, J=11.1 Hz, 3H), 4.05-3.99 (m, 5H), 2.96 (s, 1H), 2.49-2.41 (m, 3H), 1.67 (s, 4H), 1.46 (s, 1H). $^{13}$C NMR (101 MHz, CDCl$_3$) δ 137.97, 118.29, 102.03, 69.82, 68.56, 53.20, 33.36, 13.94; IR (neat film) 3397, 2917, 2861, 2107, 1393, 1289, 1243, 1142, 1043, 1007; LRMS for C$_9$H$_{15}$N$_3$O$_3$ (M+Na) 235.76.

45. 2-((E)-4-((2S,5S)-5-azido-1,3-dioxan-2-yl)-2-methylbut-2-enylthio)benzo[d]thiazole (43)

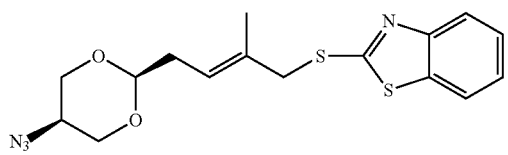 [SMILES: C/C(=C\C[C@H]1OC[C@@H](N=[N+]=[N-])CO1)CSc1nc2ccccc2s1]

A solution of 2-mecapto benzothiazole (16.1 g, 97 mmol) and Ph$_3$P (24.3 g, 93 mmol) in anhyd THF (350 mL) was stirred and cooled at 0° C. as DIAD (20.2 mL, 97 mmol) in toluene (40 mL) was added slowly for 30 min. The resulting yellow suspension was allowed to stir for 15 min as alcohol 42 (17.2 g, 81 mmol) in anhyd THF (80 mL) was added drop-wise over 20 min. The resulting yellow suspension was allowed to stir for 30 min at 0° C. by which time the TLC was indicated that all of starting material has been consumed. Diluted with hexane (200 mL) and ethyl acetate (200 mL), the resulting solids were filtered and washed with ethyl acetate (100 mL). Concentration of the solvent then diluted with ethyl acetate (400 mL) and washed with saturated aqueous NaHCO$_3$ (100 mL) and water (100 mL), dried over Na$_2$SO$_4$. Concentration and purification of the crude by column chromatography (30% ethyl acetate in hexane) gave 25 g (84%) of 43 viscous oil. $^1$H NMR (400 MHz, CDCl$_3$) δ 7.87 (d, J=8.2 Hz, 1H), 7.75 (dd, J=8.0, 0.6 Hz, 1H), 7.45-7.37 (m, 1H), 7.33-7.27 (m, 1H), 5.62 (t, J=7.1 Hz, 1H), 4.56 (t, J=5.1 Hz, 1H), 4.18 (d, J=11.6 Hz, 2H), 4.00 (s, 2H), 3.93 (dd, J=12.4 Hz, 2H), 2.95 (s, 1H), 2.48-2.37 (m, 2H), 1.80 (s, 3H). $^{13}$C NMR (101 MHz, CDCl$_3$) δ 166.84, 153.22, 135.42, 132.62, 126.00, 124.22, 123.40, 121.62, 120.92, 101.87, 69.64, 53.25, 42.96, 33.97, 15.60; IR (Neat Film) 2975, 2917, 2856, 2104, 1457, 1426, 1291, 1239, 1140, 1044, 1004 cm$^{-1}$; HRMS (ESI) m/z Calcd for C$_{16}$H$_{19}$N$_4$O$_2$S$_2$ (M+1)$^+$ 363.0949. found 363.0942.

46. 2-((E)-4-((2S,5S)-5-azido-1,3-dioxan-2-yl)-2-methylbut-2-enylsulfonyl)benzo[d]thiazole 44

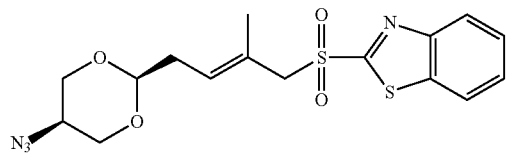 [SMILES: C/C(=C\C[C@H]1OC[C@@H](N=[N+]=[N-])CO1)CS(=O)(=O)c1nc2ccccc2s1]

To a solution of sulfide derivative 43 (0.3 g, 0.82 mmol) in EtOH (6 mL) were added a mixture of ammonium molybdate.4H$_2$O (0.2 g, 0.16 mmol) and 30% H$_2$O$_2$ (1 mL, 8.28 mmol) adjusted pH to 4-5 with buffer 7.0. The resulting solution was stirred for 4 h at room temperature. Diluted with water (15 mL) and CHCl$_3$, brine (25 mL), and dried over Na$_2$SO$_4$. The solvent was removed under reduced pressure to give crude as liquid. The crude residue was purified by silica column (40% ethyl acetate in hexane, 200 mL and 65% ethyl acetate in hexane 100 mL) to give 44 (254 mg, 78%) as viscous oil. $^1$H NMR (400 MHz, CDCl$_3$) δ 8.29-8.21 (m, 1H), 8.05-7.98 (m, 1H), 7.68-7.55 (m, 2H), 5.37 (t, J=7.1 Hz, 1H), 4.30 (t, J=5.3 Hz, 1H), 4.17 (s, 2H), 4.03-3.95 (m, 2H), 3.77-3.68 (m, 2H), 2.84 (s, 1H), 2.36-2.28 (m, 2H), 1.86 (s, 3H); $^{13}$C NMR (101 MHz, CDCl$_3$) δ 165.57, 152.78, 137.02, 130.65, 127.90, 127.57, 125.60, 125.03, 122.29, 101.14, 69.48, 64.41, 53.01, 34.05, 17.12; IR (Neat Film) 2974, 2922, 2857, 2105, 1471, 1422, 1327, 1291, 1239, 1136, 1021 cm$^{-1}$; HRMS (ESI) m/z Calcd for C$_{16}$H$_{19}$N$_4$O$_4$S$_2$ (M+1)$^+$ 395.0848. found 395.0848.

47. (3R,7S)-7-((1E,3E)-5-((2S,5R)-5-azido-1,3-dioxan-2-yl)-3-methylpenta-1,3-dienyl)-5,5-dimethyl-1,6-dioxaspiro[2.5]octane 45

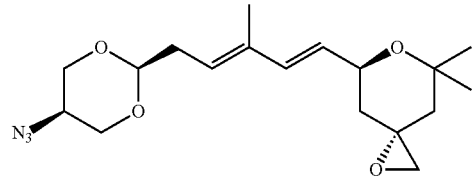 [SMILES: CC(/C=C/[C@@H]1C[C@]2(CO2)CC(C)(C)O1)=C\C[C@H]1OC[C@@H](N=[N+]=[N-])CO1]

A solution of sulfone derivative 44 (280 mg, 0.71 mmol) in dry THF (8 mL) was stirred and cooled at −78° C. as Lithium bis(trimethylsilyl) amide (0.87 mL, 0.64 mmol, 1.0 M in THF) was added dropwise. The solution was turned into orange color. After stirring for 30 min at −78° C., the aldehyde (130 mg, 0.55 mmol) in dry THF (5 mL) was introduced drop-wise. The resulting suspension was stirred at −78° C. for 1.5 h and allowed to warm to room temperature and stirred for 12 h. The reaction was poured into a saturated aqueous NH₄Cl solution (10 mL) and the product was extracted with ethyl acetate (3×25 mL). The combined extracts were washed with saturated aqueous NaHCO₃ (20 mL) and brine (20 mL), and dried over Na₂SO₄. Evaporation of the solvent and purification by silica-gel chromatography (20% ethyl acetate in hexane) gave 70 mg of diene 45 as a viscous liquid. ¹H NMR (400 MHz, CDCl₃) δ 6.27 (d, J=15.8 Hz, 1H), 5.60 (dd, J=15.7, 6.6 Hz, 1H), 5.51 (t, J=7.3 Hz, 1H), 4.62 (t, J=5.2 Hz, 1H), 4.46 (ddd, J=11.1, 6.7, 1.8 Hz, 1H), 4.27-4.19 (m, 2H), 4.00 (dd, J=12.4, 2.1 Hz, 2H), 2.98 (s, 1H), 2.59-2.55 (m, 2H), 2.54-2.49 (m, 2H), 2.04-1.85 (m, 2H), 1.74 (s, 3H), 1.40 (s, 3H), 1.28 (s, 3H), 1.25-1.11 (m, 2H); ¹³C NMR (101 MHz, CDCl₃) δ 135.75, 135.68, 127.95, 125.51, 102.09, 73.03, 69.72, 69.49, 55.68, 53.30, 51.06, 42.46, 38.57, 34.08, 31.54, 23.77, 12.61; IR (Neat Film) 2974, 2915, 2861, 2105, 1447, 1328, 1289, 1141, 1045 cm⁻¹; HRMS (ESI) m/z Calcd for $C_{16}H_{28}N_3O_4$ (M+1)⁺ 350.2080. found 350.2067.

48. (S,Z)-4-(tert-butyldimethylsilyloxy)-N-((2R,5R)-2-((2E,4E)-5-((3R,5S)-7,7-dimethyl-1,6-dioxaspiro [2.5]octan-5-yl)-3-methylpenta-2,4-dienyl)-1,3-dioxan-5-yl)pent-2-enamide 46

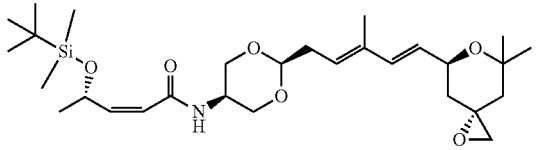 [SMILES: CC(/C=C/[C@@H]1C[C@]2(CO2)CC(C)(C)O1)=C\C[C@H]1OC[C@@H](NC(=O)/C=C\[C@H](C)O[Si](C)(C)C(C)(C)C)CO1]

A solution of azide derivative 45 (2 g, 5.72 mmol) in benzene (40 mL) at rt as Ph₃P (4.50 g, 17.17 mmol) was added and degassed used by vacuum and N₂. The resulting solution was heated at 45° C. for 2.5 h by which time LC/MS showed that the starting material has been consumed. Water (1 mL) was added and the reaction solution was heated at 45° C. for 2 h by which time LC/MS indicated that the formation of free amine and phosphoiminium complex has been disappeared. The reaction mixture was cooled to room temperature and then diluted with CH₂Cl₂ (100 mL) and ether (20 mL) and then dried over Na₂SO₄, filtered and concentrated. The residue was dissolved in anhyd acetonitrile (6 mL) and used in the next step without further purification. MS (ESI) m/z 324 (M+1)⁺ A stirred solution of conjugated acid (2.6 g, 11.44 mmol) in dry CH₃CN (30 mL) at 0° C. was treated with HBTU (4.1 g, 10.87) and diisopropyl ethylamine (6.12 mL, 34.3 mmol) sequentially. The above reaction solution was added to a solution containing (3R,7S)-7-((1E,3E)-5-((2S,5R)-5-azido-1,3-dioxan-2-yl)-3-methylpenta-1,3-dienyl)-5,5-dimethyl-1,6-dioxaspiro[2.5]octanein in CH₃CN (30 mL) at 0° C. The resulting solution was the stirred for another 2 h at room temperature at which time LC/MC showed the formation of product and disappearance of all of the starting material. Saturated aqueous NaHCO₃ (70 mL) and ethyl acetate (400 mL) were added. Organic layer was separated and the aqueous layer was extracted with ethyl acetate (2×100 mL) and washed with brine (100 mL). Evaporation and purification of the crude by silica column (25% ethyl acetate in hexane) gave 2.1 g (69%) of 46 as liquid. ¹H NMR (400 MHz, CDCl₃) δ 6.41 (d, J=8.8 Hz, 1H), 6.28 (d, J=15.7 Hz, 12H), 6.06 (dd, J=11.6, 7.8 Hz, 1H), 5.64-5.52 (m, 2H), 5.48 (t, J=7.1 Hz, 1H), 4.59 (t, J=5.2 Hz, 1H), 4.51-4.42 (m, 1H), 3.98-3.92 (m, 5H), 2.59-2.55 (m, 2H), 2.50-2.46 (m, 2H), 2.04-1.86 (m, 2H), 1.75 (s, 3H), 1.40 (s, 3H), 1.29-1.24 (m, 6H), 1.23-1.14 (m, 2H), 0.88 (s, 9H), 0.05 (s, 3H), 0.04 (s, 3H); ¹³C NMR (101 MHz, CDCl₃) δ 164.98, 151.41, 135.75, 135.55, 128.11, 125.41, 119.06, 102.29, 73.07, 70.44, 70.32, 69.46, 65.43, 55.66, 51.06, 43.52, 42.46, 38.59, 34.17, 31.54, 25.90, 23.78, 18.20, 12.65, −4.68, −4.74; IR (Neat Film) 3332, 2955, 2930, 2857, 1758, 1715, 1665, 1526, 1471, 1373, 1254, 1117, 1077, 1003 cm⁻¹; HRMS (ESI) m/z Calcd for $C_{29}H_{50}NO_6Si$ (M+1)⁺ 536.3407. found 536.3397.

49. (S,Z)—N-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-yl)-4-hydroxypent-2-enamide 47

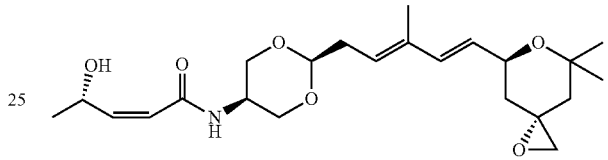

A solution of TBS protected amide 46 (2.1 g, 3.92 mmol) in 20 mL of THF at −10° C. as TBAF (5.4 mL, 5.49 mmol, 1.0 M in THF) was added. The light yellow solution was allowed to stir for 1.5 h at 0° C. and allowed to stir at room temperature for 2 h by which time TLC and LC/MS showed the starting material has been consumed. THF was evaporated and diluted with CHCl₃ (100 mL) and water (20 mL) and saturated aqueous NaHCO₃ (30 mL). The CHCl₃ layer was separated and the aq layer was extracted with CHCl₃ (2×75 mL). The combined extracts were washed with brine (50 mL) and dried over Na₂SO₄. Concentrated and the residue was purified by Prep-SFC(OD-H column, 10% MeOH) to give 780 mg (47%) of 47 as liquid. ¹H NMR (400 MHz, CDCl₃) δ 6.67 (d, J=7.9 Hz, 1H), 6.28 (d, J=15.7 Hz, 1H), 6.21 (dd, J=11.9, 5.6 Hz, 1H), 5.82 (dd, J=12.0, 1.6 Hz, 1H), 5.61 (dd, J=15.7, 6.6 Hz, 1H), 5.47 (t, J=7.2 Hz, 1H), 5.25 (s, 1H), 4.80 (s, 1H), 4.60 (t, J=5.2 Hz, 1H), 4.46 (ddd, J=10.9, 6.6, 1.8 Hz, 1H), 4.02-3.90 (m, 5H), 2.57 (s, 2H), 2.53-2.44 (m, 2H), 2.02-1.85 (m, 2H), 1.74 (s, 3H), 1.67 (s, 1H), 1.40 (s, 3H), 1.35 (d, J=6.7 Hz, 3H), 1.27 (s, 3H), 1.23-1.13 (m, 2H); ¹³C NMR (101 MHz, CDCl₃) δ 165.89, 150.80, 135.82, 135.52, 128.17, 125.28, 122.49, 102.34, 73.08, 70.13, 69.46, 64.48, 55.66, 51.06, 43.87, 42.44, 38.58, 34.11, 31.53, 23.77, 22.67, 12.66; IR (Neat Film) 3322, 2973, 2912, 2856, 1656, 1627, 1526, 1451, 1377, 1254, 1117, 1077, 1003 cm⁻¹; MS (ESI) m/z 422.5 (M+1)⁺; HRMS (ESI) m/z Calcd for $C_{23}H_{36}NO_6$ (M+1)⁺ 422.2543. found 422.2534.

50. (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl isobutyrate 48

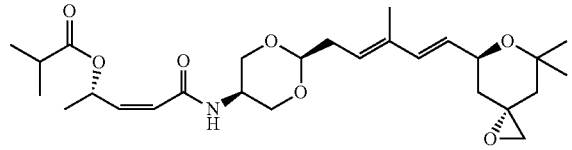 [SMILES: CC(/C=C/[C@@H]1C[C@]2(CO2)CC(C)(C)O1)=C\C[C@H]1OC[C@@H](NC(=O)/C=C\[C@H](C)OC(=O)C(C)C)CO1]

A solution of alcohol 47 (690 mg, 1.63 mmol) in DCM (14 mL) at 0° C. as Et₃N (8.18 mmol, 1.1 mL) and DMAP (30 mg, 0.246 mmol) were sequentially added. After 5 min, isobutyric anhydride (0.9 mL, 5.40 mmol) was added. The solution was allowed to stir for 1 h at the same temp by which time TLC indicated that starting material has completely been consumed. The reaction mixture was diluted with water (10 mL) and CH₂Cl₂ (30 mL). The aqueous layer was extracted with CH₂Cl₂ (2×50 mL). The organic layer was washed with saturated aqueous NaHCO₃ (20 mL) and brine, and dried over Na₂SO₄. The solvent was evaporated and the residue was purified on silica-gel column and eluted with 40-50% ethyl acetate in hexane to give 770 mg (96%) of 48 as a viscous oil. $^1$H NMR (400 MHz, CDCl₃) δ 7.16 (d, J=8.2 Hz, 1H), 6.21 (d, J=15.7 Hz, 1H), 6.10-5.99 (m, 1H), 5.81-5.72 (m, 2H), 5.53 (dd, J=15.7, 6.6 Hz, 1H), 5.42 (t, J=7.1 Hz, 1H), 4.52 (t, J=5.3 Hz, 1H), 4.45-4.33 (m, 1H), 3.97-3.80 (m, 5H), 2.50 (s, 2H), 2.49-2.39 (m, 3H), 1.97-1.74 (m, 3H), 1.67 (s, 3H), 1.50 (s, 3H), 1.33 (s, 3H), 1.31 (d, J=6.7, 3H), 1.21 (s, 3H), 1.17-1.11 (m, 2H), 1.11-1.07 (m, 7H); $^{13}$C NMR (101 MHz, CDCl₃) δ 176.71, 164.82, 142.32, 135.64, 135.62, 127.99, 125.65, 123.25, 102.19, 73.05, 70.23, 70.20, 69.47, 68.55, 55.66, 51.06, 43.73, 42.46, 38.59, 34.16, 34.02, 31.54, 23.77, 20.04, 18.98, 18.90, 12.63; IR (Neat Film) 3332, 2974, 2936, 2871, 1730, 1669, 1638, 1525, 1415, 1373, 1266, 1195, 1130 cm$^{-1}$; MS (ESI) m/z 492.3 (M+1)$^+$; HRMS (ESI) m/z Calcd for C₂₇H₄₂NO₇ (M+1)$^+$ 492.2961. found 492.2949.

51. Synthesis of (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopent-3-en-2-yl pivalate 49

A solution of alcohol 47 (10 mg, 0.02 mmol) in CH₂Cl₂ (1 mL) was stirred at 0° C. as Et₃N (17 μL, 0.11 mmol) and DMAP (0.58 mg, 4.74 μmol) were sequentially added. After 5 min, pivaloyl chloride (8.7 μL, 0.07 mmol) was added. The reaction solution was allowed to stir for 30 min at the same temp. The reaction mixture was diluted with water (4 mL) and CH₂Cl₂ (10 mL). The aq layer was extracted with CH₂Cl₂ (2×11 mL). The organic layer was washed with saturated aqueous NaHCO₃ (5 mL) and brine (5 mL), and dried over Na₂SO₄. The solvent was evaporated and the residue was purified by silica-gel column (30% ethyl acetate in hexane) to give 9 mg (75%) of 49 as viscous solid. $^1$H NMR (400 MHz, CDCl₃) δ 7.22 (d, J=8.2 Hz, 1H), 6.27 (d, J=15.7 Hz, 1H), 6.13-6.05 (m, 1H), 5.89-5.76 (m, 2H), 5.60 (dd, J=15.7, 6.6 Hz, 1H), 5.48 (t, J=7.2 Hz, 1H), 4.58 (t, J=5.3 Hz, 1H), 4.46 (ddd, J=11.4, 6.7, 1.8, 1H), 4.02-3.89 (m, 5H), 2.57 (s, 2H), 2.52-2.44 (m, 2H), 2.03-1.84 (m, 2H), 1.74 (s, 3H), 1.39 (s, 3H), 1.35 (d, 3H), 1.28 (s, 3H), 1.23-1.13 (m, 2H), 1.19 (s, 9H); $^{13}$C NMR (101 MHz, CDCl₃) δ 178.10, 164.83, 142.52, 135.65, 135.62, 127.99, 125.65, 123.16, 102.19, 73.05, 70.22, 70.20, 69.47, 68.59, 55.67, 51.05, 43.72, 42.46, 38.62, 38.58, 34.16, 31.53, 27.13, 23.77, 19.94, 12.64; IR (Neat Film) 3331, 2973, 2932, 2868, 1725, 1670, 1638, 1524, 1461, 1371, 1277, 1161, 1130 cm$^{-1}$; MS (ESI) m/z 506 (M+1)$^+$; HRMS (ESI) m/z Calcd for C₂₈H₄₄NO₇ (M+1)$^+$ 506.3118. found 506.3112.

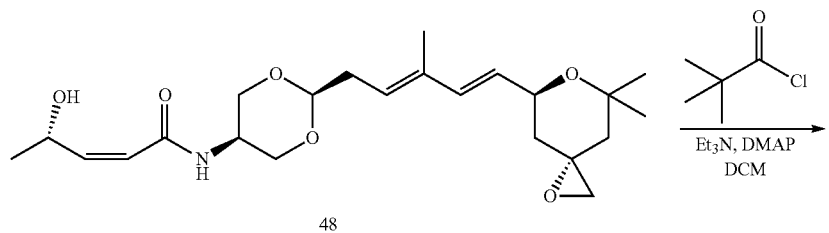

48

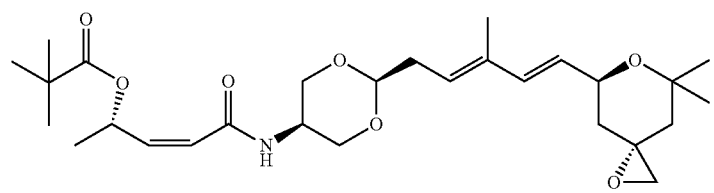

49

52. Synthesis of (S,Z)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-yl)(methyl)amino)-5-oxopent-3-en-2-yl isobutyrate 50

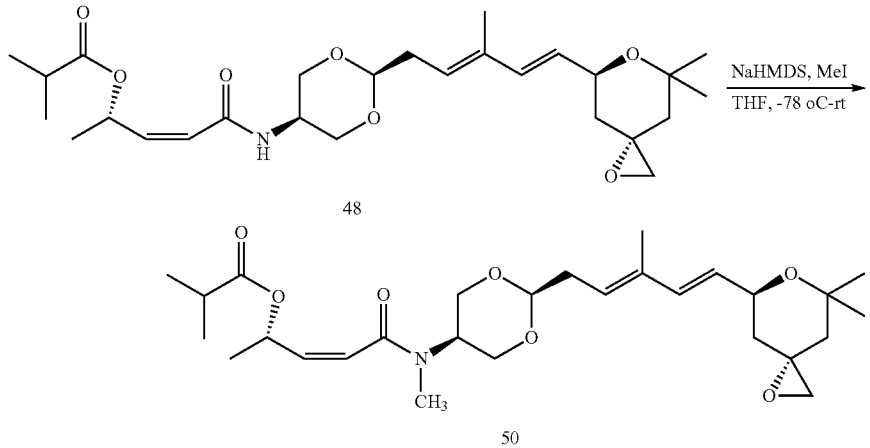

To a cooled solution (−78° C.) of amide 48 (10 mg, 0.02 mmol) in anhyd THF (0.5 mL) was added NaHMDS (22 µL, 1M in THF). After 30 min at −78° C., methyl iodide (14 mg, 0.1 mmol) was added. The resulting solution was stirred another 3 h at −78° C. and then allowed to stir at room temperature for 4 h. Saturated aqueous NH$_4$Cl (2 mL) was added and the product was extracted with EtOAc (2×10 mL). The combined layers were dried over Na$_2$SO$_4$ and then concentrated. The crude residue was purified on Pre-SFC(ODH column, 10% MeOH) to give 3.6 mg (35%) of 50 as oil. $^1$H NMR (400 MHz, CDCl$_3$) δ 6.26 (d, J=15.7 Hz, 1H), 6.15 (d, J=10.6 Hz, 1H), 5.83 (dt, J=13.9, 8.2 Hz, 2H), 5.60 (dd, J=15.7, 6.6 Hz, 1H), 5.50 (t, J=7.2 Hz, 1H), 4.62 (t, J=5.1 Hz, 1H), 4.50-4.43 (m, 1H), 4.33 (s, 1H), 4.24-4.05 (m, 4H), 3.35 (s, 3H), 2.57 (s, 2H), 2.52-2.44 (m, 3H), 2.04-1.85 (m, 2H), 1.74 (s, 3H), 1.40 (s, 3H), 1.38 (d, J=6.2, 3H), 1.28 (s, 3H), 1.23-1.11 (m, 2H) 1.15 (s, 3H), 1.14 (s, 3H); $^{13}$C NMR (101 MHz, CDCl$_3$) δ 176.21, 167.09, 140.55, 135.66, 135.65, 127.93, 125.67, 123.00, 101.59, 73.05, 70.06, 69.51, 68.51, 55.68, 51.06, 45.85, 42.46, 38.59, 34.47, 34.34, 34.05, 31.54, 23.77, 19.97, 18.94, 12.63; IR (Neat Film) 2972, 1730, 1625, 1371, 1193, 1040 cm$^{-1}$; MS (ESI) m/z 506 (M+1)$^+$.

53. Synthesis (S)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopentan-2-yl acetate (53)

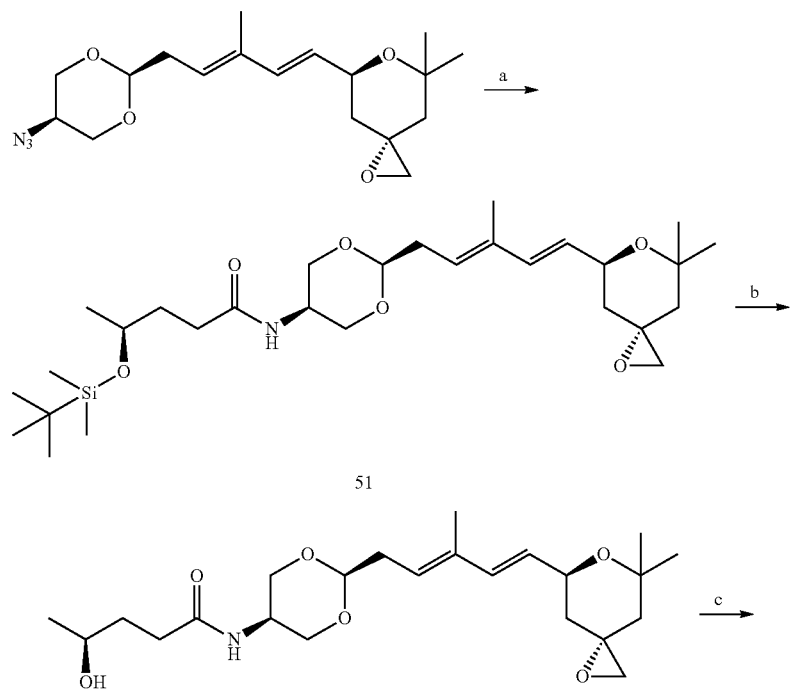

-continued

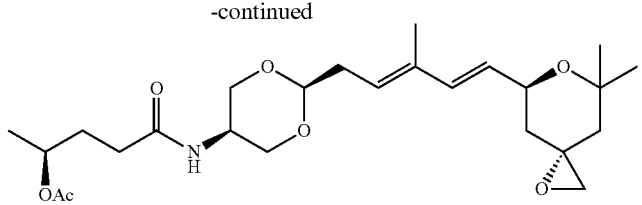

53

Reagents and conditions: (a) i) Ph₃P, benzene, H₂O, 45° C.; ii) (S)-4-(tert-butyldimethylsilyloxy)pentanoic acid, HBTU, Hunig's base, CH₃CN; (b) Bu₄NF, THF, 0° C.; (c) acetic anhydride, Et₃N, DMAP, CH₂Cl₂.

54. (S)-4-(tert-butyldimethylsilyloxy)-N-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylpentanamide (51)

51

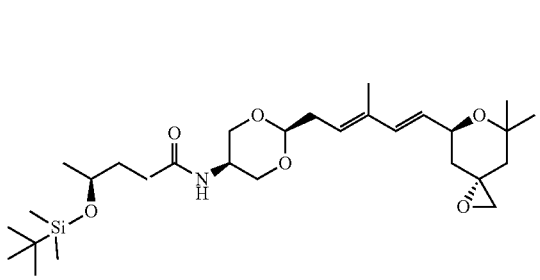

(S)-4-(tert-butyldimethylsilyloxy)pentanoic acid (42 mg, 0.179 mmol) was dissolved in anhydrous CH₃CN (400 μL) and cooled in an ice bath to 0° C. HBTU (65 mg, 0.17 mmol) and DIPEA (96 μL, 0.538 mmol) were added to the reaction flask. (2S,5R)-2-((2E,4E)-5-((3R,5S)-7,7-dimethyl-1,6-dioxaspiro[2.5]octan-5-yl)-3-methylpenta-2,4-dienyl)-1,3-dioxan-5-amine (29 mg, 0.09 mmol) dissolved in CH₃CN (300 μL) and cooled to 0° C. was then added to the reaction flask which was stirred at 0° C. for 10 minutes. The reaction was allowed to warm to room temperature and stirred overnight. A TLC was taken in 50% EtOAc/Hexane. The reaction mixture was diluted with EtOAc (10 mL) and partitioned with saturated NaHCO₃. The aqueous layer was extracted with EtOAc (2×5 mL), washed with brine (10 mL), dried over Na₂SO₄ and concentrated. The crude product was chromatographed on an SP4 Biotage using the 10-80% method with EtOAc and hexane to give product 51, 14 mg (29%). ¹H NMR (400 MHz, CDCl₃) δ 6.35 (d, J=8.9, 1H), 6.28 (d, J=15.7, 1H), 5.61 (dd, J=15.8, 6.6, 1H), 5.48 (t, J=7.3, 1H), 4.57 (t, J=5.3, 1H), 4.51-4.41 (m, 1H), 3.92 (q, J=11.5, 5H), 2.57 (s, 2H), 2.51-2.45 (m, 2H), 2.30 (dtd, J=14.9, 8.8, 3.3, 2H), 1.99 (d, J=14.5, 1H), 1.91 (dd, J=13.6, 11.7, 1H), 1.84 (s, 1H), 1.79 (ddd, J=8.0, 5.5, 3.6, 1H), 1.77-1.72 (m, 3H), 1.40 (s, 3H), 1.28 (s, 3H), 1.25 (s, 1H), 1.24-1.21 (m, 1H), 1.20-1.17 (m, 1H), 1.15 (d, J=6.1, 3H), 0.90 (s, 9H), 0.06 (s, 6H). ¹³C NMR (101 MHz, CDCl₃) δ 173.27, 136.37, 136.16, 128.76, 126.07, 102.95, 73.71, 71.10, 70.09, 68.40, 56.30, 51.69, 44.24, 43.10, 39.22, 35.71, 34.84, 33.38, 32.17, 26.58, 24.43, 18.76, 13.30, −3.66, −4.03.

55. (S)—N-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-yl)-4-hydroxypentanamide (52)

52

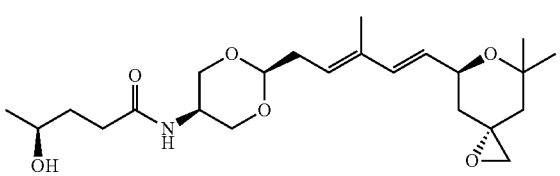

4-(tert-butyldimethylsilyloxy)-N-((2S,5R)-2-((2E,4E)-5-((3R,5S)-7,7-dimethyl-1,6-dioxaspiro[2.5]octan-5-yl)-3-methylpenta-2,4-dienyl)-1,3-dioxan-5-yl)pentanamide (14 mg, 0.026 mmol) was dissolved in THF (1 mL) and cooled in an ice bath. After 10 min TBAF (60 μL, 0.06 mmol) was added to the reaction mixture which was stirred for 8 hr 30 min. A TLC was taken in 50% EtOAc/Hex and stained with CAM. The reaction mixture was concentrated and chromatographed using 5% MeOH/CHCl₃ to yield product 5 mg (45%). ¹H NMR (400 MHz, CDCl₃) δ 6.55 (d, J=7.9 Hz, 1H), 6.28 (d, J=15.7 Hz, 1H), 5.61 (dd, J=15.7, 6.6 Hz, 1H), 5.49 (t, J=7.2 Hz, 1H), 4.59 (t, J=5.1 Hz, 1H), 4.46 (ddd, J=11.3, 6.6, 1.9 Hz, 1H), 3.97-3.90 (m, 5H), 2.59-2.56 (m, 2H), 2.51-2.45 (m, 2H), 2.42 (td, J=7.0, 3.6 Hz, 2H), 1.99 (d, J=13.8 Hz, 1H), 1.95-1.87 (m, 1H), 1.84 (td, J=7.5, 3.8 Hz, 1H), 1.74 (d, J=4.3 Hz, 3H), 1.40 (s, 3H), 1.28 (s, 3H), 1.25 (s, 1H), 1.22 (s, 3H), 1.22-1.18 (m, 3H), 1.18-1.13 (m, 1H). ¹³C NMR (101 MHz, CDCl₃) δ 173.78, 136.43, 136.21, 128.76, 126.04, 102.86, 73.73, 70.94, 70.91, 70.12, 68.20, 56.33, 51.71, 44.44, 43.09, 39.22, 34.85, 34.76, 33.99, 32.17, 24.42, 24.39, 13.30.

56. (S)-5-((2R,5R)-2-((2E,4E)-5-((3R,5S)-7,7-dimethyl-1,6-dioxaspiro[2.5]octan-5-yl)-3-methylpenta-2,4-dienyl)-1,3-dioxan-5-ylamino)-5-oxopentan-2-yl acetate (53)

53

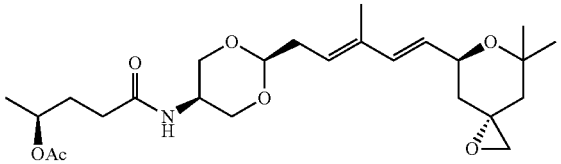

N-((2S,5R)-2-((2E,4E)-5-((3R,5S)-7,7-dimethyl-1,6-dioxaspiro[2.5]octan-5-yl)-3-methylpenta-2,4-dienyl)-1,3-dioxan-5-yl)-4-hydroxypentanamide (8 mg, 0.019 mmol) was dissolved in DCM (1 mL) and cooled in an ice bath. After 10 minutes TEA (18 µL, 0.132 mmol) followed by DMAP (1.2 mg, 9.44 µmol) were added to the reaction mixture which was stirred for 5 minutes before adding $Ac_2O$ (6.36 mg, 0.062 mmol). The reaction was stirred overnight at 0° C. and a TLC was taken in 5% $MeOH/CHCl_3$. The reaction mixture was concentrated and immediately chromatographed using 70% EtOAc/Hex to give 5 mg of 53 (57%). $^1H$ NMR (400 MHz, $CDCl_3$) δ 6.44 (d, J=8.4 Hz, 1H), 6.28 (d, J=15.7 Hz, 1H), 5.61 (dd, J=15.7, 6.7 Hz, 1H), 5.48 (t, J=7.4 Hz, 1H), 4.95 (dd, J=12.6, 6.3 Hz, 1H), 4.58 (t, J=5.3 Hz, 1H), 4.46 (ddd, J=11.1, 6.5, 1.8 Hz, 1H), 3.92 (q, J=11.5 Hz, 5H), 2.57 (s, 1H), 2.51-2.46 (m, 1H), 2.36-2.20 (m, 2H), 2.05 (s, 3H), 1.99 (d, J=14.6 Hz, 1H), 1.92 (ddd, J=8.5, 6.0, 3.4 Hz, 2H), 1.75 (d, J=0.7 Hz, 2H), 1.40 (s, 3H), 1.29 (d, J=5.1 Hz, 3H), 1.26 (s, 3H), 1.24 (s, 3H), 1.19 (d, J=2.3 Hz, 1H), 1.16 (dd, J=13.8, 2.0 Hz, 1H).

57. Synthesis of N-((2S,5R)-2-((2E,4E)-5-((3R,5S)-7,7-dimethyl-1,6-dioxaspiro[2.5]octan-5-yl)-3-methylpenta-2,4-dienyl)-1,3-dioxan-5-yl)acetamide (54)

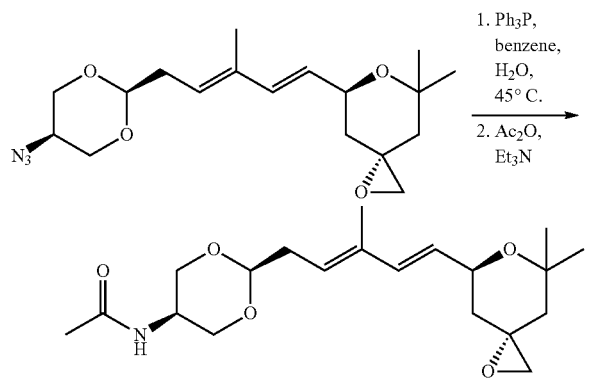

(2S,5R)-2-((2E,4E)-5-((3R,5S)-7,7-dimethyl-1,6-dioxaspiro[2.5]octan-5-yl)-3-methylpenta-2,4-dienyl)-1,3-dioxan-5-amine (9 mg, 0.029 mmol) which had been dried azeotrpically in $CH_3CN$ was dissolved in DCM (1.8 mL). DIPEA (51 µL, 0.294 mmol) was added to the reaction mixture followed by $Ac_2O$ (14 µL, 0.147 mmol). The reaction was stirred at room temp for 28 hrs. The reaction mixture was concentrated and chromatographed using 5% $MeOH/CHCl_3$ to give 1.2 mg of 54 (12%). $^1H$ NMR (400 MHz, $CDCl_3$) δ 6.39 (d, J=8.0 Hz, 1H), 6.28 (d, J=15.8 Hz, 1H), 5.61 (dd, J=15.7, 6.6 Hz, 1H), 5.48 (t, J=7.3 Hz, 1H), 4.58 (t, J=5.3 Hz, 1H), 4.51-4.42 (m, 1H), 3.99-3.87 (m, 5H), 2.57 (s, 2H), 2.52-2.45 (m, 2H), 2.05 (s, 3H), 1.99 (d, J=14.2 Hz, 1H), 1.91 (dd, J=13.7, 11.7 Hz, 1H), 1.75 (d, J=1.0 Hz, 3H), 1.40 (s, 3H), 1.28 (s, 3H), 1.24-1.18 (m, 1H), 1.16 (dd, J=13.8, 2.0 Hz, 1H). $^{13}C$ NMR (101 MHz, $CDCl_3$) δ 170.25, 136.41, 136.20, 128.77, 126.03, 102.93, 73.72, 71.05, 70.12, 56.31, 51.71, 44.40, 43.10, 39.24, 34.82, 32.18, 24.42, 24.12, 13.31.

58. Cell Culture Procedure

The A549 lung cancer, WiDr colorectal cancer, MCF-7 breast cancer, PC-3 prostate cancer, and OVCAR-3 ovarian cancer cell lines were purchased from the American Type Culture Collection (ATCC, Manassas, Va.) and were maintained in growth media as recommended by the ATCC. The JeKo-1 and JVM-2 mantle cell lymphoma cell lines were purchased from the DSMZ (Brunswick, Germany) and were maintained in growth media as recommended by the vendor. All cell lines were grown under standard culture conditions at 37° C. and 5% $CO_2$ in a humidified environment.

59. In Vitro Cytoxicity Analysis

Cell viabilities were determined by measuring the cleavage of (sodium 3'-[1-(phenylaminocarbonyl)-3,4-tetrazolium]-bis(4-methoxy-6-nitro) benzene sulfonic acid hydrate) (XTT) to a water-soluble orange formazan by mitochondrial dehydrogenase, following the manufacturer's instructions (Roche Applied Science, Indianapolis, Ind.). Briefly, cell lines were seeded at various cell densities depending on the cell type. The adherent cell lines were allowed to adhere overnight before compound addition, whereas the suspension cell lines were seeded the day of compound addition. Stock concentrations of the compounds were made in DMSO, diluted in culture media and subsequently added to the plates at various final concentrations, then incubated for 72 hours. After the incubation period, the XTT labeling reagent, containing the electron-coupling reagent, was added to each well and incubated for 4 hours. The absorbance of each well was then read at 490 nm with a reference wavelength of 690 nm using a VersaMax™ microplate reader (Sunnyvale, Calif.). Data are expressed as the percentage of growth compared to vehicle-treated cells, as calculated from absorbance and corrected for background absorbance. The $IC_{50}$ is defined as the drug concentration that inhibits growth to 50% of the vehicle-treated control; $IC_{50}$ values were calculated from sigmoidal analysis of the dose response curves using Origin v7.5 software (Northampton, Mass.).

Tables 1-3 display cytotoxicity data for exemplary compounds following a 72-hour exposure.

TABLE 1

Cytotoxicity $IC_{50}$s for ester analogs (µmol)

| Cell line | Compound number | | | | | | | | |
|---|---|---|---|---|---|---|---|---|---|
| | 15 | 16 | 17 | 18 | 19 | 20 | 21 | 22 | 23 |
| PC3 | 1.9 | 10 | 1.97 | 3.5 | 4.3 | 4.9 | 8.1 | >10 | 0.76 |
| JEKo1 | 0.04 | >1 | 0.44 | 0.14 | 0.39 | 0.41 | 0.16 | >1 | 0.03 |

TABLE 2

Cytotoxicity $IC_{50}$s for carbamate analogs (µmol)

| Cell line | Compound number | | | | |
|---|---|---|---|---|---|
| | 24 | 25 | 26 | 27 | 28 |
| JEKo1 | ND | >0.5 | >0.5 | >0.5 | ND |
| JVM-2 | >1.0 | >0.5 | >0.5 | >0.5 | >10.0 |
| PC3 | >0.5 | >2.5 | >2.5 | >2.5 | >5.0 |
| WiDr | 4-5 | >1.25 | >0.5 | >1.25 | >1.25 |

TABLE 3

| | Cytotoxicity IC$_{50}$s (µmol) | | | |
| --- | --- | --- | --- | --- |
| | Compound number | | | |
| Cell line | 38 | 48 | 49 | 53 |
| JEKo1 | >1 | 0.17 | 0.34 | >1 |
| PC3 | >10 | 5.2 | 1.18 | >10 |

60. Cell Cycle Analysis

Cell cycle analysis was performed by treating A549, JeKo-1, and WiDr cancer cell lines with a range of compound 1 concentrations overnight for 18 hours. After the incubation period, the cells were harvested and fixed with ethanol, then incubated with RNAse A and propidium iodide (PI). Fluorescence was detected using the BD FACSCalibur flow cytometer and analyzed using Cell Quest Pro software (both from BD Biosciences, San Jose, Calif.). Analysis of the percentage of cells in each of the cell cycle phases (G1, S, or G2/M) was calculated by measuring the DNA content in each sample. The data shown represent the average determinations.

61. Mouse Maximum Tolerated Dose (MTD) Studies

Maximal tolerated dose (MTD) studies were performed using compound 15 at doses ranging from 0 to 50 mg/kg (physico-chemical properties of the compound precluded the administration of higher doses). For this study, NOD/SCID mice (three per group) were dosed with vehicle, 5, 10, 25, or 50 mg/kg of compound 15 daily for five days by both IV and IP routes.

Compound 15 was dissolved in 3.0% DMSO, 6.5% Tween 80 in 5% glucose solution, which is a modification of the formulation used by Mizui et al. for the spliceosome inhibitor pladienolide B. To determine compound-related toxicities, mice were monitored daily for weight loss, morbidity, and mortality. Following administration of the last dose of compound 15, complete blood counts (CBCs) were measured along with a full diagnostic chemistry panel measuring albumin, alkaline phosphatase, alanine aminotransferase (ALT), amylase, blood urea nitrogen (BUN), calcium, creatinine, globulin, glucose, phosphorous, potassium, sodium, total bilirubin, and total protein. No significant differences in blood cell counts were observed in treated versus vehicle-only mice, indicating that compound 15 is not associated with the induction of anemia, leukopenia or thrombocytopenia when administered under these conditions. The mice were monitored for one week following compound administration. No significant weight loss was observed in any group. There was one fatality in the IP 25 mg/kg and one in the IV 50 mg/kg groups. Total necropsies to assess organ histologies of animals from the various treatment and vehicle-only groups showed no significant toxicities in these mice.

62. In Vivo Efficacy Studies

Studies were carried out to determine whether the above doses were capable of inhibiting tumor growth in mice (FIG. 4). For these studies, JeKo-1 mantle cell lymphoma tumors (which we found to be sensitive to spliceosome inhibitor compounds) were implanted into NOD/SCID mice on day 0. Beginning on day 4, the mice received IV injections of vehicle, 5, 10, 25, or 50 mg/kg of compound 15 daily for five consecutive days. No fatalities or significant weight loss were observed in any of the groups. Administration of 10, 25, or 50 mg/kg of compound 15 each led to statistically significant decreases in tumor volumes compared to vehicle-treated mice. A widely used criterion for determining antitumor activity is tumor growth inhibition (T/C). This value is calculated by dividing the median tumor volumes of treated mice by the median volumes in control mice. According to NCI standards, a T/C≤42% is the minimum requirement for activity. By performing this calculation, we determined that the 50 mg/kg compound 15 dose achieved a T/C value of 35%. These data indicate that even a first-generation, minimally optimized compound from this series of spliceosome inhibitors could be administered at the doses necessary to inhibit tumor growth without significant toxicity.

63. Stability Studies

Stability studies were performed for exemplary compounds 48 and 15. A 100 µM solution of compound 48 was prepared in buffer (PBS, pH 7.4) and warfarin was used as an internal standard. A sample was injected into a HPLC periodically starting at day 0 and ending at about 6 weeks to find out the stability of compound 48 in PBS solution. No degradable products were found after 1 day. After 1 week, a new peak was observed along with compound 48 that exhibits a mass of 510 (M+1), which is the water addition product of compound 48. After 6 weeks, 58% of compound 48 remained in the buffer solution. The calculated half life of the compound 48 is 50.4 days.

Analogously, a 100 µM solution of compound 15 in PBS buffer and DMSO was prepared (2:1) and warfarin was used as an internal and external standard. A sample was injected into a HPLC periodically starting at day 0 and ending at about 6 weeks to find out the stability of compound 15. After 6 weeks, 53% of the compound 15 remained in the buffer and at the same time a new peak was observed that exhibits a mass of 506 (M+1), which is the water addition product of 15. The calculated half life of the compound 15 is 50.6 days.

Without wishing to be bound by theory, it is believed that the observed stability is due to the absence of the hydroxyl group at $R^5$ or $R^6$. The stability of the disclosed compounds, in contrast to FR901464 (FR) and related compounds, is likely enhanced due to the absence of the hydroxyl group at $R^5$ or $R^6$.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

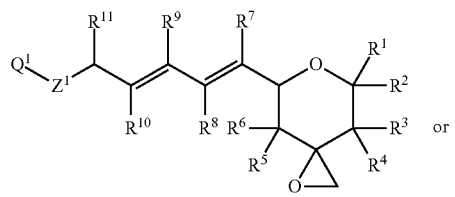

or

-continued

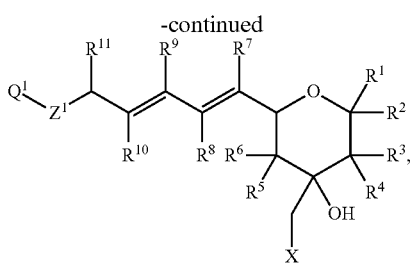

wherein each of $R^1$, $R^2$, $R^3$, $R^4$, $R^5$, and $R^6$ are independently selected from halogen, hydrogen, hydroxyl, amino, thiol, and optionally substituted C1-C6 organic residue;
wherein each of $R^7$, $R^8$, $R^{10}$, and $R^{11}$ is hydrogen;
wherein $R^9$ is hydrogen or an optionally substituted organic residue comprising from 1 to 4 carbons;
wherein X is a leaving group; and
wherein $Z^1$ is an optionally substituted 3, 4, 5, or 7 membered ring, or an unsubstituted 6-membered ring selected from:

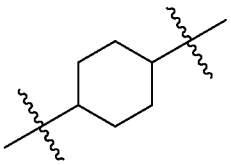 and 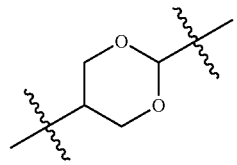 ;

wherein $Q^1$ is selected from:

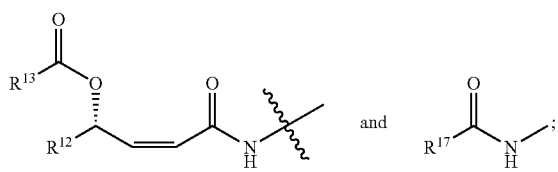

wherein $R^{12}$ and $R^{13}$ independently are hydrogen or optionally substituted organic residue from 1 to 16 carbons; and
wherein $R^{17}$ represents optionally substituted $C_1$-$C_4$ alkyl; or a pharmaceutically acceptable salt thereof.

2. The compound of claim 1, wherein the compound has a structure represented by a formula:

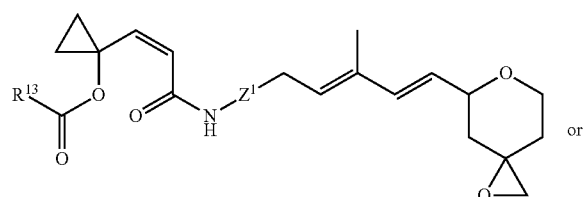

or

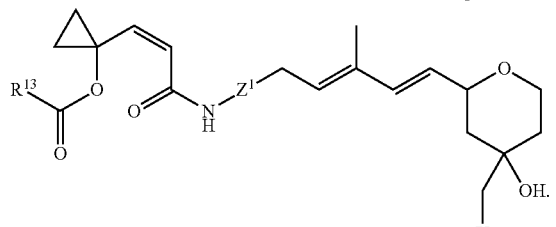

3. A method for inhibiting cell replication comprising the step of contacting at least one cell with an effective amount of a compound having the structure represented by the formula:

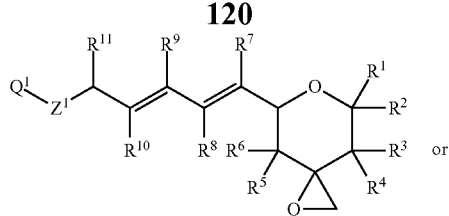

or

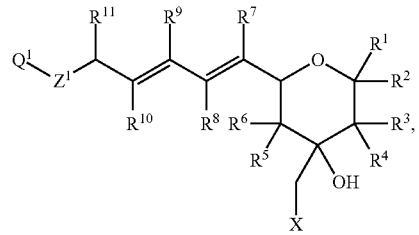

wherein each of $R^1$, $R^2$, $R^3$, $R^4$, $R^5$, and $R^6$ are independently selected from halogen, hydrogen, hydroxyl, amino, thiol, and optionally substituted C1-C6 organic residue;
wherein each of $R^7$, $R^8$, $R^{10}$, and $R^{11}$ is hydrogen; $R^9$ is hydrogen or an optionally substituted organic residue comprising from 1 to 4 carbons;
wherein X is a leaving group; and
wherein $Z^1$ is an optionally substituted 3, 4, 5, or 7 membered ring, or an unsubstituted 6-membered ring selected from:

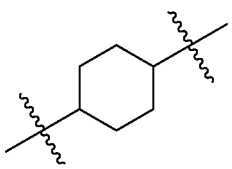 and 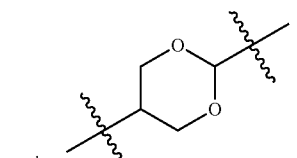 ;

wherein $Q^1$ is selected from:

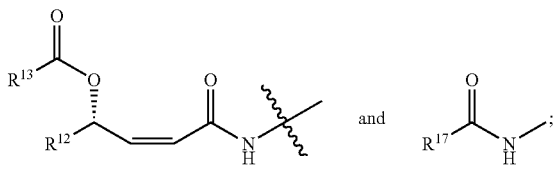

wherein $R^{12}$ and $R^{13}$ independently are hydrogen or optionally substituted organic residue from 1 to 16 carbons; and
wherein $R^{17}$ represents optionally substituted $C_1$-$C_4$ alkyl; or a pharmaceutically acceptable salt thereof;
thereby inhibiting replication of the at least one cell.

4. The method of claim 3, wherein inhibiting is preventing.

5. The method of claim 3, wherein the at least one cell is a cancer cell.

6. The method of claim 3, wherein the step of contacting occurs in vivo.

7. The method of claim 3, wherein the step of contacting occurs in vitro.

8. A method of making a Spiro epoxide derivative, comprising the steps of:
(a) providing a compound having a structure represented by the formula:

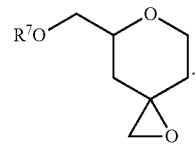

wherein R$^7$ hydrogen; and
(b) performing an oxidation reaction to provide the spiro epoxide derivative, wherein the spiro epoxide derivative has a structure represented by a formula:

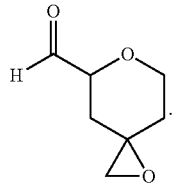

9. The method of claim 8, wherein the providing step comprises the step of reducing a compound having a structure represented by a formula:

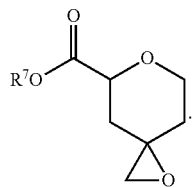

wherein R$^7$ is hydrogen or an optionally substituted C1-C6 organic residue.

10. The compound of claim 1, wherein the compound has a structure represented by a formula:

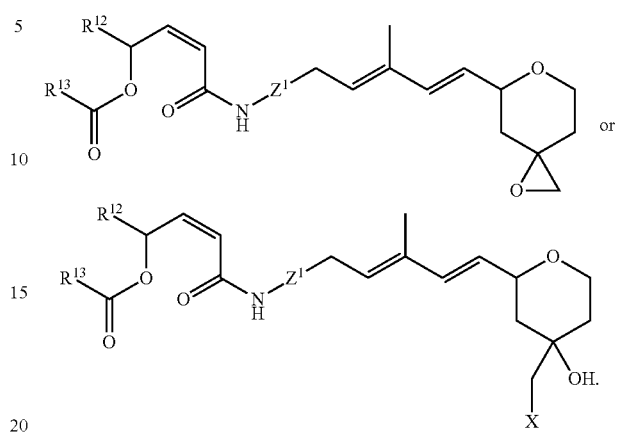

11. The compound of claim 1, wherein R$^{12}$ is hydrogen, optionally substituted methyl, ethyl, propyl, butyl, pentyl, or hexyl.

12. The compound of claim 1, wherein R$^{13}$ is alkylamino, dialkylamino, or cycloalkylamino from 1 to 12 carbons.

* * * * *